US012723067B2

(12) United States Patent
Chen et al.

(10) Patent No.: US 12,723,067 B2
(45) Date of Patent: Sep. 1, 2026

(54) HUMAN INTERLEUKIN-2 VARIANT OR DERIVATIVE THEREOF

(71) Applicants: JIANGSU HENGRUI MEDICINE CO., LTD., Lianyungang (CN); SHANGHAI HENGRUI PHARMACEUTICAL CO., LTD., Shanghai (CN); SHANGHAI SHENGDI PHARMACEUTICAL CO., LTD., Shanghai (CN)

(72) Inventors: Lei Chen, Lianyungang (CN); Qiyue Hu, Shanghai (CN); Hu Ge, Shanghai (CN); Yuan Lin, Shanghai (CN); Hongwei Wang, Lianyungang (CN); Yangchao Ou, Lianyungang (CN); Xianglin Kong, Lianyungang (CN); Cheng Liao, Shanghai (CN); Lianshan Zhang, Lianyungang (CN)

(73) Assignees: JIANGSU HENGRUI MEDICINE CO., LTD., Lianyungang (CN); SHANGHAI HENGRUI PHARMACEUTICAL CO., LTD., Shanghai (CN); SHANGHAI SHENGDI PHARMACEUTICAL CO., LTD., Shanghai (CN)

( * ) Notice: Subject to any disclaimer, the term of this patent is extended or adjusted under 35 U.S.C. 154(b) by 845 days.

(21) Appl. No.: 17/414,062

(22) PCT Filed: Dec. 20, 2019

(86) PCT No.: PCT/CN2019/126901
§ 371 (c)(1),
(2) Date: Jun. 15, 2021

(87) PCT Pub. No.: WO2020/125743
PCT Pub. Date: Jun. 25, 2020

(65) Prior Publication Data

US 2022/0056094 A1 Feb. 24, 2022

(30) Foreign Application Priority Data

Dec. 21, 2018 (CN) ......................... 201811570930.5
Mar. 4, 2019 (CN) ......................... 201910158957.1

(51) Int. Cl.
*C07K 14/55* (2006.01)
*A61K 47/60* (2017.01)
*A61P 35/00* (2006.01)
*A61K 38/00* (2006.01)

(52) U.S. Cl.
CPC .............. *C07K 14/55* (2013.01); *A61K 47/60* (2017.08); *A61P 35/00* (2018.01); *A61K 38/00* (2013.01)

(58) Field of Classification Search
CPC ........................... C07K 14/55; C07K 2319/30; C07K 14/5434; A61K 47/60; A61K 38/00; A61K 38/2013; A61K 38/208; A61P 35/00; A61P 37/00; A61P 3/10; C12N 15/70
See application file for complete search history.

(56) References Cited

U.S. PATENT DOCUMENTS

| | | | | |
|---|---|---|---|---|
| 7,371,371 | B2 | 5/2008 | Epstein et al. | |
| 7,514,073 | B2 | 4/2009 | Epstein et al. | |
| 7,803,361 | B2 | 9/2010 | Epstein et al. | |
| 8,124,066 | B2 | 2/2012 | Epstein et al. | |
| 8,906,356 | B2 | 12/2014 | Wittrup et al. | |
| 9,732,134 | B2 | 8/2017 | Gavin et al. | |
| 2005/0142106 | A1* | 6/2005 | Wittrup | G01N 33/6869 435/69.52 |
| 2018/0340014 | A1* | 11/2018 | Viney | C07K 14/55 |

FOREIGN PATENT DOCUMENTS

| | | | | | |
|---|---|---|---|---|---|
| CN | 1599867 | A | | 3/2005 | |
| CN | 103492411 | A | | 12/2016 | |
| WO | WO-8500817 | A | * | 2/1985 | C07H 21/04 |
| WO | 1999060128 | A1 | | 11/1999 | |
| WO | 2005007121 | A2 | | 1/2005 | |
| WO | 2009135615 | A2 | | 11/2009 | |
| WO | 2012062228 | A2 | | 5/2012 | |
| WO | WO-2012107417 | A1 | * | 8/2012 | A61K 38/2013 |
| WO | 2016014428 | A2 | | 1/2016 | |
| WO | 2017136818 | A | | 8/2017 | |

* cited by examiner

*Primary Examiner* — Sudhakar Katakam
(74) *Attorney, Agent, or Firm* — Morgan, Lewis & Bockius LLP

(57) ABSTRACT

Provided is a human interleukin-2 (IL-2) variant having one or more amino acid mutations or a derivative thereof. The IL-2 variant or derivative thereof has increased stability compared to wild-type IL-2 and improved properties as an immunotherapeutic agent. Also disclosed are an immunoconjugate and a pharmaceutical composition which comprise the human IL-2 variant or derivative thereof, a polynucleotide molecule encoding same, a vector, a host cell and a preparation method therefor, as well as the pharmaceutical uses of the IL-2 variant or derivative thereof and the immunoconjugate or pharmaceutical composition comprising the L-2 variant or derivative thereof.

4 Claims, 16 Drawing Sheets

Specification includes a Sequence Listing.

Concentration of IL-2 or variant thereof (nM)

40000
30000
20000
10000
0
pSTAT5 (MFI)
0.01 0.1 1 10 100 1000
IL-2(WT)
PEG-IL-2-10
PEG-IL-2-23

Concentration (nM)

SEQUENCE LISTING

```
<160> NUMBER OF SEQ ID NOS: 41

<210> SEQ ID NO 1
<211> LENGTH: 417
<212> TYPE: DNA
<213> ORGANISM: Artificial Sequence
<220> FEATURE:
<223> OTHER INFORMATION: Synthetic Sequence_Wild type IL-2 nucleic acid
      sequence

<400> SEQUENCE: 1

catatggcac cgaccagcag cagcaccaaa aaaacccagc tgcaactgga acatctgctg     60

ttagatctgc aaatgattct gaacggcatc aacaactaca aaaatccgaa actgacccgt    120

atgctgacct tcaaattcta catgccgaaa aaagcaaccg agctgaaaca tctgcagtgt    180

ctggaagaag aactgaaacc gctggaagag gttctgaatc tggcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttaccttttg tcagagcatt attagcaccc tgacctaatg aggatcc       417


<210> SEQ ID NO 2
<211> LENGTH: 134
<212> TYPE: PRT
<213> ORGANISM: Artificial Sequence
<220> FEATURE:
<223> OTHER INFORMATION: Synthetic Sequence_Wild type IL-2 amino acid
      sequence

<400> SEQUENCE: 2

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60
```

```
Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130


<210> SEQ ID NO 3
<211> LENGTH: 417
<212> TYPE: DNA
<213> ORGANISM: Artificial Sequence
<220> FEATURE:
<223> OTHER INFORMATION: Synthetic Sequence_IL-2-01 nucleic acid
      sequence

<400> SEQUENCE: 3

catatggcac cgaccagcag cagcaccaaa aaaacccagc tgcaactgga acatctgctg      60

ttagatctgc aaatgattct gcagggcatc aacaactaca aaaatccgaa actgacccgt     120

atgctgacct tcaaattcta catgccgaaa aaagcaaccg agctgaaaca tctgcagtgt     180

ctggaagaag aactgaaacc gctggaagag gttctgaatc tggcacagag caaaaacttt     240

catctgcgtc cgcgtgatct gattagcaat attaacgtta ttgtgctgga actgaaaggt     300

agcgaaacca cctttatgtg tgaatatgcc gatgaaaccg caaccattgt ggaatttctg     360

aatcgttgga ttacctttgc acagagcatt attagcaccc tgacctaatg aggatcc        417


<210> SEQ ID NO 4
<211> LENGTH: 134
<212> TYPE: PRT
<213> ORGANISM: Artificial Sequence
<220> FEATURE:
<223> OTHER INFORMATION: Synthetic Sequence_IL-2-01 amino acid sequence

<400> SEQUENCE: 4

Met Ala Pro Thr Ser Ser Ser Thr Lys Lys Thr Gln Leu Gln Leu Glu
1               5                   10                  15

His Leu Leu Leu Asp Leu Gln Met Ile Leu Gln Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 5
```

```
<211> LENGTH: 417
<212> TYPE: DNA
<213> ORGANISM: Artificial Sequence
<220> FEATURE:
<223> OTHER INFORMATION: Synthetic Sequence_IL-2-02 nucleic acid
      sequence

<400> SEQUENCE: 5

catatggcac cgaccagcag cagcaccaaa aaaacccagc tgcaactgga acatctgctg     60

ttagatctgc aaatgattct gaacggcatc aacagctaca aaaatccgaa actgacccgt    120

atgctgacct tcaaattcta catgccgaaa aaagcaaccg agctgaaaca tctgcagtgt    180

ctggaagaag aactgaaacc gctggaagag gttctgaatc tggcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc      417


<210> SEQ ID NO 6
<211> LENGTH: 134
<212> TYPE: PRT
<213> ORGANISM: Artificial Sequence
<220> FEATURE:
<223> OTHER INFORMATION: Synthetic Sequence_IL-2-02 amino acid sequence

<400> SEQUENCE: 6

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Ser Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 7
<211> LENGTH: 417
<212> TYPE: DNA
<213> ORGANISM: Artificial Sequence
<220> FEATURE:
<223> OTHER INFORMATION: Synthetic Sequence_IL-2-03 nucleic acid
      sequence

<400> SEQUENCE: 7

catatggcac cgaccagcag cagcaccaaa aaaacctgtc tgcaactgga acatctgctg     60

ttagatctgc aaatgattct gaacggcatc aacaactaca aaaatccgaa actgacccgt    120

atgctgacct tcaaattcta catgccgaaa aaagcaaccg agctgaaaca tctgcagtgt    180

ctggaagaag aactgaaacc gctggaagag gttctgaatc tggcacagag caaaaacttt    240
```

```
catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcacct gtacctaatg aggatcc       417


<210> SEQ ID NO 8
<211> LENGTH: 134
<212> TYPE: PRT
<213> ORGANISM: Artificial Sequence
<220> FEATURE:
<223> OTHER INFORMATION: Synthetic Sequence_IL-2-03 amino acid sequence

<400> SEQUENCE: 8

Met Ala Pro Thr Ser Ser Ser Thr Lys Lys Thr Cys Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Cys Thr
    130


<210> SEQ ID NO 9
<211> LENGTH: 417
<212> TYPE: DNA
<213> ORGANISM: Artificial Sequence
<220> FEATURE:
<223> OTHER INFORMATION: Synthetic Sequence_IL-2-04 nucleic acid
      sequence

<400> SEQUENCE: 9

catatggcac cgaccagcag cagcaccaaa aaaacccagc tgcaactgga acatctgctg     60

ttagatctgc aaatgattct gaacggcatc aacaactaca aaaatccgaa actgacccgt    120

atgctgacct tcaaattcta catgccgaaa aaagcaaccg agctgaaaca tctgcagtgt    180

ctggaagaag aactgaaacc gctggaagag gtttgtaatc tggcacagag caaaaacttt    240

catctgcgtt gtcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417


<210> SEQ ID NO 10
<211> LENGTH: 134
<212> TYPE: PRT
<213> ORGANISM: Artificial Sequence
<220> FEATURE:
<223> OTHER INFORMATION: Synthetic Sequence_IL-2-04 amino acid sequence

<400> SEQUENCE: 10

Met Ala Pro Thr Ser Ser Ser Thr Lys Lys Thr Gln Leu Gln Leu Glu
```

```
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Cys Asn Leu Ala Gln Ser Lys Asn Phe His
65                  70                  75                  80

Leu Arg Cys Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 11
<211> LENGTH: 417
<212> TYPE: DNA
<213> ORGANISM: Artificial Sequence
<220> FEATURE:
<223> OTHER INFORMATION: Synthetic Sequence_IL-2-05 nucleic acid
      sequence

<400> SEQUENCE: 11

catatggcac cgaccagcag cagcaccaaa aaaacccagc tgcaactgga acatctgctg      60

ttagatctgc aaatgattct gaactgtatc aacaactaca aaaatccgaa actgacccgt     120

atgctgacct tcaaattcta catgccgaaa aaagcaaccg agctgaaaca tctgcagtgt     180

ctggaagaag aactgaaacc gctggaagag gttctgaatc tggcacagag caaaaactgt     240

catctgcgtc cgcgtgatct gattagcaat attaacgtta ttgtgctgga actgaaaggt     300

agcgaaacca cctttatgtg tgaatatgcc gatgaaaccg caaccattgt ggaatttctg     360

aatcgttgga ttacctttgc acagagcatt attagcaccc tgacctaatg aggatcc        417


<210> SEQ ID NO 12
<211> LENGTH: 134
<212> TYPE: PRT
<213> ORGANISM: Artificial Sequence
<220> FEATURE:
<223> OTHER INFORMATION: Synthetic Sequence_IL-2-05 amino acid sequence

<400> SEQUENCE: 12

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Cys Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Cys His
65                  70                  75                  80

Leu Arg Pro Arg Asp Leu Ile Ser Asn Ile Asn Val Ile Val Leu Glu
                85                  90                  95
```

```
Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 13
<211> LENGTH: 396
<212> TYPE: DNA
<213> ORGANISM: Artificial Sequence
<220> FEATURE:
<223> OTHER INFORMATION: Synthetic Sequence_IL-2-06 nucleic acid
      sequence

<400> SEQUENCE: 13

catatggcac cgaccagcag cagcaccaaa aaaacccagc tgcaactgga acatctgctg      60

ttagatctgc aaatgattct gaacggcatc cagagcatgc atattgatgc aaccctgtac     120

atgccgaaaa aagcaaccga gctgaaacat ctgcagtgtc tggaagaaga actgaaaccg     180

ctggaagagg ttctgaatct ggcacagagc aaaaactttc atctgcgtcc gcgtgatctg     240

attagcaata ttaacgttat tgtgctggaa ctgaaaggta gcgaaaccac ctttatgtgt     300

gaatatgccg atgaaaccgc aaccattgtg gaatttctga atcgttggat tacctttgca     360

cagagcatta ttagcaccct gacctaatga ggatcc                               396


<210> SEQ ID NO 14
<211> LENGTH: 127
<212> TYPE: PRT
<213> ORGANISM: Artificial Sequence
<220> FEATURE:
<223> OTHER INFORMATION: Synthetic Sequence_IL-2-06 amino acid sequence

<400> SEQUENCE: 14

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Gln Ser Met
            20                  25                  30

His Ile Asp Ala Thr Leu Tyr Met Pro Lys Lys Ala Thr Glu Leu Lys
        35                  40                  45

His Leu Gln Cys Leu Glu Glu Glu Leu Lys Pro Leu Glu Glu Val Leu
    50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
            100                 105                 110

Asn Arg Trp Ile Thr Phe Ala Gln Ser Ile Ile Ser Thr Leu Thr
        115                 120                 125


<210> SEQ ID NO 15
<211> LENGTH: 417
<212> TYPE: DNA
<213> ORGANISM: Artificial Sequence
<220> FEATURE:
<223> OTHER INFORMATION: Synthetic Sequence_IL-2-07 nucleic acid
      sequence

<400> SEQUENCE: 15
```

```
catatggcac cgaccagcag cagcaccaaa aaaacccagc tgcaactgga acatctgctg     60

ttagatctgc aaatgattct gaacggcatc aacaactaca aaaatccgaa actgacccgt    120

atgctgaccg caaaattcgc aatgccgaaa aaagcaaccg agctgaaaca tctgcagtgt    180

ctggaagaag aactgaaacc gctggaagag gttctgaatc tggcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417


<210> SEQ ID NO 16
<211> LENGTH: 134
<212> TYPE: PRT
<213> ORGANISM: Artificial Sequence
<220> FEATURE:
<223> OTHER INFORMATION: Synthetic Sequence_IL-2-07 amino acid sequence

<400> SEQUENCE: 16

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Ala Lys Phe Ala Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 17
<211> LENGTH: 417
<212> TYPE: DNA
<213> ORGANISM: Artificial Sequence
<220> FEATURE:
<223> OTHER INFORMATION: Synthetic Sequence_IL-2-08 nucleic acid
      sequence

<400> SEQUENCE: 17

catatggcac cgaccagcag cagcaccaaa aaaacccagc tgcaactgga acatctgctg     60

ttagatctgc aaatgattct gaacggcatc aacaactaca aaaatccgaa actgacccgt    120

atgctgaccg caaaattcta catgccgaaa aaagcaaccg agctgaaaca tctgcagtgt    180

ctggaagaag aactgaaacc gctggaagag gttctgaatg gcgcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417


<210> SEQ ID NO 18
<211> LENGTH: 134
```

```
<212> TYPE: PRT
<213> ORGANISM: Artificial Sequence
<220> FEATURE:
<223> OTHER INFORMATION: Synthetic Sequence_IL-2-08 amino acid sequence

<400> SEQUENCE: 18

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Gly Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 19
<211> LENGTH: 417
<212> TYPE: DNA
<213> ORGANISM: Artificial Sequence
<220> FEATURE:
<223> OTHER INFORMATION: Synthetic Sequence_IL-2-09 nucleic acid
      sequence

<400> SEQUENCE: 19

catatggcac cgaccagcag cagcaccaaa aaaacccagc tgcaactgga acatctgctg     60

ttagatctgc aaatgattct gaacggcatc aacaactaca aaaatccgaa actgacccgt    120

atgctgacct tcaaattcgc aatgccgaaa aaagcaaccg agctgaaaca tctgcagtgt    180

ctggaagaag aactgaaacc gctggaagag gttctgaatg gcgcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc      417


<210> SEQ ID NO 20
<211> LENGTH: 134
<212> TYPE: PRT
<213> ORGANISM: Artificial Sequence
<220> FEATURE:
<223> OTHER INFORMATION: Synthetic Sequence_IL-2-09 amino acid sequence

<400> SEQUENCE: 20

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Ala Met Pro
        35                  40                  45

Lys Lys Ala Thr Glu Leu Lys His Leu Gln Cys Leu Glu Glu Glu Leu
```

```
    50                  55                  60

Lys Pro Leu Glu Glu Val Leu Asn Gly Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 21
<211> LENGTH: 417
<212> TYPE: DNA
<213> ORGANISM: Artificial Sequence
<220> FEATURE:
<223> OTHER INFORMATION: Synthetic Sequence_IL-2-10 nucleic acid
      sequence

<400> SEQUENCE: 21

catatggcac cgaccagcag cagcaccaaa aaaacccagc tgcaactgga acatctgctg      60

ttagatctgc aaatgattct gcagggcatc aacagctaca aaaatccgaa actgacccgt     120

atgctgaccg caaaattcta catgccgaaa aaagcaaccg agctgaaaca tctgcagtgt     180

ctggaagaag aactgaaacc gctggaagag gttctgaatg gcgcacagag caaaaacttt     240

catctgcgtc cgcgtgatct gattagcaat attaacgtta ttgtgctgga actgaaaggt     300

agcgaaacca cctttatgtg tgaatatgcc gatgaaaccg caaccattgt ggaatttctg     360

aatcgttgga ttacctttgc acagagcatt attagcaccc tgacctaatg aggatcc        417


<210> SEQ ID NO 22
<211> LENGTH: 134
<212> TYPE: PRT
<213> ORGANISM: Artificial Sequence
<220> FEATURE:
<223> OTHER INFORMATION: Synthetic Sequence_IL-2-10 amino acid sequence

<400> SEQUENCE: 22

Met Ala Pro Thr Ser Ser Ser Thr Lys Lys Thr Gln Leu Gln Leu Glu
1               5                   10                  15

His Leu Leu Leu Asp Leu Gln Met Ile Leu Gln Gly Ile Asn Ser Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Gly Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130
```

<210> SEQ ID NO 23
<211> LENGTH: 417
<212> TYPE: DNA
<213> ORGANISM: Artificial Sequence
<220> FEATURE:
<223> OTHER INFORMATION: Synthetic Sequence_IL-2-11 nucleic acid sequence

<400> SEQUENCE: 23

```
catatggcac cgaccagcag cagcaccaaa aaaacctgtc tgcaactgga acatctgctg     60

ttagatctgc aaatgattct gcagggcatc aacagctaca aaaatccgaa actgacccgt    120

atgctgaccg caaaattcta catgccgaaa aaagcaaccg agctgaaaca tctgcagtgt    180

ctggaagaag aactgaaacc gctggaagag gttctgaatg gcgcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcacct gtacctaatg aggatcc       417
```

<210> SEQ ID NO 24
<211> LENGTH: 134
<212> TYPE: PRT
<213> ORGANISM: Artificial Sequence
<220> FEATURE:
<223> OTHER INFORMATION: Synthetic Sequence_IL-2-11 amino acid sequence

<400> SEQUENCE: 24

```
Met Ala Pro Thr Ser Ser Ser Thr Lys Lys Thr Cys Leu Gln Leu Glu
1               5                   10                  15

His Leu Leu Leu Asp Leu Gln Met Ile Leu Gln Gly Ile Asn Ser Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Gly Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Cys Thr
    130
```

<210> SEQ ID NO 25
<211> LENGTH: 417
<212> TYPE: DNA
<213> ORGANISM: Artificial Sequence
<220> FEATURE:
<223> OTHER INFORMATION: Synthetic Sequence_IL-2-12 nucleic acid sequence

<400> SEQUENCE: 25

```
catatggcac cgaccagcag cagcaccaaa aaaacccagc tgcaactgga acatctgctg     60

ttagatctgc aaatgattct gcagggcatc aacagctaca aaaatccgaa actgacccgt    120

atgctgaccg caaaattcta catgccgaaa aaagcaaccg agctgaaaca tctgcagtgt    180
```

```
ctggaagaag aactgaaacc gctggaagag gtttgtaatg gcgcacagag caaaaacttt    240

catctgcgtt gtcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417


<210> SEQ ID NO 26
<211> LENGTH: 134
<212> TYPE: PRT
<213> ORGANISM: Artificial Sequence
<220> FEATURE:
<223> OTHER INFORMATION: Synthetic Sequence_IL-2-12 amino acid sequence

<400> SEQUENCE: 26

Met Ala Pro Thr Ser Ser Ser Thr Lys Lys Thr Gln Leu Gln Leu Glu
1               5                   10                  15

His Leu Leu Leu Asp Leu Gln Met Ile Leu Gln Gly Ile Asn Ser Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Cys Asn Gly Ala Gln Ser Lys Asn Phe His
65                  70                  75                  80

Leu Arg Cys Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 27
<211> LENGTH: 417
<212> TYPE: DNA
<213> ORGANISM: Artificial Sequence
<220> FEATURE:
<223> OTHER INFORMATION: Synthetic Sequence_IL-2-13 nucleic acid
      sequence

<400> SEQUENCE: 27

catatggcac cgaccagcag cagcaccaaa aaaacccagc tgcaactgga acatctgctg     60

ttagatctgc aaatgattct gcagtgtatc aacagctaca aaaatccgaa actgacccgt    120

atgctgaccg caaaattcta catgccgaaa aaagcaaccg agctgaaaca tctgcagtgt    180

ctggaagaag aactgaaacc gctggaagag gttctgaatg gcgcacagag caaaaactgt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417


<210> SEQ ID NO 28
<211> LENGTH: 134
<212> TYPE: PRT
<213> ORGANISM: Artificial Sequence
<220> FEATURE:
<223> OTHER INFORMATION: Synthetic Sequence_IL-2-13 amino acid sequence

<400> SEQUENCE: 28
```

```
Met Ala Pro Thr Ser Ser Ser Thr Lys Lys Thr Gln Leu Gln Leu Glu
1               5                   10                  15

His Leu Leu Leu Asp Leu Gln Met Ile Leu Gln Cys Ile Asn Ser Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Gly Ala Gln Ser Lys Asn Cys His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 29
<211> LENGTH: 417
<212> TYPE: DNA
<213> ORGANISM: Artificial Sequence
<220> FEATURE:
<223> OTHER INFORMATION: Synthetic Sequence_IL-2-14 nucleic acid
      sequence

<400> SEQUENCE: 29

catatggcac cgaccagcag cagcaccaaa aaaacccagc tgcaactgga acatctgctg     60

ttagatctgc aaatgattct gaacggcatc agcaactaca aaaatccgaa actgacccgt    120

atgctgaccg caaaattcta catgccgaaa aaagcaaccg agctgaaaca tctgcagtgt    180

ctggaagaag aactgaaacc gctggaagag gttctgaatg gcgcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417


<210> SEQ ID NO 30
<211> LENGTH: 134
<212> TYPE: PRT
<213> ORGANISM: Artificial Sequence
<220> FEATURE:
<223> OTHER INFORMATION: Synthetic Sequence_IL-2-14 amino acid sequence

<400> SEQUENCE: 30

Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Ser Asn Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Gly Ala Gln Ser Lys Asn Phe His
65                  70                  75                  80

Leu Arg Pro Arg Asp Leu Ile Ser Asn Ile Asn Val Ile Val Leu Glu
```

```
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 31
<211> LENGTH: 417
<212> TYPE: DNA
<213> ORGANISM: Artificial Sequence
<220> FEATURE:
<223> OTHER INFORMATION: Synthetic Sequence_IL-2-21 nucleic acid
      sequence

<400> SEQUENCE: 31

catatggcac cgaccagcag cagcaccaaa aaaacccagc tgcaactgga acatctgctg     60

ttagatctgc aaatgattct gcagggcatc agcaactaca aaaatccgaa actgacccgt    120

atgctgaccg caaaattcta catgccgaaa aaagcaaccg agctgaaaca tctgcagtgt    180

ctggaagaag aactgaaacc gctggaagag gttctgaatg gcgcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417


<210> SEQ ID NO 32
<211> LENGTH: 134
<212> TYPE: PRT
<213> ORGANISM: Artificial Sequence
<220> FEATURE:
<223> OTHER INFORMATION: Synthetic Sequence_IL-2-21 amino acid sequence

<400> SEQUENCE: 32

Met Ala Pro Thr Ser Ser Ser Thr Lys Lys Thr Gln Leu Gln Leu Glu
1               5                   10                  15

His Leu Leu Leu Asp Leu Gln Met Ile Leu Gln Gly Ile Ser Asn Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Gly Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130


<210> SEQ ID NO 33
<211> LENGTH: 417
<212> TYPE: DNA
<213> ORGANISM: Artificial Sequence
<220> FEATURE:
```

<223> OTHER INFORMATION: Synthetic Sequence_IL-2-22 nucleic acid sequence

<400> SEQUENCE: 33

```
catatggcac cgaccagcag cagcaccaaa aaaacccagc tgcaactgga acatctgctg     60

ttagatctgc aaatgattct gcagggcatc agcaactaca aaaatccgaa actgacccgt    120

atgctgaccg caaaattcta catgccgaaa aaagcaaccg agctgaaaca tctgcagtgt    180

ctggaagaag aactgaaacc gctggaagag gttctgcagg gcgcacagag caaaaacttt    240

catctgcgtc cgcgtgatct gattagcaat attaacgtta ttgtgctgga actgaaaggt    300

agcgaaacca cctttatgtg tgaatatgcc gatgaaaccg caaccattgt ggaatttctg    360

aatcgttgga ttacctttgc acagagcatt attagcaccc tgacctaatg aggatcc       417
```

<210> SEQ ID NO 34
<211> LENGTH: 134
<212> TYPE: PRT
<213> ORGANISM: Artificial Sequence
<220> FEATURE:
<223> OTHER INFORMATION: Synthetic Sequence_IL-2-22 amino acid sequence

<400> SEQUENCE: 34

```
Met Ala Pro Thr Ser Ser Ser Thr Lys Lys Thr Gln Leu Gln Leu Glu
1               5                   10                  15

His Leu Leu Leu Asp Leu Gln Met Ile Leu Gln Gly Ile Ser Asn Tyr
            20                  25                  30

Lys Asn Pro Lys Leu Thr Arg Met Leu Thr Ala Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Gln Gly Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130
```

<210> SEQ ID NO 35
<211> LENGTH: 396
<212> TYPE: DNA
<213> ORGANISM: Artificial Sequence
<220> FEATURE:
<223> OTHER INFORMATION: Synthetic Sequence_IL-2-23 nucleic acid sequence

<400> SEQUENCE: 35

```
catatggcac cgaccagcag cagcaccaaa aaaacctgtc tgcaactgga acatctgctg     60

ttagatctgc aaatgattct gaacggcatc cagagcatgc atattgatgc aaccctgtac    120

atgccgaaaa aagcaaccga gctgaaacat ctgcagtgtc tggaagaaga actgaaaccg    180

ctggaagagg ttctgaatct ggcacagagc aaaaactttc atctgcgtcc gcgtgatctg    240

attagcaata ttaacgttat tgtgctggaa ctgaaaggta gcgaaaccac ctttatgtgt    300

gaatatgccg atgaaaccgc aaccattgtg gaatttctga atcgttggat tacctttgca    360
```

```
cagagcatta ttagcacctg tacctaatga ggatcc                               396


<210> SEQ ID NO 36
<211> LENGTH: 127
<212> TYPE: PRT
<213> ORGANISM: Artificial Sequence
<220> FEATURE:
<223> OTHER INFORMATION: Synthetic Sequence_IL-2-23 amino acid sequence

<400> SEQUENCE: 36

Met Ala Pro Thr Ser Ser Ser Thr Lys Lys Thr Cys Leu Gln Leu Glu
1               5                   10                  15

His Leu Leu Leu Asp Leu Gln Met Ile Leu Asn Gly Ile Gln Ser Met
            20                  25                  30

His Ile Asp Ala Thr Leu Tyr Met Pro Lys Lys Ala Thr Glu Leu Lys
        35                  40                  45

His Leu Gln Cys Leu Glu Glu Glu Leu Lys Pro Leu Glu Glu Val Leu
    50                  55                  60

Asn Leu Ala Gln Ser Lys Asn Phe His Leu Arg Pro Arg Asp Leu Ile
65                  70                  75                  80

Ser Asn Ile Asn Val Ile Val Leu Glu Leu Lys Gly Ser Glu Thr Thr
                85                  90                  95

Phe Met Cys Glu Tyr Ala Asp Glu Thr Ala Thr Ile Val Glu Phe Leu
            100                 105                 110

Asn Arg Trp Ile Thr Phe Ala Gln Ser Ile Ile Ser Thr Cys Thr
        115                 120                 125


<210> SEQ ID NO 37
<211> LENGTH: 198
<212> TYPE: PRT
<213> ORGANISM: Artificial Sequence
<220> FEATURE:
<223> OTHER INFORMATION: Synthetic Sequence_IL-2R alpha (His tag)

<400> SEQUENCE: 37

Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175
```

```
Lys Pro Gln Ala Ser Pro Glu Gly Arg Pro Glu Ser Glu Thr Ser Cys
            180                 185                 190

His His His His His His
        195


<210> SEQ ID NO 38
<211> LENGTH: 466
<212> TYPE: PRT
<213> ORGANISM: Artificial Sequence
<220> FEATURE:
<223> OTHER INFORMATION: Synthetic Sequence_IL-2R beta (Fc hole)

<400> SEQUENCE: 38

Met Asp Met Arg Val Pro Ala Gln Leu Leu Gly Leu Leu Leu Leu Trp
1               5                   10                  15

Phe Pro Gly Ala Arg Cys Ala Val Asn Gly Thr Ser Gln Phe Thr Cys
            20                  25                  30

Phe Tyr Asn Ser Arg Ala Asn Ile Ser Cys Val Trp Ser Gln Asp Gly
        35                  40                  45

Ala Leu Gln Asp Thr Ser Cys Gln Val His Ala Trp Pro Asp Arg Arg
    50                  55                  60

Arg Trp Asn Gln Thr Cys Glu Leu Leu Pro Val Ser Gln Ala Ser Trp
65                  70                  75                  80

Ala Cys Asn Leu Ile Leu Gly Ala Pro Asp Ser Gln Lys Leu Thr Thr
                85                  90                  95

Val Asp Ile Val Thr Leu Arg Val Leu Cys Arg Glu Gly Val Arg Trp
            100                 105                 110

Arg Val Met Ala Ile Gln Asp Phe Lys Pro Phe Glu Asn Leu Arg Leu
        115                 120                 125

Met Ala Pro Ile Ser Leu Gln Val Val His Val Glu Thr His Arg Cys
    130                 135                 140

Asn Ile Ser Trp Glu Ile Ser Gln Ala Ser His Tyr Phe Glu Arg His
145                 150                 155                 160

Leu Glu Phe Glu Ala Arg Thr Leu Ser Pro Gly His Thr Trp Glu Glu
                165                 170                 175

Ala Pro Leu Leu Thr Leu Lys Gln Lys Gln Glu Trp Ile Cys Leu Glu
            180                 185                 190

Thr Leu Thr Pro Asp Thr Gln Tyr Glu Phe Gln Val Arg Val Lys Pro
        195                 200                 205

Leu Gln Gly Glu Phe Thr Thr Trp Ser Pro Trp Ser Gln Pro Leu Ala
    210                 215                 220

Phe Arg Thr Lys Pro Ala Ala Leu Gly Lys Asp Thr Gly Ala Gln Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335
```

```
Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Cys
        355                 360                 365

Thr Leu Pro Pro Ser Arg Asp Glu Leu Thr Lys Asn Gln Val Ser Leu
    370                 375                 380

Ser Cys Ala Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Val Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 39
<211> LENGTH: 492
<212> TYPE: PRT
<213> ORGANISM: Artificial Sequence
<220> FEATURE:
<223> OTHER INFORMATION: Synthetic Sequence_IL-2R gamma (Fc knob)

<400> SEQUENCE: 39

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220
```

```
Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255

Leu Phe Ala Leu Glu Ala Gly Ala Gln Asp Lys Thr His Thr Cys Pro
            260                 265                 270

Pro Cys Pro Ala Pro Glu Leu Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Cys Arg
385                 390                 395                 400

Asp Glu Leu Thr Lys Asn Gln Val Ser Leu Trp Cys Leu Val Lys Gly
                405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Lys
                485                 490


<210> SEQ ID NO 40
<211> LENGTH: 417
<212> TYPE: DNA
<213> ORGANISM: Artificial Sequence
<220> FEATURE:
<223> OTHER INFORMATION: Synthetic Sequence_IL-2-24 nucleic acid
      sequence

<400> SEQUENCE: 40

catatggcac cgaccagcag cagcaccaaa aaaacccagc tgcaactgga acatctgctg      60

ttagatctgc aaatgattct gcagggcatc agcaactaca aaaatccgaa actgacccgt     120

atgctgacct tcaaattcta catgccgaaa aaagcaaccg agctgaaaca tctgcagtgt     180

ctggaagaag aactgaaacc gctggaagag gttctgaatc tggcacagag caaaaacttt     240

catctgcgtc cgcgtgatct gattagccgt attaacgtta ttgtgctgga actgaaaggt     300

agcgaaacca cctttatgtg tgaatatgcc gatgaaaccg caaccattgt ggaatttctg     360

aatcgttgga ttacctttgc acagagcatt attagcaccc tgacctaatg aggatcc        417


<210> SEQ ID NO 41
<211> LENGTH: 134
```

-continued

```
<212> TYPE: PRT
<213> ORGANISM: Artificial Sequence
<220> FEATURE:
<223> OTHER INFORMATION: Synthetic Sequence_IL-2-24 amino acid sequence

<400> SEQUENCE: 41

Met Ala Pro Thr Ser Ser Ser Thr Lys Lys Thr Gln Leu Gln Leu Glu
1               5                   10                  15

His Leu Leu Leu Asp Leu Gln Met Ile Leu Gln Gly Ile Ser Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Arg Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ala Gln Ser
        115                 120                 125

Ile Ile Ser Thr Leu Thr
    130
```

HUMAN INTERLEUKIN-2 VARIANT OR DERIVATIVE THEREOF

CROSS-REFERENCE TO RELATED APPLICATIONS

The present application is the national stage of International Patent Application No. PCT/CN2019/126901, filed on Dec. 20, 2019, which claims the benefit of and priority to Chinese Application No. CN201811570930.5, filed on Dec. 21, 2018, and Chinese Patent Application No. CN201910158957.1, filed Mar. 4, 2019, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 21, 2018, is named "126268-5018-US_719086CUS_Sequence_Listing.TXT" and is 48 kilobytes in size.

FIELD OF THE INVENTION

The present disclosure relates to a human interleukin-2 (IL-2) variant or a derivative thereof having one or more amino acid mutation(s). Specifically, the human IL-2 variant or the derivative thereof has improved stability, and improved properties as an immunotherapeutic agent. The present disclosure also relates to an immunoconjugate comprising the human IL-2 variant or the derivative thereof, polynucleotide molecules encoding the same, vectors, host cells and preparation methods thereof, as well as relates to a pharmaceutical composition comprising the IL-2 variant or the derivative thereof or immunoconjugate, and also relates to the treatment method and pharmaceutical use thereof.

BACKGROUND OF THE INVENTION

Human interleukin-2 (IL-2), also known as T cell growth factor (TCGF), consists of 133 amino acids, with a molecular weight of approximately 15 kD, and the gene is located on chromosome 4 (4q27), including a sequence of 7 kb in total. In 1976 and 1977, Doris Morgan, Francis Ruscetti, Robert Gallo and Steven Gillis, Kendal Smith, et al respectively found that activated T cell culture medium can promote T cell proliferation. Afterwards, the stimulatory factor comprised in the culture medium was purified and identified as a single protein, namely IL-2.

Early experiments in cells in vitro showed that T cells can secrete IL-2 and express IL-2 receptor (IL-2R) on cell surface, once they are activated by TCR and CD28. The binding of IL-2 to its receptor can trigger the proliferation of T cells and make T cells have functions. This model makes IL-2 a molecule that plays a central role in the T cell immune response. However, it was found in subsequent in vivo experiments that animals would develop autoimmunity, when IL-2 or its receptor is knocked out. Subsequent experiments showed that IL-2 can not only activate effector cells (such as T cells and NK cells), but also activate regulatory T cells (Treg), thereby suppressing excessive autoimmunity.

IL-2 acts through IL-2R. IL-2R comprises three subunits: IL-2Rα (i.e. CD25), IL-2Rβ (i.e. CD122) and IL-2Rγ (i.e. CD132). The three subunits can form three forms of receptor: the high-binding affinity receptor comprises all the three subunits IL-2Rα/B/Y, the medium-binding affinity receptor comprises IL-2Rβ/γ, and the low-binding affinity receptor is IL-2Rα. Among them, IL-2Rβ and IL-2Rγ are necessary for IL-2 to activate downstream signaling pathways. Once IL-2 binds to both IL-2Rβ and IL-2Rγ, the two receptor subunits form a heterodimer, which in turn phosphorylates intracellular STAT5 and enters the nucleus to cause the corresponding transcription and expression of gene. IL-2Rα is not necessary for signal transduction, but can promote the binding of IL-2 to IL-2Rβ and IL-2Rγ. IL-2Rγ is expressed in all immune cells; IL-2Rβ is expressed in CD8+ T cells, NK cells, and Tregs, and the expression level of IL-2Rβ will be increased when T cells are activated; IL-2Rα is highly expressed in Tregs constantly, and transiently expressed in the activated CD8+ T cells, and then the expression level will be down-regulated.

IL-2 is mainly synthesized by the activated T cells, especially CD4+ helper T cells. IL-2 stimulates the proliferation and differentiation of T cells, induces the generation of cytotoxic T lymphocytes (CTL) and the differentiation of peripheral blood lymphocytes into cytotoxic cells and lymphocyte factor-activated killer (LAK) cells, promotes expression of cytokines and cytolysis molecules by T cells, promotes the proliferation and differentiation of B cells, and the synthesis of immunoglobulin through B cells, as well as stimulates the production, proliferation and activation of natural killer (NK) cells.

The ability of IL-2 to expand the population of lymphocytes in vivo and to improve the effector functions of these cells confers IL-2 with anti-tumor effects. IL-2 immunotherapy becomes a therapeutic option for patients having certain metastatic cancers. At present, high-dose of IL-2 has been approved for the treatment of metastatic renal cell carcinoma and malignant melanoma.

The existing studies on IL-2 variants have shown that IL-2 variants with mutations at at-least four positions of 38, 42, 45, 62, and 68 have a reduced stimulating effect on Tregs (WO2012062228); IL-2 variants having mutations at positions 72, 42, and 45 reduce or eliminate the binding affinity to the high-binding affinity IL-2 receptor, but still retain the binding affinity to the medium-binding affinity IL-2 receptor (CN201280017730.1); the mutations at positions 91 and 126 enable IL-2 to bind to CD25 (IL2Rα), but does not activate IL-2R on Tregs (U.S. Pat. No. 8,906,356); The IL-2Rs having at least one mutation of E15, H16, Q22, D84, N88 or E95, are used to treat graft-versus-host disease in subjects (U.S. Pat. No. 9,732,134); IL-2 variants comprising at least R38W can reduce vascular permeability, and can be used to treat solid tumors (U.S. Pat. Nos. 7,371,371; 7,514,073; 8,124,066; 7,803,361); fusion protein formed by IL-2 variant fusing to Fc is used to treat disease, the IL-2 has N88R mutation (WO2016014428); hIL-2-N88R can selectively activate T cells instead of natural killer cells, and can reduce the formation of metastasis in lung (WO 99/60128); IL-2 having mutation(s) at position 20, 88 or 126 can be used to prepare a medicament for the treatment and/or prevention of autoimmune disease (WO2009135615); a chimeric polypeptide, comprising a cytokine linked to ligand targeting a protein on immune cell surface, wherein the cytokine can be a variant of IL-2 (WO2017136818), etc.

However, there is still a need in this field for IL-2 variants with higher stability. There is an urgent problem in this field to providing such IL-2 variants and the derivatives thereof to enhance the therapeutic effectiveness of IL-2.

SUMMARY OF THE INVENTION

The present disclosure provides an IL-2 variant or a derivative thereof having one or more amino acid mutation (s), and a conjugate of the IL-2 variant or the derivative thereof, a coding polypeptide and nucleic acid molecule, a vector, host cell, pharmaceutical composition, pharmaceutical use and treatment method thereof.

In the first aspect, the present disclosure provides an IL-2 variant or a derivative thereof, which has one or more amino acid mutation(s) at the position(s) 11, 26, 27, 29, 30, 31, 32, 33, 34, 35, 36, 37, 38, 39, 40, 41, 42, 43, 44, 70, 71, 72, 78, 82, 88, 132. In the present disclosure, the mutation is represented in a form of abc, wherein a is the type of amino acid before mutation, b is the position of mutation, and c is the type of amino acid after mutation. For example, N26S refers to a mutation from asparagine (N) into serine(S) at position 26; N26 refers to that asparagine (N) at position 26 is mutated; 26S refers to that the amino acid at position 26 is mutated into serine(S).

Specifically, the IL-2 variant or the derivative thereof provided by the present disclosure comprises one or more amino acid mutation(s) or any combination thereof at the following positions: 26, 29, 30, 71, 11, 132, 70, 82, 27, and 78. In some embodiments, the amino acids before mutation (e.g. in wild type human IL-2) are: asparagine (N) at position 26, asparagine (N) at position 29, asparagine (N) at position 30, asparagine (N) at position 71, glutamine (Q) at position 11, leucine (L) at position 132, leucine (L) at position 70, proline (P) at position 82, glycine (G) at position 27, and phenylalanine (F) at position 78. In some embodiments, the amino acid mutation(s) of the IL-2 variant or the derivative thereof is/are any one or any combination selected from the following mutations: mutation into Gln (Q) at position 26, mutation into Serine(S) at position 29, mutation into Ser(S) at position 30, mutation into Gln (Q) at position 71, mutation into Cys (C) at position 11, 132, 70, 82, 27, or 78.

In some specific embodiments, the IL-2 variant or the derivative thereof comprises a first type of mutation, and the first type of mutation is any one selected from the group consisting of (1) to (7) or the combination thereof:

(1) N26Q,
(2) N29S,
(3) N30S,
(4) N71Q,
(5) Q11C and L132C,
(6) L70C and P82C, and
(7) G27C and F78C.

In some specific embodiments, the IL-2 variant or the derivative thereof described above has increased stability, for example, increased deamination stability and/or thermal stability; specifically, the first type of mutation provided by the present disclosure confers increased stability to the IL-2 variant or the derivative thereof, when compared to wild type IL-2; the stability comprises, but is not limited to, increased deamination stability and/or thermal stability.

On the other hand, the IL-2 variant or the derivative thereof provided by the present disclosure further comprises one or more amino acid mutation(s) at the following positions or the combination thereof: 29, 30, 31, 32, 33, 34, 35, 36, 37, 38, 39, 40, 41, 42, 43, 44, 45 and 72. In some embodiments, the amino acids before mutation (for example in wild type human IL-2) are: asparagine (N) at position 29, asparagine (N) at position 30, tyrosine (Y) at position 31, lysine (K) at position 32, asparagine (N) at position 33, proline (P) at position 34, lysine (K) at position 35, leucine (L) at position 36, threonine (T) at position 37, arginine (R) at position 38, methionine (M) at position 39, leucine (L) at position 40, threonine (T) at position 41, phenylalanine (F) at position 42, lysine (K) at position 43, phenylalanine (F) at position 44, tyrosine (Y) at position 45, leucine (L) at position 72.

In some specific embodiments, the IL-2 variant or the derivative thereof further comprises a second type of mutation, and the second type of mutation is any one selected from the group consisting of (8) to (11), or any combination of (8) to (10):

(8) F42A,
(9) Y45A,
(10) L72G, and
(11) NNYKNPKLTRMLTFK at positions 29-44 mutated into QSMHIDATL.

In some embodiments, the second type of mutation can eliminate or reduce the affinity of IL-2 for high-affinity receptor (IL-2Rα/β/γ), and retain affinity of IL-2 for medium-affinity receptor (IL-2Rβ/γ) affinity; the second type of mutation can retain the effect of IL-2 on inducing the proliferation and activation of effector cells (such as NK and T cells), but reduce the effect of IL-2 on inducing the proliferation and activation of Treg cells.

In the third aspect, the IL-2 variant or the derivative thereof provided by the present disclosure comprises one or more amino acid mutation(s) or any combination thereof on the following positions: 20, 88, and 126. In some embodiments, the amino acids before mutation (for example, in wild type human IL-2) are: aspartic acid (D) at position 20, asparagine (N) at position 88, and glutamine (Q) at position 126. In some embodiments, the IL-2 variant or the derivative thereof comprises any amino acid of the following or any combination thereof after mutation: alanine (A) or histidine (H) or isoleucine (I) or methionine (M) or glutamic acid (E) or serine(S) or valine (V) or tryptophan (W) at position 20; alanine (A) or arginine (R) or glutamic acid (E) or leucine (L) or phenylalanine (F) or glycine (G) or isoleucine (I) or methionine (M) or serine(S) or Y or valine (V) at position 88; asparagine (N) or leucine (L) or P or phenylalanine (F) or glycine (G) or isoleucine (I) or methionine (M) or arginine (R) or serine(S) or threonine (T) or tyrosine (Y) or valine (V) at position 126.

In some specific embodiments, the IL-2 variant or the derivative thereof further comprises the third type of mutation, which is any mutation selected from the group consisting of (12) to (14) or the combination thereof:

(12) N88 mutated into A, R, E, L, F, G, I, M, S, Y, V or D,
(13) D20 mutated into A, H, I, M, E, S, V, W or Y, (2)
(14) Q126 mutated into N, L, P, F, G, I, M, R, S, T, Y or V.

In some embodiments, the third type of mutation can reduce the affinity of IL-2 to both high-affinity receptor (IL-2Rα/β/γ) and medium-affinity receptor (IL-2Rβ/γ), and the affinity to high-affinity receptor is reduced more than that to medium-affinity receptor; the third type of mutation can retain the effect of IL-2 on inducing the proliferation and activation of Tregs, but eliminate or reduce the effect of IL-2 on inducing the proliferation and activation of effector cells (such as NK and T cells).

In some embodiments, the IL-2 variant or the derivative thereof comprises the first type of mutation and the second type of mutation, or comprises the first type of mutation and the third type of mutation, as described above.

In some embodiments, the first type of mutation in the IL-2 variant or the derivative thereof is selected from any one of (15) to (17), or is any one of (15) to (17) in combination with any of (5) to (7), as described above:

(15) N26Q and N29S,
(16) N26Q, N29S and N71Q, and
(17) N26Q and N30S;

The second type of mutation is selected from any one of (18) to (20) and (11):

(18) F42A and Y45A,
(19) F42A and L72G, and
(20) Y45A and L72G;

The third type of mutation is N88R or N88G or N88I or N88D.

In some embodiments, the IL-2 variant or the derivative thereof comprises mutations as shown in any one of (21) to (29):

(21) N26Q, N29S, F42A, N71Q and L72G,
(22) N26Q, N29S and N88R,
(23) N26Q, N29S, F42A and L72G,
(24) N26Q, N30S, F42A and L72G,
(25) Q11C, N26Q, N30S, F42A, L72G and L132C,
(26) N26Q, N30S, F42A, L70C, L72G and P82C,
(27) N26Q, G27C, N30S, F42A, L72G and F78C,
(28) N29S, F42A and L72G, and
(29) Q11C, NNYKNPKLTRMLTFKF at positions 29-44 mutated into QSMHIDATL, and L132C.

In addition to (1) to (29) described above, the present disclosure further provides the following IL-2 variant, which comprises any combination of the mutation position(s) and mutation type(s) as shown in (1) to (20), comprising but not limited to the following (30) to (208):

(30) N26Q/Q11C/L132C;
(31) N26Q/L70C/P82C;
(32) N26Q/G27C/F78C;
(33) N26Q/NNYKNPKLTRMLTFKF at positions 29-44 mutated into QSMHIDATL;
(34) N26Q/F42A/Y45A;
(35) N26Q/F42A/L72G;
(36) N26Q/Y45A/L72G;
(37) N26Q/F42A/Y45A/L72G;
(38) Q11C/N30S/L132C;
(39) N30S/L70C/P82C;
(40) G27C/N30S/F78C;
(41) N30S/F42A/Y45A;
(42) N30S/F42A/L72G;
(43) N30S/Y45A/L72G;
(44) N30S/F42A/Y45A/L72G;
(45) N29S/N30S/F42A/L72G;
(46) Q11C/F42A/Y45A;
(47) Q11C/F42A/L72G/L132C;
(48) Q11C/Y45A/L72G/L132C;
(49) Q11C/F42A/Y45A/L72G/L132C;
(50) Q11C/N29S/F42A/L72G/L132C;
(51) NNYKNPKLTRMLTFKF at positions 29-44 mutated into QSMHIDATL/L70C/P82C;
(52) F42A/Y45A/L70C/P82C;
(53) F42A/L70C/L72G/P82C;
(54) Y45A/L70C/L72G/P82C;
(55) F42A/Y45A/L70C/L72G/P82C;
(56) N29S/F42A/L70C/L72G/P82C;
(57) G27C/NNYKNPKLTRMLTFKF at positions 29-44 mutated into QSMHIDATL/F78C;
(58) G27C/F42A/Y45A/F78C;
(59) G27C/F42A/L72G/F78C;
(60) G27C/Y45A/L72G/F78C;
(61) G27C/F42A/Y45A/L72G/F78C;
(62) G27C/N29S/F42A/L72G/F78C;
(63) NNYKNPKLTRMLTFKF at positions 29-44 mutated into QSMHIDATL/Y45A;
(64) NNYKNPKLTRMLTFKF at positions 29-44 mutated into QSMHIDATL/L72G;
(65) NNYKNPKLTRMLTFKF at positions 29-44 mutated into QSMHIDATL/Y45A/L72G;
(66) N26Q/N30S/Q11C/L132C;
(67) N26Q/N30S/L70C/P82C;
(68) N26Q/G27C/N30S/F78C;
(69) N26Q/N30S/F42A/Y45A;
(70) N26Q/N30S/F42A/L72G;
(71) N26Q/N30S/Y45A/L72G;
(72) N26Q/N30S/F42A/Y45A/L72G;
(73) N26Q/N29S/N30S/F42A/L72G;
(74) N26Q/N29S/N30S;
(75) N26Q/N29S/Q11C/L132C;
(76) N26Q/N29S/L70C/P82C;
(77) N26Q/N29S/G27C/F78C;
(78) N26Q/N29S/F42A/Y45A;
(79) N26Q/N29S/Y45A/L72G;
(80) N26Q/N29S/F42A/Y45A/L72G;
(81) Q11C/N29S/N30S/L132C;
(82) N29S/N30S/L70C/P82C;
(83) G27C/N29S/N30S/F78C;
(84) N29S/N30S/F42A/Y45A;
(85) N29S/N30S/F42A/L72G;
(86) N29S/N30S/Y45A/L72G;
(87) N29S/N30S/F42A/Y45A/L72G;
(88) Q11C/N29S/F42A/Y45A/L132C;
(89) Q11C/N29S/F42A/L72G/L132C;
(90) Q11C/N29S/Y45A/L72G/L132C;
(91) Q11C/N29S/F42A/Y45A/L72G/L132C;
(92) N29S/F42A/Y45A/L70C/P82C;
(93) N29S/F42A/L70C/L72G/P82C;
(94) N29S/Y45A/L70C/L72G/P82C;
(95) N29S/F42A/Y45A/L70C/L72G/P82C;
(96) G27C/N29S/F78C/F42A/Y45A;
(97) G27C/N29S/F78C/F42A/L72G;
(98) G27C/N29S/F78C/Y45A/L72G;
(99) G27C/N29S/F78C/F42A/Y45A/L72G;
(100) N29S/F42A/Y45A;
(101) N29S/F42A/L72G;
(102) N29S/Y45A/L72G;
(103) N29S/F42A/Y45A/L72G;
(104) Q11C/N29S/L132C;
(105) N29S/L70C/P82C;
(106) G27C/N29S/F78C;
(107) N29S/N30S;
(108) N26Q/N29S;
(109) N26Q/N71Q;
(110) N30S/N71Q;
(111) Q11C/N71Q/L132C;
(112) L70C/N71Q/P82C;
(113) G27C/N71Q/F78C;
(114) NNYKNPKLTRMLTFKF at positions 29-44 mutated into QSMHIDATL/N71Q;
(115) F42A/Y45A/N71Q;
(116) F42A/N71Q/L72G;
(117) Y45A/N71Q/L72G;
(118) N26Q/N30S/F42A/N71Q/L72G;
(119) Q11C/N26Q/N30S/F42A/N71Q/L72G/L132C;
(120) N26Q/N30S/F42A/L70C/N71Q/L72G/P82C;
(121) N26Q/G27C/N30S/F42A/N71Q/L72G/F78C;
(122) N29S/F42A/N71Q/L72G;
(123) N26Q/N30S/N71Q;
(124) N26Q/Q11C/N71Q/L132C;
(125) N26Q/L70C/N71Q/P82C;
(126) N26Q/G27C/N71Q/F78C;

(127) N26Q/NNYKNPKLTRMLTFKF at positions 29-44 mutated into QSMHIDATL/N71Q;
(128) N26Q/F42A/Y45A/N71Q;
(129) N26Q/F42A/N71Q/L72G;
(130) N26Q/Y45A/N71Q/L72G;
(131) N26Q/F42A/Y45A/N71Q/L72G;
(132) Q11C/N30S/N71Q/L132C;
(133) N30S/L70C/N71Q/P82C;
(134) G27C/N30S/N71Q/F78C;
(135) N30S/F42A/Y45A/N71Q;
(136) N30S/F42A/N71Q/L72G;
(137) N30S/Y45A/N71Q/L72G;
(138) N30S/F42A/Y45A/N71Q/L72G;
(139) N29S/N30S/F42A/N71Q/L72G;
(140) Q11C/F42A/Y45A/N71Q;
(141) Q11C/F42A/N71Q/L72G/L132C;
(142) Q11C/Y45A/N71Q/L72G/L132C;
(143) Q11C/F42A/Y45A/N71Q/L72G/L132C;
(144) Q11C/N29S/F42A/N71Q/L72G/L132C;
(145) NNYKNPKLTRMLTFKF at positions 29-44 mutated into QSMHIDATL/L70C/N71Q/P82C;
(146) F42A/Y45A/L70C/N71Q/P82C;
(147) F42A/L70C/N71Q/L72G/P82C;
(148) Y45A/L70C/N71Q/L72G/P82C;
(149) F42A/Y45A/L70C/N71Q/L72G/P82C;
(150) N29S/F42A/L70C/N71Q/L72G/P82C;
(151) G27C/NNYKNPKLTRMLTFKF at positions 29-44 mutated into QSMHIDATL/N71Q/F78C;
(152) G27C/F42A/Y45A/N71Q/F78C;
(153) G27C/F42A/N71Q/L72G/F78C;
(154) G27C/Y45A/N71Q/L72G/F78C;
(155) G27C/F42A/Y45A/N71Q/L72G/F78C;
(156) G27C/N29S/F42A/N71Q/L72G/F78C;
(157) NNYKNPKLTRMLTFKF at positions 29-44 mutated into QSMHIDATL/Y45A/N71Q;
(158) NNYKNPKLTRMLTFKF at positions 29-44 mutated into QSMHIDATL/N71Q/L72G;
(159) NNYKNPKLTRMLTFKF at positions 29-44 mutated into QSMHIDATL/Y45A/N71Q/L72G;
(160) N26Q/N30S/Q11C/N71Q/L132C;
(161) N26Q/N30S/L70C/N71Q/P82C;
(162) N26Q/G27C/N30S/N71Q/F78C;
(163) N26Q/N30S/F42A/Y45A/N71Q;
(164) N26Q/N30S/F42A/N71Q/L72G;
(165) N26Q/N30S/Y45A/N71Q/L72G;
(166) N26Q/N30S/F42A/Y45A/N71Q/L72G;
(167) N26Q/N29S/N30S/F42A/N71Q/L72G;
(168) N26Q/N29S/N30S/N71Q;
(169) N26Q/N29S/Q11C/N71Q/L132C;
(170) N26Q/N29S/L70C/N71Q/P82C;
(171) N26Q/N29S/G27C/N71Q/F78C;
(172) N26Q/N29S/F42A/Y45A/N71Q;
(173) N26Q/N29S/Y45A/N71Q/L72G;
(174) N26Q/N29S/F42A/Y45A/N71Q/L72G;
(175) Q11C/N29S/N30S/N71Q/L132C;
(176) N29S/N30S/L70C/N71Q/P82C;
(177) G27C/N29S/N30S/N71Q/F78C;
(178) N29S/N30S/F42A/Y45A/N71Q;
(179) N29S/N30S/F42A/N71Q/L72G;
(180) N29S/N30S/Y45A/N71Q/L72G;
(181) N29S/N30S/F42A/Y45A/N71Q/L72G;
(182) Q11C/N29S/F42A/Y45A/N71Q/L132C;
(183) Q11C/N29S/F42A/N71Q/L72G/L132C;
(184) Q11C/N29S/Y45A/N71Q/L72G/L132C;
(185) Q11C/N29S/F42A/Y45A/N71Q/L72G/L132C;
(186) N29S/F42A/Y45A/L70C/N71Q/P82C;
(187) N29S/F42A/L70C/N71Q/L72G/P82C;
(188) N29S/Y45A/L70C/N71Q/L72G/P82C;
(189) N29S/F42A/Y45A/L70C/N71Q/L72G/P82C;
(190) G27C/N29S/F78C/F42A/Y45A/N71Q;
(191) G27C/N29S/F78C/F42A/N71Q/L72G;
(192) G27C/N29S/F78C/Y45A/N71Q/L72G;
(193) G27C/N29S/F78C/F42A/Y45A/N71Q/L72G;
(194) N29S/F42A/Y45A/N71Q;
(195) N29S/F42A/N71Q/L72G;
(196) N29S/Y45A/N71Q/L72G;
(197) N29S/F42A/Y45A/N71Q/L72G;
(198) Q11C/N29S/N71Q/L132C;
(199) N29S/L70C/N71Q/P82C;
(200) G27C/N29S/N71Q/F78C;
(201) N29S/N30S/N71Q;
(202) N26Q/N29S/N71Q;
(203) N26Q/N88R;
(204) N29S/N88R;
(205) N30S/N88R;
(206) N26Q/N88R/Q11C/L132C;
(207) N29S/N88R/L70C/P82C; and
(208) N30S/N88R/G27C/F78C; wherein, "/" refers to that the mutations are present at the same time in a single IL-2 variant. In some embodiments, the mutations described above are relative to wild type IL-2, and the amino acid sequence of the wild type IL-2 is shown in SEQ ID NO: 2. The numbering of mutation position is counted from amino acid A at the second position according to the amino acid sequence as shown in SEQ ID NO: 2.

In some embodiments, the IL-2 variant or the derivative thereof comprises amino acids as shown in any one selected from the group consisting of SEQ ID NO. 4, SEQ ID NO. 6, SEQ ID NO. 8, SEQ ID NO. 10, SEQ ID NO.12, SEQ ID NO.14, SEQ ID NO.16, SEQ ID NO.18, SEQ ID NO.20, SEQ ID NO.22, SEQ ID NO.24, SEQ ID NO.26, SEQ ID NO.28, SEQ ID NO. 30, SEQ ID NO. 32, SEQ ID NO. 34, SEQ ID NO. 36 and SEQ ID NO. 41. The amino acid sequences of the polypeptides and the corresponding nucleotide sequences are shown in Table 1 (the underline represents the amino acid mutation):

TABLE 1

The amino acid sequence and nucleic acid sequence of IL-2 variants

| Numbering | Mutation position | The amino acid sequences for wild type and the variants of human IL-2 | Corresponding SEQ ID NO. |
|---|---|---|---|
| IL-2-WT | wild type | MAPTSSSTKKTQLQLEHLLLDLQMILNG<br>INNYKNPKLTRMLTFKFYMPKKATELKH<br>LQCLEEELKPLEEVLNLAQSKNFHLRPR<br>DLISNINVIVLELKGSETTFMCEYADETA<br>TIVEFLNRWITFCQSIISTLT<br>(SEQ ID NO: 2) | SEQ ID NO: 1 |

TABLE 1-continued

The amino acid sequence and nucleic acid sequence of IL-2 variants

| Numbering | Mutation position | The amino acid sequences for wild type and the variants of human IL-2 | Corresponding SEQ ID NO. |
|---|---|---|---|
| IL-2-01 | N26Q | MAPTSSSTKKTQLQLEHLLLDLQMIL**Q**G INNYKNPKLTRMLTFKFYMPKKATELKH LQCLEEELKPLEEVLNLAQSKNFHLRPR DLISNINVIVLELKGSETTFMCEYADETA TIVEFLNRWITFAQSIISTLT (SEQ ID NO: 4) | SEQ ID NO: 3 |
| IL-2-02 | N30S | MAPTSSSTKKTQLQLEHLLLDLQMILNG IN**S**YKNPKLTRMLTFKFYMPKKATELKH LQCLEEELKPLEEVLNLAQSKNFHLRPR DLISNINVIVLELKGSETTFMCEYADETA TIVEFLNRWITFAQSIISTLT (SEQ ID NO: 6) | SEQ ID NO: 5 |
| IL-2-03 | Q11C/L132C | MAPTSSSTKKT**C**LQLEHLLLDLQMILNG INNYKNPKLTRMLTFKFYMPKKATELKH LQCLEEELKPLEEVLNLAQSKNFHLRPR DLISNINVIVLELKGSETTFMCEYADETA TIVEFLNRWITFAQSIIST**C**T (SEQ ID NO: 8) | SEQ ID NO: 7 |
| IL-2-04 | L70C/P82C | MAPTSSSTKKTQLQLEHLLLDLQMILNG INNYKNPKLTRMLTFKFYMPKKATELKH LQCLEEELKPLEEV**C**NLAQSKNFHLR**C**R DLISNINVIVLELKGSETTFMCEYADETA TIVEFLNRWITFAQSIISTLT (SEQ ID NO: 10) | SEQ ID NO: 9 |
| IL-2-05 | G27C/F78C | MAPTSSSTKKTQLQLEHLLLDLQMILN**C** INNYKNPKLTRMLTFKFYMPKKATELKH LQCLEEELKPLEEVLNLAQSKN**C**HLRPR DLISNINVIVLELKGSETTFMCEYADETA TIVEFLNRWITFAQSIISTLT (SEQ ID NO: 12) | SEQ ID NO: 11 |
| IL-2-06 | NNYKNPKLT RMLTFKF at positions 29-44 mutated into QSMHIDATL | MAPTSSSTKKTQLQLEHLLLDLQMILNG I**QSMHIDATL**YMPKKATELKHLQCLEEE LKPLEEVLNLAQSKNFHLRPRDLISNINV IVLELKGSETTFMCEYADETATIVEFLNR WITFAQSIISTLT (SEQ ID NO: 14) | SEQ ID NO: 13 |
| IL-2-07 | F42A/Y45A | MAPTSSSTKKTQLQLEHLLLDLQMILNG INNYKNPKLTRMLT**A**KF**A**MPKKATELK HLQCLEEELKPLEEVLNLAQSKNFHLRP RDLISNINVIVLELKGSETTFMCEYADET ATIVEFLNRWITFAQSIISTLT (SEQ ID NO: 16) | SEQ ID NO: 15 |
| IL-2-08 | F42A/L72G | MAPTSSSTKKTQLQLEHLLLDLQMILNG INNYKNPKLTRMLT**A**KFYMPKKATELK HLQCLEEELKPLEEVLN**G**AQSKNFHLRP RDLISNINVIVLELKGSETTFMCEYADET ATIVEFLNRWITFAQSIISTLT (SEQ ID NO: 18) | SEQ ID NO: 17 |
| IL-2-09 | Y45A/L72G | MAPTSSSTKKTQLQLEHLLLDLQMILNG INNYKNPKLTRMLTFKF**A**MPKKATELKH LQCLEEELKPLEEVLN**G**AQSKNFHLRPR DLISNINVIVLELKGSETTFMCEYADETA TIVEFLNRWITFAQSIISTLT (SEQ ID NO: 20) | SEQ ID NO: 19 |
| IL-2-10 | N26Q/N30S/ F42A/L72G | MAPTSSSTKKTQLQLEHLLLDLQMIL**Q**G INSYKNPKLTRMLT**A**KFYMPKKATELKH LQCLEEELKPLEEVLN**G**AQSKNFHLRPR DLISNINVIVLELKGSETTFMCEYADETA TIVEFLNRWITFAQSIISTLT (SEQ ID NO: 22) | SEQ ID NO: 21 |

TABLE 1-continued

The amino acid sequence and nucleic acid sequence of IL-2 variants

| Numbering | Mutation position | The amino acid sequences for wild type and the variants of human IL-2 | Corresponding SEQ ID NO. |
|---|---|---|---|
| IL-2-11 | Q11C/N26Q/ N30S/F42A/ L72G/L132C | MAPTSSSTKKT**C**LQLEHLLLDLQMIL**Q**G IN**S**YKNPKLTRMLT**A**KFYMPKKATELKH LQCLEEELKPLEEVL**NG**AQSKNFHLRPR DLISNINVIVLELKGSETTFMCEYADETA TIVEFLNRWITFAQSIIST**C**T (SEQ ID NO: 24) | SEQ ID NO: 23 |
| IL-2-12 | N26Q/N30S/ F42A/L70C/ L72G/P82C | MAPTSSSTKKTQLQLEHLLLDLQMIL**Q**G IN**S**YKNPKLTRMLT**A**KFYMPKKATELKH LQCLEEELKPLEEV**CNG**AQSKNFHLR**C**R DLISNINVIVLELKGSETTFMCEYADETA TIVEFLNRWITFAQSIISTLT (SEQ ID NO: 26) | SEQ ID NO: 25 |
| IL-2-13 | N26Q/G27C/ N30S/F42A/ L72G/F78C | MAPTSSSTKKTQLQLEHLLLDLQMIL**QC** IN**S**YKNPKLTRMLT**A**KFYMPKKATELKH LQCLEEELKPLEEVL**NG**AQSKN**C**HLRPR DLISNINVIVLELKGSETTFMCEYADETA TIVEFLNRWITFAQSIISTLT (SEQ ID NO: 28) | SEQ ID NO: 27 |
| IL-2-14 | N29S/F42A/ L72G | MAPTSSSTKKTQLQLEHLLLDLQMILNG I**S**NYKNPKLTRMLT**A**KFYMPKKATELKH LQCLEEELKPLEEVL**NG**AQSKNFHLRPR DLISNINVIVLELKGSETTFMCEYADETA TIVEFLNRWITFAQSIISTLT (SEQ ID NO: 30) | SEQ ID NO: 29 |
| IL-2-21 | N26Q/N29S/ F42A/L72G | MAPTSSSTKKTQLQLEHLLLDLQMIL**Q**G I**S**NYKNPKLTRMLT**A**KFYMPKKATELKH LQCLEEELKPLEEVL**NG**AQSKNFHLRPR DLISNINVIVLELKGSETTFMCEYADETA TIVEFLNRWITFAQSIISTLT (SEQ ID NO: 32) | SEQ ID NO: 31 |
| IL-2-22 | N26Q/N29S/ F42A/N71Q/ L72G | MAPTSSSTKKTQLQLEHLLLDLQMIL**Q**G I**S**NYKNPKLTRMLT**A**KFYMPKKATELKH LQCLEEELKPLEEVL**QG**AQSKNFHLRPR DLISNINVIVLELKGSETTFMCEYADETA TIVEFLNRWITFAQSIISTLT (SEQ ID NO: 34) | SEQ ID NO: 33 |
| IL-2-23 | NNYKNPKLT RMLTFKF at position Q11C/29-44 mutated into QSMHIDATL/ L132C | MAPTSSSTKKT**C**LQLEHLLLDLQMILNG I**QSMHIDATL**YMPKKATELKHLQCLEEE LKPLEEVLNLAQSKNFHLRPRDLISNINV IVLELKGSETTFMCEYADETATIVEFLNR WITFAQSIIST**C**T (SEQ ID NO: 36) | SEQ ID NO: 35 |
| IL-2-24 | N26Q/N29S/ N88R | MAPTSSSTKKTQLQLEHLLLDLQMIL**Q**G I**S**NYKNPKLTRMLTFKFYMPKKATELK HLQCLEEELKPLEEVLNLAQSKNFHLRP RDLIS**R**INVIVLELKGSETTFMCEYADET ATIVEFLNR WITFAQSIISTLT (SEQ ID NO.41) | SEQ ID NO: 40 |

(Note: The numbering for the mutation positions mentioned above is according to the mature human IL-2 protein as shown in SEQ ID NO: 2. The mature human IL-2 protein does not comprise the amino acid M at the first position, so the numbering starts from the amino acid A at second position. Among them, "/" refers to that the mutations are present at the same time in a single IL-2 variant. Each variant can comprise C125A or not; wherein the presence of C125A is to avoid the formation dimer).

In some embodiments, the derivative of the IL-2 variant includes the full-length or partial protein of the IL-2 variant in the present disclosure; or includes the mutated proteins, functional derivatives, functional fragments, biologically active peptides, fusion proteins, isoforms or the salts thereof obtained by further mutation on the basis of the IL-2 variant in present disclosure. For example, a fusion protein comprising the IL-2 variant, a monomer or dimer or trimer or polymer of the IL-2 variant, various modified forms of the IL-2 variant (such as PEGylation, pegylation, glycosylation, albumin-conjugation or fusion, Fc-fusion or conjugation, hydroxyethylation, absence of O-glycosylation, etc.), and homologues of the IL-2 variant in various species. The modification of IL-2 does not cause adverse effects on immunogenicity related to the treatment.

In some embodiments, the IL-2 variant or derivative thereof is PEGylated (which can be expressed as PEG-IL-2), for example, a mono- or di-PEGylated IL-2 variant or derivative thereof. The PEG-IL-2 variant or derivative thereof comprises an SC-PEG linking group. In other embodiments, the PEG-IL-2 variant or derivative thereof comprises a methoxy-PEG-aldehyde (mPEG-ALD) linking group. In certain embodiments, the average molecular weight of the PEG moiety ranges from about 5 KD to about 50 KD, in particular 5, 10, 11, 12, 13, 14, 15, 16, 17, 18, 19, 20, 21, 22, 23, 24, 25, 30, 35, 40, 45, 50 KD; or about 5 KD to about 40 KD, or about 10 KD to about 30 KD, or about 10 KD to about 30 KD, or about 15 KD to about 20 KD. In certain embodiments, the mPEG-ALD linking group comprises PEG molecule having an average molecular weight selected from the group consisting of about 5 KDa, about 12 KDa, and about 20 KDa. In some embodiments, the aldehyde group in mPEG-ALD may be acetaldehyde, propionaldehyde, butyraldehyde, or the like. In one embodiment, the IL-2 variant or the derivative thereof has an extended serum half-life, when compared to that of wild type IL-2 or the derivative thereof.

When the IL-2 variant or the derivative thereof comprises the second type of mutation, in some embodiments, the IL-2 variant or the derivative thereof can trigger one or more cellular response(s) selected from the group consisting of: proliferation of the activated T lymphocytes, differentiation of the activated T lymphocytes, activity of the cytotoxic T cells (CTLs), proliferation of the activated B cells, differentiation of the activated B cells, proliferation of the natural killer (NK) cells, differentiation of the NK cells, cytokine secretion by the activated T cells or NK cells, and anti-tumor cytotoxicity of the killer cells (LAK) activated by NK/lymphocyte. In some embodiments, the IL-2 variant or the derivative thereof has a reduced ability to induce IL-2 signaling in regulatory T cells, when compared to that of wild type IL-2 polypeptide. In one embodiment, the IL-2 variant or the derivative thereof induces less activation-induced cell death (AICD) in T cells than that of wild type IL-2 or the derivative thereof. In some specific embodiments, the IL-2 variant or the derivative thereof has reduced in vivo toxicity when compared to that of wild type IL-2 or derivative thereof.

When the IL-2 variant or the derivative thereof comprises the third type of mutation, in some embodiments, the IL-2 variant or the derivative thereof can reduce the affinity of IL-2 to both high-affinity receptor (IL-2Rα/β/γ) and the medium-affinity receptor (IL-2Rβ/γ), however the reduction of affinity to the high-affinity receptor is more than that to the medium-affinity receptor. In some embodiments, the IL-2 variant or the derivative thereof can retain the effect of IL-2 on inducing the proliferation and activation of Tregs, but eliminate or reduce the effect of IL-2 on inducing the proliferation and activation of effector cells (such as NK and T cells).

In another aspect, the present disclosure provides a conjugate in which the IL-2 variant or the derivative thereof is directly connected to or indirectly connected to a non-IL-2 module through a linker. In some embodiments, the conjugate is an immunoconjugate, wherein the non-IL-2 module is an antigen-binding module. In some embodiments, the antigen-binding module targets antigens present on tumor cells or in the environment of tumor cells.

In some embodiments, the IL-2 variant is linked to at least one non-IL-2 module. In some embodiments, the IL-2 variant and the non-IL-2 module form a fusion protein, which means that the IL-2 variant shares a peptide bond with the non-IL-2 module. In some embodiments, the IL-2 variant is linked to at least one non-IL-2 module, such as a first non-IL-2 module and a second non-IL-2 module. In some embodiments, the non-IL-2 module is an antigen-binding module. In some embodiments, the IL-2 variant shares a peptide bond with the first antigen-binding module at amino or carboxyl terminus, and the second antigen-binding module shares a peptide bond with the following at amino or carboxyl terminus: i) the IL-2 variant; or ii) the first antigen-binding module. In some specific embodiments, the IL-2 variant shares a peptide bond with the first non-IL-2 module at carboxyl terminus, and shares a peptide bond with the second non-IL-2 module at amino terminus. In some embodiments, the non-IL-2 module is an antigen-binding module. The antigen-binding module may be an antibody or an antigen-binding fragment, comprising but not limited to immunoglobulin molecules (for example, IgG (e.g., IgG1) immunoglobulin-like molecules), antibodies or antigen-binding fragments thereof. In some specific embodiments, the antibody or the antigen-binding fragment thereof is selected from: a polypeptide complex comprising an antibody heavy chain variable region and an antibody light chain variable region, Fab, Fv, sFv, F(ab')2, linear antibody, single chain antibody, scFv, sdAb, sdFv, nanobody, peptide antibody peptibody, domain antibody and multispecific antibody (bispecific antibody, diabody, triabody and tetrabody, tandem two-scFv, tandem three-scFv). In the case where the IL-2 variant is connected to more than one antigen-binding modules (such as to the first and second antigen-binding module), each antigen-binding module can be independently selected from various forms of antibodies and antigen-binding fragments, for example, the first antigen-binding module may be a Fab molecule, and the second antigen-binding module may be a scFv molecule, or each of the first and second antigen-binding modules is scFv molecule, or each of the first and second antigen-binding modules is Fab molecule. In some embodiments, in the case where the IL-2 variant is connected to more than one antigen-binding modules (such as to the first and second antigen-binding module), the antigen targeted by each antigen-binding module can be independently selected, for example, the first and the second antigen-binding module are directed against different antigens or directed against the same antigen.

In some embodiments, the antigen bound by the antigen-binding module may be selected from the group consisting of: A1 domain of tenascin C (TNC A1), A2 domain of tenascin C (TNC A2), the extradomain of fibronectin (Extra Domain B) (EDB), carcinoembryonic antigen (CEA) and melanoma-associated chondroitin sulfate proteoglycan (MCSP). In some embodiments, tumor antigens comprise but are not limited to MAGE, MART-1/Melan-A, gp100, dipeptidyl peptidase IV (DPPIV), adenosine deaminase binding protein (ADAbp), cyclophilin b, colorectum related antigen (CRC)-C017-1A/GA733, carcinoembryonic antigen (CEA) and its immunogenic epitopes CAP-1 and CAP-2, etv6, aml1, prostate specific antigen (PSA) and its immunogenic epitopes PSA-1, PSA-2 and PSA-3, prostate-specific membrane antigen (PSMA), T cell receptor/CD3-zeta chain, MAGE family of tumor antigens (such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE family of tumor antigens (e.g. GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, P120ctn, gp100Pmel117, PRAME, NY-ESO-1, cdc27, adenomatous polyposis coli protein (APC), fodrin, connexin 37, Ig idiotype, p15, gp75, GM2 and GD2 gangliosides, viral products (such as human papilloma virus protein), Smad family of tumor antigens, lmp-1, PIA, EBV-encoded nuclear antigen (EBNA)-1, brain glycogen phosphorylase, SSX-1, SSX-2 (HOM-MEL-40), SSX-1, SSX-4, SSX-5, SCP-1 and CT-7 and c-erbB-2. In some embodiments, non-limiting examples of viral antigens involve influenza virus hemagglutinin, Epstein-Barr virus LMP-1, hepatitis C virus E2 glycoprotein, HIV gp160, and HIV gp120. In some embodiments, non-limiting examples of ECM antigens involve syndecan, heparanase, integrin, osteopontin, link, cadherin, laminin, EGF-type laminin, lectin, fibronectin, notch, tenascin and matrixin.

In some embodiments, the IL-2 variant or the derivative thereof comprising the antigen-binding module described above, comprises the second type of mutation, but does not comprise the third type of mutation.

In some embodiments, a method for increasing the stability of the IL-2 or the derivative or conjugate thereof is provided, the method comprises introducing mutation(s) into the IL-2 or the derivative or the conjugate thereof, wherein said mutation(s) is/are any one of 1) to 7) or the combination thereof:

1) N26Q,
2) N29S,
3) N30S,
4) N71Q,
5) Q11C and L132C,
6) L70C and P82C, and
7) G27C and F78C.

In another aspect, the present disclosure provides a pharmaceutical composition, which comprises the IL-2 variant or the derivative thereof or immunoconjugate described above, optionally comprises a pharmaceutically acceptable diluent, carrier or auxiliary. The pharmaceutical composition may be a lyophilized preparation or an injectable solution.

In some specific embodiments, the pharmaceutical composition may comprise 0.01 to 99% by weight of the IL-2 variant or the derivative thereof or the immunoconjugate in a unit dose; or the amount of the IL-2 variant or the derivative thereof or the immunoconjugate comprised in unit does of the pharmaceutical composition is 0.1-2000 mg (e.g. 1-1000 mg).

In another aspect, the present disclosure provides a nucleic acid encoding the IL-2 variant or the derivative thereof described above. The nucleic acid comprises a polynucleotide shown in any one selected from the group consisting of SEQ ID NO. 3, SEQ ID NO. 5, SEQ ID NO. 7, SEQ ID NO. 9, SEQ ID NO. 11, SEQ ID NO. 13, SEQ ID NO. 15, SEQ ID NO.17, SEQ ID NO.19, SEQ ID NO.21, SEQ ID NO.23, SEQ ID NO.25, SEQ ID NO.27, SEQ ID NO.29, SEQ ID NO.31, SEQ ID NO. 33, SEQ ID NO. 35, and SEQ ID NO. 40.

In some embodiments, an expression vector comprising a nucleic acid encoding the IL-2 variant or the derivative thereof described above is provided.

In another aspect, a host cell expressing the vector described above is provided. The host cell may be a prokaryotic or a eukaryotic cell. In some specific embodiments, the host cell is a bacterium, yeast or mammalian cell; specifically *Pichia pastoris* or *Saccharomyces cerevisiae*.

In some embodiments, the host cell comprises (for example, has been transformed or transfected with) a vector comprising a polynucleotide encoding the amino acid sequence of the IL-2 variant or the derivative thereof, or immunoconjugate described above. The host cell involves prokaryotic microorganism (such as *Escherichia coli*) or various eukaryotic cells (such as Chinese hamster ovary cells (CHO), human embryonic kidney (HEK) cells or lymphocytes (such as Y0, NS0, Sp20 cells), insect cells, etc.). In some embodiments, host cells expressing glycosylated polypeptides can be used, which are derived from multicellular organisms (for example, invertebrates and vertebrates), such as plant and insect cells. Vertebrate cells can also be used as host cells, for example, mammalian cell lines maintained in suspension, monkey kidney CV1 lines (COS-7), human embryonic kidney lines (293 or 293T cells), baby hamster kidney cells (BHK), mouse sertoli cells (TM4 cells), monkey kidney cells (CV1), african green monkey kidney cells (VERO-76), human cervical cancer cells (HELA), canine kidney cells (MDCK), buffalo rat hepatocytes (BRL3A), human lung cells (W138), human hepatocytes (Hep G2), mouse breast tumor cells (MMT060562), TRI cells (for examples, those described in Mather et al., Annals N.Y. Acad Sci 383, 44-68 (1982)), MRC5 cells and FS4 cells, Chinese Hamster Ovary (CHO) cells, myeloma cell lines such as YO, NS0, P3X63 and Sp2/0, and cells comprised in transgenic animals, transgenic plants or cultivated plants or animal tissues.

In another aspect, the present disclosure provides use of the IL-2 variant or the derivative thereof, the immunoconjugate or pharmaceutical composition comprising the same described above for the preparation of a medicament.

The IL-2 variant or the derivative thereof will be used to treat proliferative disease, immune disease, to regulate T cell-mediated immune response, to stimulate immune system in an individual, and to be used for the preparation of a relative medicament, when it comprises the second type of mutation. The proliferative disease may be tumor or cancer (for example, metastatic tumor or cancer), and may be solid tumor (for example, metastatic renal cell carcinoma and malignant melanoma). In some embodiments, the IL-2 variant or the derivative thereof or immunoconjugate thereof of the present disclosure can be used to treat diseases or conditions that will benefit from the stimulation of the immune system in a host, especially conditions where enhanced cellular immune response is desired; such conditions involve insufficient or defective immune response of the host. In some embodiments, the diseases or conditions for which the IL-2 variant or the derivative thereof or immunoconjugate thereof shall be administered refer to tumors or infections, wherein cellular immune response is the key mechanism of specific immunity for those tumors or infections, such as cancer (e.g., renal cell carcinoma or melanoma), immunodeficiency (such as HIV-positive patients, immunosuppressed patients), chronic infections, etc. In some embodiments, the enhanced cellular immune response may comprise any one or more of the following: general increase in immune function, increase in T cell function, increase in B cell function, recovery of lymphocyte function, increased expression of IL-2 receptor, increased T cell responses, increased activity of natural killer cells or increased activity of lymphokine activated killer cells (LAK), etc. In some embodiments, the disease that is treated by the IL-2 variant or the derivative thereof or immunoconjugate thereof of the present disclosure is a proliferative disorder, such as cancer. Non-limiting examples of cancers comprise bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, cutaneous cancer, squamous cell cancer, bone cancer and kidney cancer. Other cell proliferation disorders that can be treated with the IL-2 variant or the derivative thereof of the present disclosure comprise, but are not limited to, neoplasm located in the following positions: abdomen, bone, breast, digestive system, liver, pancreas, peritoneum, endocrine glands (adrenal glands, parathyroid, pituitary, testis, ovary, thymus, thyroid), eyes, head and neck, nervous system (central and peripheral), lymphatic system, pelvis, skin, soft tissue, spleen, chest, and genitourinary system. The disorders further comprise pre-cancerous conditions or lesions and cancer metastasis. In certain embodiments, the cancer is selected from the group consisting of renal cell carcinoma, cutaneous cancer, lung cancer, colorectal cancer, breast cancer, brain cancer, head and neck cancer. Similarly, other cell proliferation disorders can also be treated with the IL-2 variant or the derivative thereof of the present disclosure, comprising but not limited to: hypergammaglobulinemia, lymphoproliferative disorders, paraproteinemias, purpura, sarcoidosis, Sezary syndrome, Waldenstron's macroglobulinemia, Gaucher's Disease, histiocytosis; and any cell proliferation diseases located in the organ system listed above, other than neoplasia. In other embodiments, the disease involves autoimmunity, transplant rejection, post-traumatic immune response, and infectious disease (such as HIV).

The IL-2 variant or the derivative thereof will be used to treat autoimmune disease or alleviate/treat/prevent autoimmune reaction due to organ transplantation, when it comprises the third type of mutation. Autoimmune disease can be selected from the group consisting of: type I diabetes mellitus, rheumatoid arthritis, multiple sclerosis, chronic gastritis, Crohn's disease, Baseow disease, Bechterew disease, psoriasis, myasthenia gravis, autoimmune hepatitis, APECED, Chrug-Strauss syndrome, ulcerative colitis, glomerulonephritis, Guillain-Barré syndrome, Hashimoto thyroiditis, lichen sclerosus, systemic lupus erythematodes, PANDAS, rheumatic fever, sarcoidosis, Sjogren syndrome, Stiff-Man syndrome, scleroderma, Wegener's granulomatosis, vitiligo, autoimmune enteropathy, pulmonary hemorrhage nephritis syndrome (Goodpasture syndrome), dermatomyositis, polymyositis, autoimmune allergy and asthma. In some embodiments, the IL-2 variant or the derivative thereof can be used in combination with an immunosuppressive agent. In some embodiments, the immunosuppressive agent is selected from the group consisting of: glucocorticoid including decortin and prednisol; azathioprine; cyclosporin A; mycophenolate mofetil; tacrolimus; anti-T lymphocyte globulin, anti-CD3 antibody including muromonab; anti-CD25 antibody including basiliximab and daclizumab; anti-TNF-α antibody including infliximab and adalimumab; azathioprine; methotrexate; cyclosporin; sirolimus; everolimus; fingolimod; CellCept; enteric solvent of myfortic sodium (myfortic); and cyclophosphamide.

In some embodiments, the IL-2 variant or the derivative thereof or immunoconjugate thereof of the present disclosure cannot a benefit of curing a disease completely, but only can cure partially. In some embodiments, physiological changes that have some benefits are also considered to be therapeutically beneficial. Thus, in some embodiments, the amount of the IL-2 variant or the derivative thereof, immunoconjugate thereof that provides a physiological change is considered as an "effective amount" or a "therapeutically effective amount". A subject, patient or individual in need of treatment is usually a mammal, and more specifically a human.

In some embodiments, a method for administrating the IL-2 variant or the derivative thereof or immunoconjugate thereof of the present disclosure to a subject is provided, wherein the IL-2 variant or the derivative thereof or immunoconjugate thereof is administrated at least twice a day, at least once a day, at least once every 48 hours, at least once every 72 hours, at least once a week, at least once every 2 weeks, at least once every month, at least once every 2 months or at least once every 3 months. IL-2 can be administered by any effective route, for example by parenteral injection including subcutaneous injection of the IL-2 variant or the derivative thereof, or immunoconjugate thereof.

In a further aspect, the present disclosure provides a method for preparing the IL-2 variant or the derivative or the immunoconjugate thereof, which comprises introducing the mutation(s) of the IL-2 variant described above into wild type human IL-2, or using the nucleic acid sequence described above, or using the expression vector described above, or using the host cell described above. The preparation method of the IL-2 variant in WO2012/107417 as a whole is incorporated herein.

DETAILED DESCRIPTION OF THE INVENTION

Figure 1A:
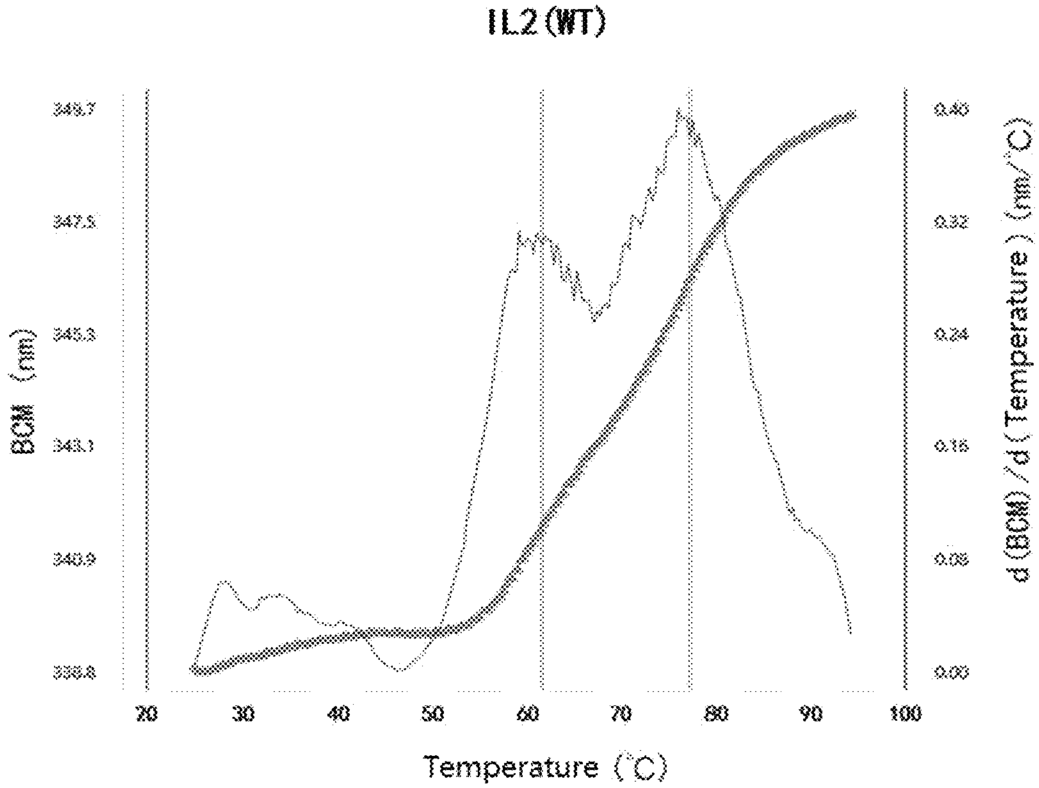
FIGS. 1A to 1F show the experimental results of thermal stability for wild type IL-2 (WT) and the variants thereof IL-2-01, IL-2-02, IL-2-03, IL-2-04 and IL-2-05, respectively.
Figure 1B:
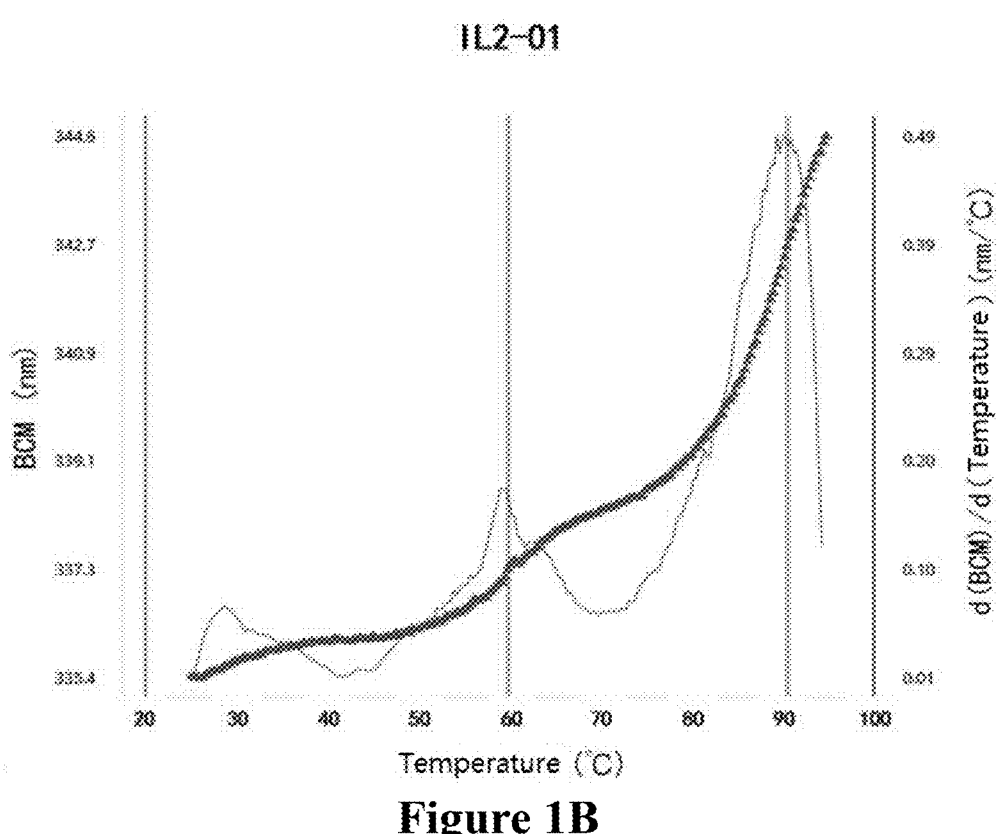
Figure 1C:
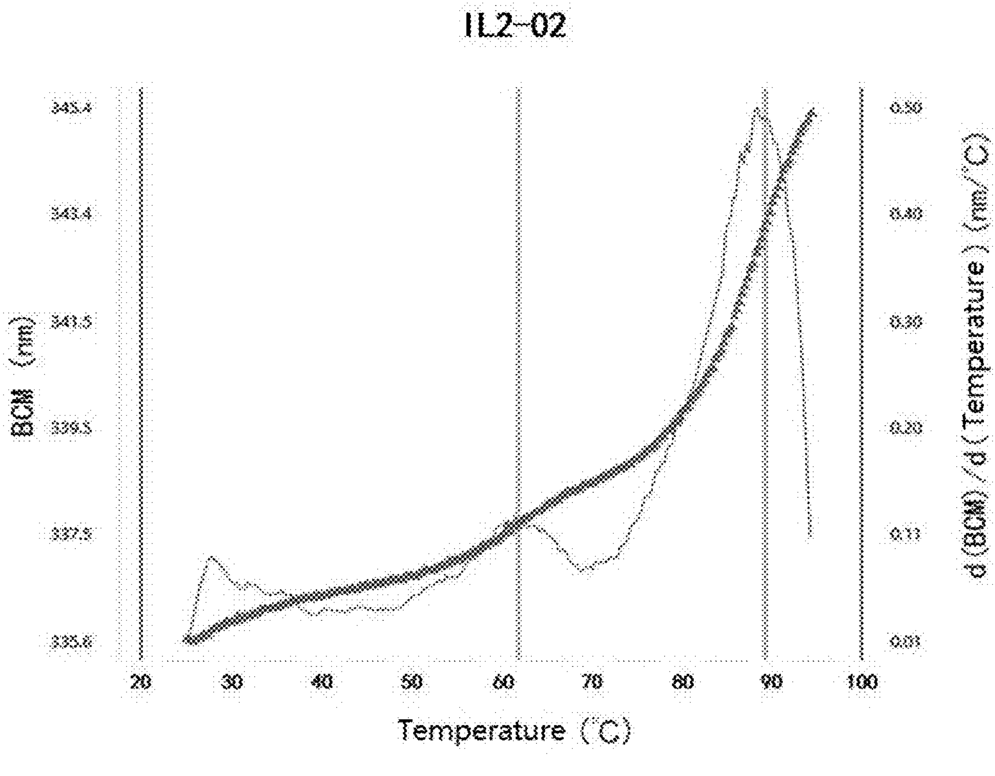
Figure 1D:
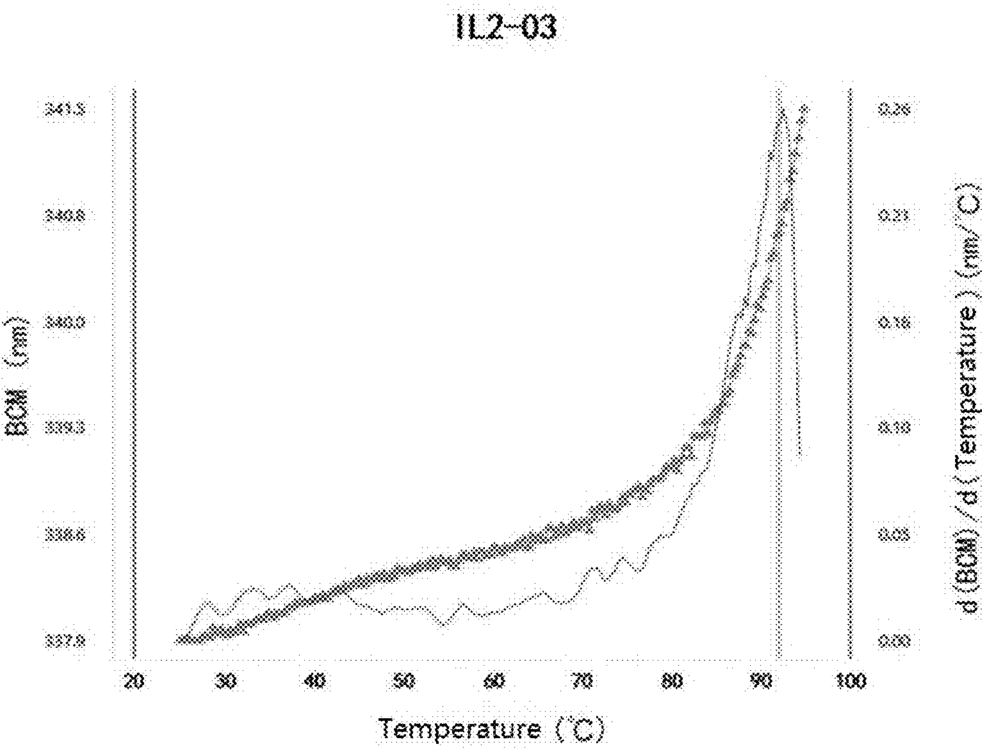
Figure 1E:
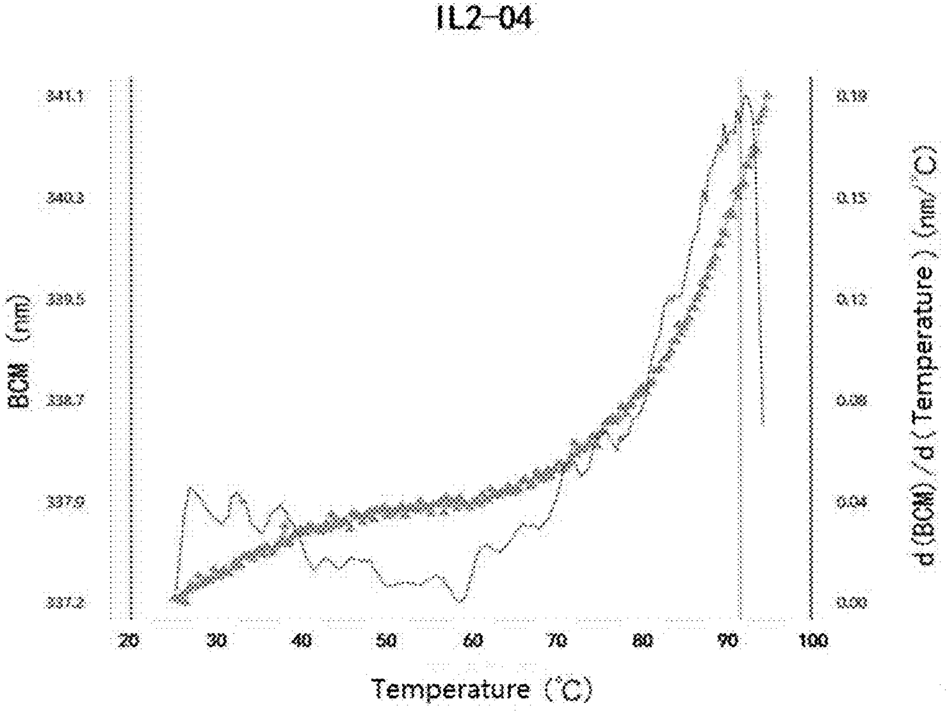
Figure 1F:
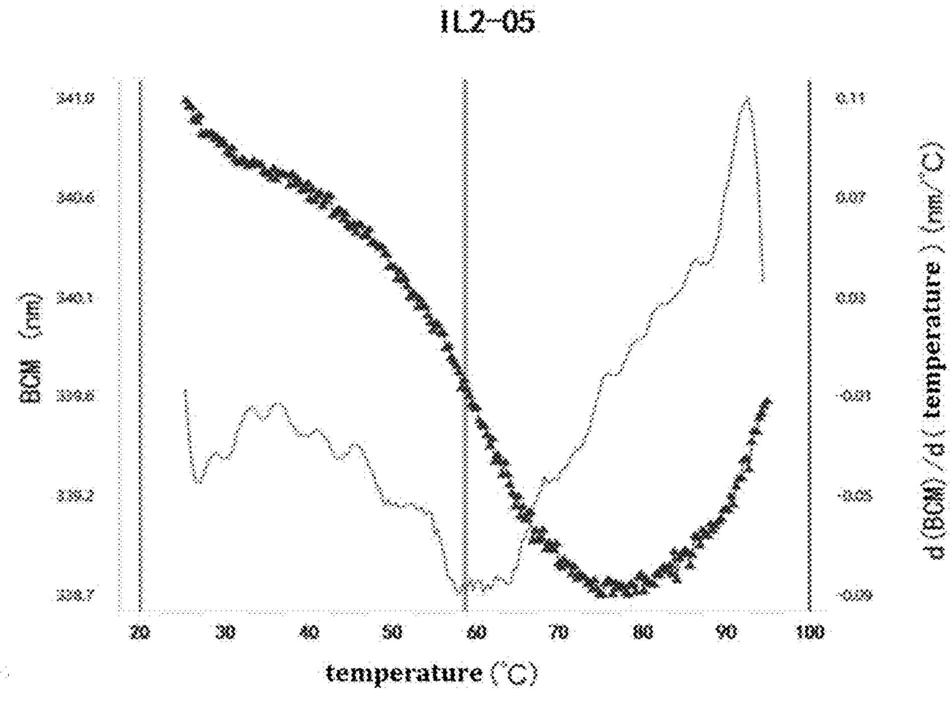

For the present disclosure to be more readily understood, certain technical and scientific terms are specifically defined below. Unless specifically defined herein, all other technical and scientific terms used herein have the meaning commonly understood by one of ordinary skills in the art to which this disclosure pertains.

As used in the disclosure, the three-letter code and the single-letter code for amino acids are as described in J. Biol. Chem, 243, p3558 (1968).

Terminology

"Interleukin-2" or "IL-2" refers to any natural IL-2 from any vertebrate sources, including mammals such as primates (such as human) and rodents (such as mice and rats). The term covers unprocessed IL-2 as well as any processed forms of IL-2 derived from cell. The term also covers naturally occurring IL-2 variants, such as splice variants or allelic variants. The exemplary amino acid sequence of wild type human IL-2 is shown in SEQ ID NO.2. The unprocessed human IL-2 additionally comprises a signal peptide of 20 amino acids at the N-terminus (as shown in SEQ ID NO. 272 in WO2012107417), and the signal peptide is absent in mature IL-2 molecules.

"Amino acid mutation" refers to substitution, deletion, insertion, modification and any combination thereof of amino acid(s) for obtaining a final construct, so that the final construct possesses the desired characteristics, such as enhanced stability. The deletion and insertion of amino acid sequence involve deletion and insertion of amino acid(s) at amino and/or carboxyl terminus. An example of deletion at terminus is the deletion of an alanine residue at the first position of the full-length human IL-2. The preferred amino acid mutation is amino acid substitution. For example, in order to change the binding affinity of IL-2 polypeptides, non-conservative amino acid(s) can be substituted (i.e. one amino acid can be replaced with another amino acid having different structure and/or chemical property). Preferred amino acid substitution involves the substitution of hydrophilic amino acid for hydrophobic amino acid. Amino acid substitution involves substitution of non-naturally-occurring amino acid(s) or derivative(s) of 20 naturally-occurring standard amino acids (e.g. 4-hydroxy proline, 3-methyl histidine, ornithine, homo-serine, 5-hydroxy lysine). Amino acid mutation(s) can be generated using genetic or chemical methods known in the art, including methods such as site-directed mutagenesis, PCR, gene synthesis, and chemical modification.

"Wild type IL-2" is the same as the variant IL-2 polypeptide in the respects other than that it is a form of IL-2 having wild type amino acid at each position corresponding to that of the IL-2 polypeptide variant. For example, if the IL-2 variant is a full-length IL-2 (i.e. an IL-2 that is not fused or conjugated with any other molecule), then the wild type form of this variant is a full-length natural IL-2. If the IL-2 variant is a fusion of IL-2 with another encoding polypeptide (such as an antibody chain) downstream of the IL-2, then the wild type form of such IL-2 variant is an IL-2 having wild type IL-2 amino acid sequence fused to the same downstream polypeptide. In addition, if the IL-2 variant is a truncated form of IL-2 (a sequence in which the mutation(s) or modification(s) is (are) performed within the non-truncated portion of IL-2), then the wild type form of such IL-2 variant is similarly a truncated IL-2 having wild type sequence. In order to compare the binding affinity for IL-2 receptor or biological activity between various forms of IL-2 variants and the corresponding wild type forms of IL-2, the term "wild type" covers naturally occurring IL-2, natural IL-2, an IL-2 form containing one or more amino acid mutation(s) that do not affect the binding to IL-2 receptor, for example, substitution of alanine for cysteine at a position corresponding to residue 125 of human IL-2 (C125A). In some embodiments, the wild type IL-2 comprises the amino acid sequence as shown in SEQ ID NO.2.

"Derivative" is intended to be interpreted broadly, including any IL-2 related products. Derivative refers to but not limited to human and non-human IL-2 homologs, fragments or truncations, fusion proteins (such as fusion with signal peptide or fusion with other active or inactive ingredients, active ingredients such as antibodies or antigen-binding fragments), modified forms thereof (such as PEGylation, glycosylation, conjugation/fusion with albumin, conjugation and/or fusion with Fc, hydroxyethylation, etc.), and conservatively modified proteins.

"CD25" or "alpha subunit of IL-2 receptor" refers to any natural CD25 from any vertebrate sources, including mammals such as primates (such as human) and rodents (such as mice and rats), involves "full-length" unprocessed CD25 and any processed forms of CD25 derived from cells, also involves naturally-occurring CD25 variants, such as splice variants or allelic variants. In certain embodiments, CD25 is human CD25, and an exemplary sequence is shown in SEQ ID NO. 37.

"High-affinity IL-2 receptor" refers to the heterotrimeric form of IL-2 receptor, which is composed of receptor γ subunit (also known as universal cytokine receptor γ subunit, γc or CD132), receptor β subunit (also known as CD122 or p70) and receptor alpha subunit (also known as CD25 or p55). In contrast, "medium-affinity IL-2 receptor" refers to an IL-2 receptor that only comprises γ subunit and β subunit, but without a subunit (see, for example, Olejniczak and Kasprzak, MedSci Monit 14, RA179-189 (2008)).

"Affinity" refers to the total strength of all non-covalent interactions between a single binding site of a molecule (such as a receptor) and its binding partner (such as a ligand). Unless otherwise indicated, the "binding affinity" herein refers to the intrinsic binding affinity that reflects 1:1 interaction between members of the binding pair (for example, a receptor and a ligand). The affinity of molecule X to its partner Y can usually be expressed as the dissociation constant ($K_D$), which is the ratio of the dissociation and association rate constant ($K_{dissociation}$ and $K_{binding}$, respectively). In this way, the affinities will be the same as long as the ratio of the rate constants remains the same, however, the rate constants may be different. Affinity can be measured by conventional methods in the art, including the methods described herein.

"Regulatory T cell" or "$T_{regulatory\ cell}$" or "Treg" refers to a specialized CD4+ T cell type that can suppress the response of other T cells. Tregs are characterized by the expression of the α subunit of the IL-2 receptor (CD25) and the transcription factor forkhead box P3 (FOXP3), and play a key role in inducing and maintaining peripheral autotolerance to antigens (including those antigens expressed by tumors). IL-2 is required to achieve the function, development and the induction of inhibitory characteristics of Tregs.

"Effector cell" refers to a population of lymphocytes that mediate the cytotoxic effects of IL-2. Effector cells include effector T cells, such as CD8+ cytotoxic T cells, NK cells, lymphokine activated killer (LAK) cells, and macrophages/monocytes.

"Antigen-binding module" refers to a polypeptide molecule that specifically binds to an antigenic determinant. In some embodiments, the antigen-binding module can direct the conjugated moiety (e.g., cytokine (IL-2 or the variants thereof) and/or other antigen-binding module) to the target site, such as to a specific type of tumor cell or tumor stroma having a specific antigenic determinant. The antigen-binding module involves antibody and antigen fragments thereof. A preferred antigen-binding module involves the antigen-binding domain of an antibody, which comprises an antibody heavy chain variable region and an antibody light chain variable region. The antigen-binding module may comprise an antibody constant region. As known in the art, the available heavy chain constant region refers to any one of the following five isotypes: α, δ, ε, γ, or μ. Available light chain constant region refers to any of the following two isotypes: κ and λ. IL-2 or the variant thereof can be linked to one or more antigen-binding module(s) via one or more linker sequences to form an "immunoconjugate".

"Specific binding" means that the binding is selective for the antigen, and can be distinguished from undesired or non-specific interaction. The ability of the antigen-binding module to bind to specific antigenic determinant can be achieved by enzyme-linked immunosorbent assay (ELISA) or other techniques well known to those skilled in the art, such as measured by surface plasmon resonance technology (analyzed on BIAcore instrument) (Liljeblad et al., Glyco J17, 323-329 (2000)) and traditional binding assays (Heeley, Endocr Res 28, 217-229 (2002)).

"Antibody" is used in the broadest sense herein, and covers various antibody structures, as long as they exhibit the desired antigen-binding activity. The antibodies refer to, but are not limited to, monoclonal antibodies, polyclonal antibodies, multispecific antibodies (e.g., bi-specific antibodies) and antigen-binding fragments. Antibodies may involve murine antibodies, human antibodies, humanized antibodies, chimeric antibodies, and camelid antibodies. As an example, the antibody may be an immunoglobulin, which is a tetra-peptide chain structure formed by two identical heavy chains and two identical light chains connected by inter-chain disulfide bond(s). The amino acid composition and sequence of the constant region in the immunoglobulin heavy chain are different, leading to different antigenicity. Accordingly, immunoglobulins can be divided into five categories or isotypes of immunoglobulins, namely IgM, IgD, IgG, IgA, and IgE. The corresponding heavy chains are μ chain, δ chain, γ chain, α chain and ε chain. The same type of Ig can be divided into different subclasses, according to the difference in the amino acid composition in hinge region and according to the number and position of heavy chain disulfide bond. For example, IgG can be divided into IgG1, IgG2, IgG3, and IgG4. The light chain is divided into a kappa chain or a lambda chain, according to the difference of the constant region. Each of the five types of Ig can have a kappa chain or a lambda chain.

"Antigen-binding fragment" refers to Fab fragments, Fab' fragments, $F(ab')_2$ fragments, single-chain Fv (i.e. sFv), nanobodies (i.e. VHH), and VH/VL domain having antigen-binding activity. The Fv fragment comprises the heavy chain variable region and the light chain variable region of the antibody, but does not comprise the constant region; Fv fragment is the smallest antigen-binding fragment comprising all antigen-binding sites. Generally, Fv antibody also comprises a polypeptide linker between VH and VL domains, and can form the structure required for antigen-binding. Different linkers can be used to connect the variable regions of two antibodies to form a single polypeptide chain, which is called single chain antibody or single chain Fv (sFv).

"Conservative modification" applies to amino acid and nucleotide sequences. For a specific nucleotide sequence, conservative modification refers to those nucleic acids that encode the same or substantially the same amino acid sequences; or in the case where the nucleotide does not encode amino acid sequence, it refers to substantially the same nucleotide sequences. For amino acid sequence, "conservative modification" refers to the substitution of amino acids in protein for other amino acids with similar characteristics (such as charge, side chain size, hydrophobicity/hydrophilicity, main chain conformation and rigidity, etc), frequent changes can be performed without changing the biological activity of the protein. Generally speaking, those skilled in the art understand that a single amino acid substitution in a non-essential region of a polypeptide does not substantially change the biological activity (see, for example, Watson et al. (1987) Molecular Biology of the Gene, The Benjamin/Cummings Pub. Co., Page 224, ($4^{th}$ edition)).

"PEGylation" refers to the attachment of at least one PEG molecule to another molecule (e.g., a therapeutic protein). For example, Adagen (a PEGylated formulation of adenosine deaminase) was approved for the treatment of severe combined immunodeficiency. It has been shown that the linkage to polyethylene glycol can prevent proteolysis (see, for example, Sada et al., (1991) J. Fermentation Bioengineering 71:137-139). In the most common form, PEG is a linear or branched polyether attached to a hydroxyl group at one end, and has the following general structure: $HO—(CH_2CH_2O)_n—CH_2CH_2—OH$. In order to couple PEG to molecules (polypeptides, polysaccharides, polynucleotides, and small organic molecules), PEG can be activated by preparing some or two PEG derivatives carrying functional groups at end(s). The common way for conjugating PEG onto protein is to activate PEG carrying functional group(s), the functional group is suitable for the reaction with lysine and N-terminal amino acid groups. In particular, the common reactive group involved in conjugation is α or ε amino group of lysine. The reaction between PEGylated linker with the protein can lead to the attachment of the PEG moiety mainly at the following positions: the alpha amino group on N-terminus of the protein, the epsilon amino group on the side chain of lysine residue, or the imidazolyl on side chain of histidine residue. Since most recombinant proteins have a single α and many ε amino groups and imidazole groups, many positional isomers can be generated according to the chemical properties of the linking group.

"Vector", "expression vector" and "expression construct" are synonymous, and refer to a DNA molecule which is used to introduce a specific gene operably associated with the DNA and to direct the expression in target cells, including a vector which serves as an autonomously replicating nucleic acid structure and a vector introduced into the genome of a host cell in into which the vector is introduced. The expression vector herein comprises an expression cassette, which allows the transcription of a large amount of stable mRNA. Once the expression vector is in a target cell, the gene-encoded ribonucleic acid molecule or protein is generated through the cell transcription and/or translation system.

"Host cell", "host cell line" and "host cell culture" are used interchangeably and refer to cells into which exogenous nucleic acid has been introduced, including the progeny of such cells. Host cells involve "transformants" and "transformed cells", which involve initially transformed cells and the progeny derived therefrom (regardless of the number for passages). The progeny may not be exactly the same as the parent cell in the aspect of nucleic acid content, but may comprise mutation(s). The mutated progeny obtained by screening or selection having the same function or biological activity as the function or biological activity of the original transformed cells, are included herein.

"Administration", "dosing" and "treatment", as they apply to an animal, human, experimental subject, cell, tissue, organ or biological fluid, refer to contacting an exogenous pharmaceutical, therapeutic, diagnostic agent, or composition with an animal, human, subject, cell, tissue, organ, or biological fluid. "Administration", "dosing" and "treatment" can e.g. refer to therapeutic, pharmacokinetic, diagnostic, research and experimental methods. Treatment of a cell encompasses contacting a reagent with the cell, as well as contacting a reagent with a fluid, where the fluid is in contact with the cell. "Administration", "dosing" and "treatment" also mean in vitro or ex vivo treatments, e.g., of a cell, with a reagent, diagnostic, binding composition, or with another cell. "Administration" or "treatment", as they apply to a human, veterinary or research subject, refers to therapeutic treatment, prophylactic or preventative measures, research and diagnostic applications.

As used herein, "treat" means to internally or externally administer a therapeutic agent, such as any of the IL-2 variants and the derivatives thereof or a composition comprising the variants and the derivatives thereof of the present disclosure, to a subject being diagnosed to have, being suspected of having, being susceptible to one or more disease symptom(s) for which the therapeutic agent has known therapeutic activity. Typically, the agent is administered in an amount effectively to alleviate one or more disease symptoms in the subject or population to be treated, whether by inducing the regression or inhibiting the progression of such symptom(s) by any clinically measurable degree.

The amount of a therapeutic agent that is effective to alleviate any particular disease symptom (also referred to as the "therapeutically effective amount") may vary according to various factors, such as the disease state, age and body weight of the subject, and the ability of the drug to elicit a desired efficiency in the subject. Whether a disease symptom is alleviated can be assessed by any clinical measurement typically used by physicians or other skilled healthcare providers to assess the severity or progression status of that symptom. While an embodiment of the present disclosure (e.g., a treatment method or article of manufacture) may not be effective in alleviating the target disease symptom(s) in each patient, it should alleviate the target disease symptom (s) in a statistically significant number of subjects as determined by any statistical tests known in the art, such as Student's t-test, chi-square test, U-test according to Mann and Whitney, Kruskal-Wallis test (H-test), Jonckheere-Terpstra-test and Wilcoxon-test.

"Effective amount" encompasses an amount sufficient to ameliorate or prevent a symptom or sign of the medical condition. Effective amount also means an amount sufficient to allow or facilitate diagnosis. An effective amount for a particular subject or veterinary subject may vary depending on factors: such as the condition to be treated, the overall health condition of the subject, the route and dose of administration, and the severity of side effects. An effective amount can be the maximal dose or dosing protocol that avoids significant side effects or toxic effects.

EXAMPLES

Hereinafter, the present disclosure is further described with reference to the following examples. However, the scope of the present disclosure is not limited to the examples.

Example 1: Construction and Expression of Wild Type IL-2 and the Variant Thereof 1. Gene Synthesis and Construction of Recombinant Expression Vector The nucleic acid sequence of wild type human IL-2 was synthesized, Nde I restriction site was introduced at the 5' end, and BamH I restriction site was introduced at the 3' end, the nucleic acid sequence is shown in SEQ ID NO.1 (Nde I and BamH I restriction sites are shown in italics). The amino acid sequence of wild type IL-2 is shown in SEQ ID NO.2.

> The Nucleic Acid Sequence of Wild Type IL-2

(SEQ ID NO. 1)

*CATATG*GCACCGACCAGCAGCAGCACCAAAAAAACCCAGCTGCAACTGGA

ACATCTGCTGTTAGATCTGCAAATGATTCTGAACGGCATCAACAACTACA

AAAATCCGAAACTGACCCGTATGCTGACCTTCAAATTCTACATGCCGAAA

AAAGCAACCGAGCTGAAACATCTGCAGTGTCTGGAAGAAGAACTGAAACC

GCTGGAAGAGGTTCTGAATCTGGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTTGTCAGAGCATTATTAGCACCC

TGACCTAATGA*GGATCC*.

> The Amino Acid Sequence of Wild Type IL-2

(SEQ ID NO. 2)

MAPTSSSTKKTQLQLEHLLLDLQMILNGINNYKNPKLTRMLTFKFYMPK

KATELKHLQCLEEELKPLEEVLNLAQSKNFHLRPRDLISNINVIVLELK

GSETTFMCEYADETATIVEFLNRWITFCQSIISTLT.

After being synthesized, the IL-2 nucleic acid sequence was linked to the *E. coli* expression vector pET-9a (Novagen, Cat. 69431-3) via two restriction sites, Nde I and BamH I, to obtain an expression vector of wild type IL-2.

2. Introduction of the Amino Acid Mutation(s) Described in the Present Disclosure into the Amino Acid Sequence of Wild Type IL-2.

In one variant, the asparagine at position 26 was replaced with glutamine, and the codon AAC at positions 76-78 of the corresponding nucleotide sequence was mutated into CAG, to obtain the variant IL-2-01.

wherein, the italicized portion is the restriction site, and the underlined portion is the mutation site, the following sequences are indicated in a similar way.

> the Nucleic Acid Sequence of IL-2-01:

(SEQ ID NO. 3)

*CATATG*GCACCGACCAGCAGCAGCACCAAAAAAACCCAGCTGCAACTGGA

ACATCTGCTGTTAGATCTGCAAATGATTCTGCAGGGCATCAACAACTACA

AAAATCCGAAACTGACCCGTATGCTGACCTTCAAATTCTACATGCCGAAA

AAAGCAACCGAGCTGAAACATCTGCAGTGTCTGGAAGAAGAACTGAAACC

GCTGGAAGAGGTTCTGAATCTGGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

-continued

GGAATTTCTGAATCGTTGGATTACCTTTGCACAGAGCATTATTAGCACCC

TGACCTAATGA*GGATCC*.

> The Amino Acid Sequence of IL-2-01:

(SEQ ID NO. 4)

MAPTSSSTKKTQLQLEHLLLDLQMILQGINNYKNPKLTRMLTFKFYMPKK

ATELKHLQCLEEELKPLEEVLNLAQSKNFHLRPRDLISNINVIVLELKGS

ETTFMCEYADETATIVEFLNRWITFAQSIISTLT.

In one variant, the asparagine at position 30 was replaced with serine, and the codon AAC at positions 88-90 of the corresponding nucleotide sequence was mutated into AGC to obtain the variant IL-2-02.

> the Nucleic Acid Sequence of IL-2-02:

(SEQ ID NO. 5)

*CATATG*GCACCGACCAGCAGCAGCACCAAAAAAACCCAGCTGCAACTGGA

ACATCTGCTGTTAGATCTGCAAATGATTCTGAACGGCATCAACAGCTACA

AAAATCCGAAACTGACCCGTATGCTGACCTTCAAATTCTACATGCCGAAA

AAAGCAACCGAGCTGAAACATCTGCAGTGTCTGGAAGAAGAACTGAAACC

GCTGGAAGAGGTTCTGAATCTGGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-02:

(SEQ ID NO. 6)

MAPTSSSTKKTQLQLEHLLLDLQMILNGINSYKNPKLTRMLTFKFYMPKK

ATELKHLQCLEEELKPLEEVLNLAQSKNFHLRPRDLISNINVIVLELKGS

ETTFMCEYADETATIVEFLNRWITFAQSIISTLT.

In one variant, the glutamine at position 11 was replaced with cysteine; the codon CAG at positions 31-33 of the corresponding nucleotide sequence was mutated into TGT; the leucine at position 132 was replaced with cysteine; the codon CTG at positions 394-396 of the corresponding nucleotide sequence was mutated into TGT, to obtain the variant IL-2-03.

> The Nucleic Acid Sequence of IL-2-03:

(SEQ ID NO. 7)

*CATATG*GCACCGACCAGCAGCAGCACCAAAAAAACCTGTCTGCAACTGGA

ACATCTGCTGTTAGATCTGCAAATGATTCTGAACGGCATCAACAACTACA

AAAATCCGAAACTGACCCGTATGCTGACCTTCAAATTCTACATGCCGAAA

AAAGCAACCGAGCTGAAACATCTGCAGTGTCTGGAAGAAGAACTGAAACC

GCTGGAAGAGGTTCTGAATCTGGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

-continued

GGAATTTCTGAATCGTTGGATTACCTTTGCACAGAGCATTATTAGCACCT

GTACCTAATGA*GGATCC*.

> The Amino Acid Sequence of IL-2-03:

(SEQ ID NO: 8)

MAPTSSSTKKTCLQLEHLLLDLQMILNGINNYKNPKLTRMLTFKFYMPKK

ATELKHLQCLEEELKPLEEVLNLAQSKNFHLRPRDLISNINVIVLELKGS

ETTFMCEYADETATIVEFLNRWITFAQSIISTCT.

In one variant, the leucine at position 70 was replaced with cysteine; the codon CTG at positions 208-210 of the corresponding nucleotide sequence was mutated into TGT; the proline at position 82 was replaced with cysteine; the codon CCG at positions 244-246 of the corresponding nucleotide sequence was mutated into TGT to obtain the variant IL-2-04.

> The Nucleic Acid Sequence of IL-2-04:

(SEQ ID NO. 9)

*CATATG*GCACCGACCAGCAGCAGCACCAAAAAAACCCAGCTGCAACTGGA

ACATCTGCTGTTAGATCTGCAAATGATTCTGAACGGCATCAACAACTACA

AAAATCCGAAACTGACCCGTATGCTGACCTTCAAATTCTACATGCCGAAA

AAAGCAACCGAGCTGAAACATCTGCAGTGTCTGGAAGAAGAACTGAAACC

GCTGGAAGAGGTTTGTAATCTGGCACAGAGCAAAAACTTTCATCTGCGTT

GTCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-04:

(SEQ ID NO: 10)

MAPTSSSTKKTQLQLEHLLLDLQMILNGINNYKNPKLTRMLTFKFYMPKK

ATELKHLQCLEEELKPLEEVCNLAQSKNFHLRCRDLISNINVIVLELKGS

ETTFMCEYADETATIVEFLNRWITFAQSIISTLT.

In one variant, the glycine at position 27 was replaced with cysteine; the codon GGC at positions 79-81 of the corresponding nucleotide sequence was mutated into TGT; the phenylalanine at position 78 was replaced with cysteine; the codon TTT at positions 232-234 of the corresponding nucleotide sequence was mutated into TGT, to obtain the variant IL-2-05.

> The Nucleic Acid Sequence of IL-2-05:

(SEQ ID NO. 11)

*CATATG*GCACCGACCAGCAGCAGCACCAAAAAAACCCAGCTGCAACTGGA

ACATCTGCTGTTAGATCTGCAAATGATTCTGAACTGTATCAACAACTACA

AAAATCCGAAACTGACCCGTATGCTGACCTTCAAATTCTACATGCCGAAA

AAAGCAACCGAGCTGAAACATCTGCAGTGTCTGGAAGAAGAACTGAAACC

GCTGGAAGAGGTTCTGAATCTGGCACAGAGCAAAAACTGTCATCTGCGTC

CGCGTGATCTGATTAGCAATATTAACGTTATTGTGCTGGAACTGAAAGGT

-continued

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-05:

(SEQ ID NO: 12)
MAPTSSSTKKTQLQLEHLLLDLQMILNCINNYKNPKLTRMLTFKFYMPKK

ATELKHLQCLEEELKPLEEVLNLAQSKNCHLRPRDLISNINVIVLELKGS

ETTFMCEYADETATIVEFLNRWITFAQSIISTLT.

In one variant, the peptide at positions 29-44 was replaced with QSMHIDATL; the codon AACAACTACAAAAATCCGAAACTGACCCGTATGCTGACCTTCAAATTC at positions 85-132 of the corresponding nucleotide sequence were mutated into CAGAGCATGCATATTGATGCAACCCTG to obtain the variant IL-2-06.

> The Nucleic Acid Sequence of IL-2-06:

(SEQ ID NO. 13)
*CATATG*GCACCGACCAGCAGCAGCACCAAAAAAACCCAGCTGCAACTGGA

ACATCTGCTGTTAGATCTGCAAATGATTCTGAACGGCATCCAGAGCATGC

ATATTGATGCAACCCTGTACATGCCGAAAAAAGCAACCGAGCTGAAACAT

CTGCAGTGTCTGGAAGAAGAACTGAAACCGCTGGAAGAGGTTCTGAATCT

GGCACAGAGCAAAAACTTTCATCTGCGTCCGCGTGATCTGATTAGCAATA

TTAACGTTATTGTGCTGGAACTGAAAGGTAGCGAAACCACCTTTATGTGT

GAATATGCCGATGAAACCGCAACCATTGTGGAATTTCTGAATCGTTGGAT

TACCTTTGCACAGAGCATTATTAGCACCCTGACCTAATGA*GGATCC*.

> The Amino Acid Sequence of IL-2-06:

(SEQ ID NO: 14)
MAPTSSSTKKTQLQLEHLLLDLQMILNGIQSMHIDATLYMPKKATELKHL

QCLEEELKPLEEVLNLAQSKNFHLRPRDLISNINVIVLELKGSETTFMCE

YADETATIVEFLNRWITFAQSIISTLT.

In one variant, the phenylalanine at position 42 was replaced with alanine; the codon TTC at positions 124-126 of the corresponding nucleotide sequence was mutated into GCA; the tyrosine at position 45 was replaced with alanine; the codon TAC at positions 133-135 of the corresponding nucleotide sequence was mutated into GCA, to obtain the variant IL-2-07.

> The Nucleic Acid Sequence of IL-2-07:

(SEQ ID NO. 15)
*CATATG*GCACCGACCAGCAGCAGCACCAAAAAAACCCAGCTGCAACTGGA

ACATCTGCTGTTAGATCTGCAAATGATTCTGAACGGCATCAACAACTACA

AAAATCCGAAACTGACCCGTATGCTGACCGCAAAATTCGCAATGCCGAAA

AAAGCAACCGAGCTGAAACATCTGCAGTGTCTGGAAGAAGAACTGAAACC

GCTGGAAGAGGTTCTGAATCTGGCACAGAGCAAAAACTTTCATCTGCGTC

-continued

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-07:

(SEQ ID NO: 16)
MAPTSSSTKKTQLQLEHLLLDLQMILNGINNYKNPKLTRMLTAKFAMPKK

ATELKHLQCLEEELKPLEEVLNLAQSKNFHLRPRDLISNINVIVLELKGS

ETTFMCEYADETATIVEFLNRWITFAQSIISTLT.

In one variant, the phenylalanine at position 42 was replaced with alanine; the codon TTC at positions 124-126 of the corresponding nucleotide sequence was mutated into GCA; the leucine at position 72 was replaced with glycine; the codon CTG at positions 214-216 of the corresponding nucleotide sequence was mutated into GGC to obtain the variant IL-2-08.

> The Nucleic Acid Sequence of IL-2-08:

(SEQ ID NO. 17)
*CATATG*GCACCGACCAGCAGCAGCACCAAAAAAACCCAGCTGCAACTGGA

ACATCTGCTGTTAGATCTGCAAATGATTCTGAACGGCATCAACAACTACA

AAAATCCGAAACTGACCCGTATGCTGACCGCAAAATTCTACATGCCGAAA

AAAGCAACCGAGCTGAAACATCTGCAGTGTCTGGAAGAAGAACTGAAACC

GCTGGAAGAGGTTCTGAATGGCGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-08:

(SEQ ID NO: 18)
MAPTSSSTKKTQLQLEHLLLDLQMILNGINNYKNPKLTRMLTAKFYMPKK

ATELKHLQCLEEELKPLEEVLNGAQSKNFHLRPRDLISNINVIVLELKGS

ETTFMCEYADETATIVEFLNRWITFAQSIISTLT.

In one variant, the tyrosine at position 45 was replaced with alanine; the codon TAC at positions 133-135 of the corresponding nucleotide sequence was mutated into GCA; the leucine at position 72 was replaced with glycine; the codon CTG at positions 214-216 of the corresponding nucleotide sequence was mutated into GGC to obtain the variant IL-2-09.

> The Nucleic Acid Sequence of IL-2-09:

(SEQ ID NO. 19)
*CATATG*GCACCGACCAGCAGCAGCACCAAAAAAACCCAGCTGCAACTGGA

ACATCTGCTGTTAGATCTGCAAATGATTCTGAACGGCATCAACAACTACA

AAAATCCGAAACTGACCCGTATGCTGACCTTCAAATTCGCAATGCCGAAA

AAAGCAACCGAGCTGAAACATCTGCAGTGTCTGGAAGAAGAACTGAAACC

-continued

GCTGGAAGAGGTTCTGAATGGCGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-09:

(SEQ ID NO: 20)
MAPTSSSTKKTQLQLEHLLLDLQMILNGINNYKNPKLTRMLTFKFAMPKK

ATELKHLQCLEEELKPLEEVLNGAQSKNFHLRPRDLISNINVIVLELKGS

ETTFMCEYADETATIVEFLNRWITFAQSIISTLT.

In one variant, the asparagine at position 26 was replaced with glutamine; the codon AAC at positions 76-78 of the corresponding nucleotide sequence was mutated into CAG; the asparagine at position 30 was replaced with serine; the codon AAC at positions 88-90 of the corresponding nucleotide sequence was mutated into AGC; the phenylalanine at position 42 was replaced with alanine; the codon TTC at positions 124-126 of the corresponding nucleotide sequence was mutated into GCA; the leucine at position 72 was replaced with glycine; the codon CTG at positions 214-216 of the corresponding nucleotide sequence was mutated into GGC to obtain the variant IL-2-10.

> The Nucleic Acid Sequence of IL-2-10:

(SEQ ID NO. 21)
*CATATG*GCACCGACCAGCAGCAGCACCAAAAAAACCCAGCTGCAACTGGA

ACATCTGCTGTTAGATCTGCAAATGATTCTGCAGGGCATCAACAGCTACA

AAAATCCGAAACTGACCCGTATGCTGACCGCAAAATTCTACATGCCGAAA

AAAGCAACCGAGCTGAAACATCTGCAGTGTCTGGAAGAAGAACTGAAACC

GCTGGAAGAGGTTCTGAATGGCGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-10:

(SEQ ID NO: 22)
MAPTSSSTKKTQLQLEHLLLDLQMILQGINSYKNPKLTRMLTAKFYMPKK

ATELKHLQCLEEELKPLEEVLNGAQSKNFHLRPRDLISNINVIVLELKGS

ETTFMCEYADETATIVEFLNRWITFAQSIISTLT.

In one variant, the glutamine at position 11 was replaced with cysteine, and the codon CAG at positions 31-33 of the corresponding nucleotide sequence was mutated into TGT; the asparagine at position 26 was replaced with glutamine, the codon AAC at positions 76-78 of the corresponding nucleotide sequence was mutated into CAG; the asparagine at position 30 was replaced with serine, and the codon AAC at positions 88-90 of the corresponding nucleotide sequence was mutated into AGC; the phenylalanine at position 42 was replaced with alanine, and the codon TTC at positions 124-126 of the corresponding nucleotide sequence was mutated into GCA; the leucine at position 72 was replaced with glycine; the codon CTG at positions 214-216 of the corresponding nucleotide sequence was mutated into GGC; the leucine at position 132 was replaced with cysteine, and codon CTG at positions 394-396 of the corresponding nucleotide sequence was mutated into TGT to obtain the variant IL-2-11.

> The Nucleic Acid Sequence of IL-2-11:

(SEQ ID NO. 23)
*CATATG*GCACCGACCAGCAGCAGCACCAAAAAAACCTGTCTGCAACTGGA

ACATCTGCTGTTAGATCTGCAAATGATTCTGCAGGGCATCAACAGCTACA

AAAATCCGAAACTGACCCGTATGCTGACCGCAAAATTCTACATGCCGAAA

AAAGCAACCGAGCTGAAACATCTGCAGTGTCTGGAAGAAGAACTGAAACC

GCTGGAAGAGGTTCTGAATGGCGCACAGAGCAAAAACTTTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCT

GTACCTAATGA*GGATCC*.

> The Amino Acid Sequence of IL-2-11:

(SEQ ID NO: 24)
MAPTSSSTKKTCLQLEHLLLDLQMILQGINSYKNPKLTRMLTAKFYMPKK

ATELKHLQCLEEELKPLEEVLNGAQSKNFHLRPRDLISNINVIVLELKGS

ETTFMCEYADETATIVEFLNRWITFAQSIISTCT.

In one variant, the asparagine at position 26 was replaced with glutamine, and the codon AAC at positions 76-78 of the corresponding nucleotide sequence was mutated into CAG; the asparagine at position 30 was replaced with serine, the codon AAC at positions 88-90 of the corresponding nucleotide sequence was mutated into AGC; the phenylalanine at position 42 was replaced with alanine, and the codon TTC at positions 124-126 of the corresponding nucleotide sequence was mutated into GCA; the leucine at position 70 was replaced with cysteine, and the codon CTG at positions 208-210 of the corresponding nucleotide sequence was mutated into TGT; the leucine at position 72 was replaced with glycine; the codon CTG at positions 214-216 of the corresponding nucleotide sequence was mutated into GGC; the proline at position 82 was replaced with cysteine, the codon CCG at positions 244-246 of the corresponding nucleotide sequence was mutated into TGT to obtain the variant IL-2-12.

> The Nucleic Acid Sequence of IL-2-12:

(SEQ ID NO. 25)
*CATATG*GCACCGACCAGCAGCAGCACCAAAAAAACCCAGCTGCAACTGGA

ACATCTGCTGTTAGATCTGCAAATGATTCTGCAGGGCATCAACAGCTACA

AAAATCCGAAACTGACCCGTATGCTGACCGCAAAATTCTACATGCCGAAA

AAAGCAACCGAGCTGAAACATCTGCAGTGTCTGGAAGAAGAACTGAAACC

GCTGGAAGAGGTTTGTAATGGCGCACAGAGCAAAAACTTTCATCTGCGTT

GTCGTGATCTGATTAGCAATATTAACGTTATTGTGCTGGAACTGAAAGGT

-continued

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-12:

(SEQ ID NO: 26)
MAPTSSSTKKTQLQLEHLLLDLQMILQGINSYKNPKLTRMLTAKFYMPKK

ATELKHLQCLEEELKPLEEVCNGAQSKNFHLRCRDLISNINVIVLELKGS

ETTFMCEYADETATIVEFLNRWITFAQSIISTLT.

In one variant, the asparagine at position 26 was replaced with glutamine, and the codon AAC at positions 76-78 of the corresponding nucleotide sequence was mutated into CAG; the glycine at position 27 was replaced with cysteine, the codon GGC at positions 79-81 of the corresponding nucleotide sequence was mutated into TGT; the asparagine at position 30 was replaced with serine, and the codon AAC at positions 88-90 of the corresponding nucleotide sequence was mutated into AGC; the phenylalanine at position 42 was replaced with alanine, and the codon TTC at positions 124-126 of corresponding nucleoside was mutated into GCA; the leucine at position 72 was replaced with glycine, and the codon CTG at positions 214-216 of the corresponding nucleotide sequence was mutated into GGC; the phenylalanine at position 78 was replaced with cysteine, and the codon TTT at positions 232-234 of the corresponding nucleotide sequence was mutated into TGT to obtain the variant IL-2-13.

> The Nucleic Acid Sequence of IL-2-13:

(SEQ ID NO. 27)
*CATATG*GCACCGACCAGCAGCAGCACCAAAAAAACCCAGCTGCAACTGGA

ACATCTGCTGTTAGATCTGCAAATGATTCTGCAGTGTATCAACAGCTACA

AAAATCCGAAACTGACCCGTATGCTGACCGCAAAATTCTACATGCCGAAA

AAAGCAACCGAGCTGAAACATCTGCAGTGTCTGGAAGAAGAACTGAAACC

GCTGGAAGAGGTTCTGAATGGCGCACAGAGCAAAAACTGTCATCTGCGTC

CGCGTGATCTGATTAGCAATATTAACGTTATTGTGCTGGAACTGAAAGGT

AGCGAAACCACCTTTATGTGTGAATATGCCGATGAAACCGCAACCATTGT

GGAATTTCTGAATCGTTGGATTACCTTTGCACAGAGCATTATTAGCACCC

TGACCTAATGA*GGATCC*.

> The Amino Acid Sequence of IL-2-13:

(SEQ ID NO: 28)
MAPTSSSTKKTQLQLEHLLLDLQMILQCINSYKNPKLTRMLTAKFYMPK

KATELKHLQCLEEELKPLEEVLNGAQSKNCHLRPRDLISNINVIVLELK

GSETTFMCEYADETATIVEFLNRWITFAQSIISTLT.

In one variant, the asparagine at position 29 was replaced with serine, and the codon AAC at positions 85-87 of the corresponding nucleotide sequence was replaced with AGC; the phenylalanine at position 42 was replaced with alanine, the codon TTC at positions 124-126 of the corresponding nucleotide sequence was mutated into GCA; the leucine at position 72 was replaced with glycine, and the codon CTG at positions 214-216 of the corresponding nucleotide sequence was mutated into GGC to obtain the variant IL-2-14.

> The Nucleic Acid Sequence of IL-2-14:

(SEQ ID NO. 29)
*CATATG*GCACCGACCAGCAGCAGCACCAAAAAAACCCAGCTGCAACTGG

AACATCTGCTGTTAGATCTGCAAATGATTCTGAACGGCATCAGCAACTA

CAAAAATCCGAAACTGACCCGTATGCTGACCGCAAAATTCTACATGCCG

AAAAAAGCAACCGAGCTGAAACATCTGCAGTGTCTGGAAGAAGAACTGA

AACCGCTGGAAGAGGTTCTGAATGGCGCACAGAGCAAAAACTTTCATCT

GCGTCCGCGTGATCTGATTAGCAATATTAACGTTATTGTGCTGGAACTG

AAAGGTAGCGAAACCACCTTTATGTGTGAATATGCCGATGAAACCGCAA

CCATTGTGGAATTTCTGAATCGTTGGATTACCTTTGCACAGAGCATTAT

TAGCACCCTGACCTAATGA*GGATCC*.

> The Amino Acid Sequence of IL-2-14:

(SEQ ID NO: 30)
MAPTSSSTKKTQLQLEHLLLDLQMILNGISNYKNPKLTRMLTAKFYMPK

KATELKHLQCLEEELKPLEEVLNGAQSKNFHLRPRDLISNINVIVLELK

GSETTFMCEYADETATIVEFLNRWITFAQSIISTLT.

In one variant, the asparagine at position 26 was replaced with glutamine, and the codon AAC at positions 76-78 of the corresponding nucleotide sequence was mutated into CAG; the asparagine at position 29 was replaced with serine, the codon AAC at positions 85-87 of the corresponding nucleotide sequence was mutated into AGC; the phenylalanine at position 42 was replaced with alanine, and the codon TTC at positions 124-126 of the corresponding nucleotide sequence was mutated into GCA; the leucine at position 72 was replaced with glycine, and the codon CTG at positions 214-216 of the corresponding nucleotide sequence was mutated into GGC to obtain the variant IL-2-21.

> The Nucleic Acid Sequence of IL-2-21:

(SEQ ID NO. 31)
*CATATG*GCACCGACCAGCAGCAGCACCAAAAAAACCCAGCTGCAACTGG

AACATCTGCTGTTAGATCTGCAAATGATTCTGCAGGGCATCAGCAACTA

CAAAAATCCGAAACTGACCCGTATGCTGACCGCAAAATTCTACATGCCG

AAAAAAGCAACCGAGCTGAAACATCTGCAGTGTCTGGAAGAAGAACTGA

AACCGCTGGAAGAGGTTCTGAATGGCGCACAGAGCAAAAACTTTCATCT

GCGTCCGCGTGATCTGATTAGCAATATTAACGTTATTGTGCTGGAACTG

AAAGGTAGCGAAACCACCTTTATGTGTGAATATGCCGATGAAACCGCAA

CCATTGTGGAATTTCTGAATCGTTGGATTACCTTTGCACAGAGCATTAT

TAGCACCCTGACCTAATGA*GGATCC*.

> The Amino Acid Sequence of IL-2-21:

(SEQ ID NO: 32)
MAPTSSSTKKTQLQLEHLLLDLQMILQGISNYKNPKLTRMLTAKFYMPK

KATELKHLQCLEEELKPLEEVLNGAQSKNFHLRPRDLISNINVIVLELK

GSETTFMCEYADETATIVEFLNRWITFAQSIISTLT.

In one variant, the asparagine at position 26 was replaced with glutamine, and the codon AAC at positions 76-78 of the corresponding nucleotide sequence was mutated into CAG; the asparagine at position 29 was replaced with serine, the codon AAC at positions 85-87 of the corresponding nucleotide sequence was mutated into AGC; the phenylalanine at position 42 was replaced with alanine, and the codon TTC at positions 124-126 of the corresponding nucleotide sequence was mutated into GCA; the asparagine at position 71 was replaced with glutamine, and the codon AAT at positions 211-213 of the corresponding nucleotide sequence was mutated into CAG. The leucine at position 72 was replaced with glycine, and the codon CTG at positions 214-216 of the corresponding nucleotide sequence was mutated into GGC to obtain the variant IL-2-22.

> The Nucleic Acid Sequence of IL-2-22:

(SEQ ID NO. 33)

*CATATG*GCACCGACCAGCAGCAGCACCAAAAAAACCCAGCTGCAACTGG

AACATCTGCTGTTAGATCTGCAAATGATTCTGCAGGGCATCAGCAACTA

CAAAAATCCGAAACTGACCCGTATGCTGACCGCAAAATTCTACATGCCG

AAAAAAGCAACCGAGCTGAAACATCTGCAGTGTCTGGAAGAAGAACTGA

AACCGCTGGAAGAGGTTCTGCAGGGCGCACAGAGCAAAAACTTTCATCT

GCGTCCGCGTGATCTGATTAGCAATATTAACGTTATTGTGCTGGAACTG

AAAGGTAGCGAAACCACCTTTATGTGTGAATATGCCGATGAAACCGCAA

CCATTGTGGAATTTCTGAATCGTTGGATTACCTTTGCACAGAGCATTAT

TAGCACCCTGACCTAATGA*GGATCC*.

> The Amino Acid Sequence of IL-2-22:

(SEQ ID NO: 34)

MAPTSSSTKKTQLQLEHLLLDLQMILQGISNYKNPKLTRMLTAKFYMPK

KATELKHLQCLEEELKPLEEVLQGAQSKNFHLRPRDLISNINVIVLELK

GSETTFMCEYADETATIVEFLNRWITFAQSIISTLT.

In one variant, the glutamine at position 11 was replaced with cysteine, and the codon CAG at positions 31-33 of the corresponding nucleotide sequence was mutated into TGT; the peptide at positions 29-44 was replaced with QSMHIDATL, the codon AACAACTACAAAAATCCGAAACTGACCCGTATGCTGACCTTCAAATTC at positions 85-132 of the corresponding nucleotide sequence was mutated into CAGAGCATGCATATTGATGCAACCCTG; the leucine at position 132 was replaced with cysteine, and codon CTG at positions 394-396 of the corresponding nucleotide sequence was mutated into TGT to obtain the variant IL-2-23.

> The Nucleic Acid Sequence of IL-2-23:

(SEQ ID NO. 35)

*CATATG*GCACCGACCAGCAGCAGCACCAAAAAAACCTGTCTGCAACTGG

AACATCTGCTGTTAGATCTGCAAATGATTCTGAACGGCATCCAGAGCAT

GCATATTGATGCAACCCTGTACATGCCGAAAAAAGCAACCGAGCTGAAA

CATCTGCAGTGTCTGGAAGAAGAACTGAAACCGCTGGAAGAGGTTCTGA

ATCTGGCACAGAGCAAAAACTTTCATCTGCGTCCGCGTGATCTGATTAG

CAATATTAACGTTATTGTGCTGGAACTGAAAGGTAGCGAAACCACCTTT

-continued

ATGTGTGAATATGCCGATGAAACCGCAACCATTGTGGAATTTCTGAATC

GTTGGATTACCTTTGCACAGAGCATTATTAGCACCTGTACCTAATGA*GG*

*ATCC*.

> The Amino Acid Sequence of IL-2-23:

(SEQ ID NO: 36)

MAPTSSSTKKTCLQLEHLLLDLQMILNGIQSMHIDATLYMPKKATELKH

LQCLEEELKPLEEVLNLAQSKNFHLRPRDLISNINVIVLELKGSETTFM

CEYADETATIVEFLNRWITFAQSIISTCT.

In one variant, the asparagine at position 26 was replaced with glutamine, and the codon AAC at positions 76-78 of the corresponding nucleotide sequence was mutated into CAG; the asparagine at position 29 was replaced with serine, the codon AAC at positions 85-87 of the corresponding nucleotide sequence was mutated into AGC; the asparagine at position 88 was replaced with arginine, and the codon AAT at positions 262-264 of the corresponding nucleotide sequence was mutated into CGT, to obtain variant IL-2-24.

> The Nucleic Acid Sequence of IL-2-24:

(SEQ ID NO. 40)

*CATATG*GCACCGACCAGCAGCAGCACCAAAAAAACCCAGCTGCAACTGG

AACATCTGCTGTTAGATCTGCAAATGATTCTGCAGGGCATCAGCAACTA

CAAAAATCCGAAACTGACCCGTATGCTGACCTTCAAATTCTACATGCCG

AAAAAAGCAACCGAGCTGAAACATCTGCAGTGTCTGGAAGAAGAACTGA

AACCGCTGGAAGAGGTTCTGAATCTGGCACAGAGCAAAAACTTTCATCT

GCGTCCGCGTGATCTGATTAGCCGTATTAACGTTATTGTGCTGGAACTG

AAAGGTAGCGAAACCACCTTTATGTGTGAATATGCCGATGAAACCGCAA

CCATTGTGGAATTTCTGAATCGTTGGATTACCTTTGCACAGAGCATTAT

TAGCACCCTGACCTAATGA*GGATCC*.

> The Amino Acid Sequence of IL-2-24:

(SEQ ID NO. 41)

MAPTSSSTKKTQLQLEHLLLDLQMILQGISNYKNPKLTRMLTFKFYMPK

KATELKHLQCLEEELKPLEEVLNLAQSKNFHLRPRDLISRINVIVLELK

GSETTFMCEYADETATIVEFLNRWITFAQSIISTLT.

After synthesized, the gene sequence of each of the above variants was linked to pET-9a via two restriction sites, Nde I and BamH I, to obtain recombinant expression vector for each variant of IL-2.

3. Recombinant Expression and Preparation of Wild Type IL-2 and the Variant Thereof The recombinant expression vector was transformed into BL21 (DE3) strain (Novagen, Cat. 69450-3) to obtain recombinant bacteria for wild type IL-2 and variant thereof, and the recombinant bacteria were plated on LB plates comprising Kan resistance for screening.

Single colony was selected by Kan screening and transferred into 10 mL LB medium, cultivated at 37° C., 220 rpm until the $OD_{600}$ reached 1.2±0.2, 50% glycerol was added to a final concentration of 10%, and sub-packaged into cryopreservation tubes (1 mL/tube) and stored at −80° C.

A frozen glycerol tube was taken and recovered in water bath at 37° C., inoculated into 1 L of LB medium, cultivated at 37° C., 220 rpm until $OD_{600}$ reached 0.6 to 1.0, 1M IPTG was added to obtain a final concentration of 1 mM, induced and cultivated at 37° C., 220 rpm for 4 h. After the induction was finished, the bacterium was collected.

The bacterial cells were broken, the inclusion bodies were denatured, re-natured, and purified, the target protein (wild type IL-2 and the variants thereof) were obtained by testing.

Example 2: Preparation of PEGylated IL-2 and the Variant Thereof

IL-2 protein in the buffer system of 10 mM acetic acid-sodium acetate buffer pH 5.0 with a protein concentration of 2 mg/ml was taken; 20 kDa mPEG-butyraldehyde in water was added into the IL-2 protein solution, the amount of substance of mPEG-butyraldehyde was 1-2 times higher than that of the protein; sodium cyanoborohydride aqueous solution was added into the reaction system, the amount of substance of sodium cyanoborohydride was 50-100 times higher than that of the protein; the reaction was performed at 25° C. for about 15-20 hours with stirring, glycine aqueous solution was added to stop the reaction. The final concentration of glycine was 30 mM. After the reaction, PEG modification solution was purified by reversed-phase high performance liquid chromatography to separate impurities (such as di-/multi-modified and naked protein) from mono-PEG modified IL-2. The target component was collected, the buffer was changed, and analysis of activity and binding capacity was performed.

By testing, PEGylated IL-2 and the variant thereof were obtained.

Example 3: Stability Study of IL-2 and the Variant Thereof

1. The Chemical Stability of Wild Type IL-2 and the Variant Thereof

Wild type IL-2 sample (buffer system was 10 mM Tris-HCl, 50 mg/ml mannitol, 0.18 mg/ml SDS, pH 8.5), was incubated at 40° C. for 30 days for stability study, sample was taken for analysis of the degradation by liquid-MS peptide map.

Detection method: 0.5 mL sample was taken, and 0.5 mL denaturing solution was added (8 mol/L guanidine hydrochloride, 0.2 mol/L Tris-HCl, pH 9.0), 8 μl 1 mol/L DTT (dithiothreitol) was added and mixed well, incubated in water bath at 25° C. for 1 hour. Then 35 μl 0.5 mol/L IAC was added and incubated in water bath at 25° C. for 1 hour. The sample was dissolved in digestion buffer (2 mol/L urea, 50 mmol/L Tris-HCl, pH 8.3) by buffer-exchange via the PD-10 column. After buffer-exchange, 12.5 μg trypsin was added into 0.5 mL of the sample and incubated in water bath at 25° C. for 18 hours, hydrochloric acid was added to stop the reaction, and liquid-MS peptide mapping analysis was performed.

See Table 2 for the test results of the liquid-MS peptide mapping. After being kept for 30 days, as for the restriction fragment 9-32 comprising N26 and N29 (i.e. a peptide fragment of amino acids at position 9-32), three fragments with a significant increase in deamination (i.e. 9-32A, 9-32B, 9-32C) were detected. In the process of studying the variants, the stability of the two variants IL-2-08 (F42A/L72G) and IL-2-22 (N26Q/N29S/F42A/N71Q/L72G) were investigated, and samples were taken for detection of degradation. The method was the same as that for wild type IL-2. The results are shown in Table 2.

The experimental results show that three fragments with significant increase in deamination can be detected on the peptide fragment 9-32 of both IL-2-08 and wild type IL-2, with similar increase in deamination, indicating that the mutation of F42A/L72G has no effect on deamination on the peptide fragment 9-32. On the other hand, the mutations of N26 and N29 on both IL-2-22 and IL-2-24 reduced the deamination of the fragments at these two positions. After 30 days, it was detected that the increase of deaminated fragments was <0.5% (not shown in the table), indicating that N26Q and N29S can increase the stability of IL-2.

TABLE 2

Stability results of IL-2 variants (N26 and N29 positions)

| Name | IL-2 Restriction fragments | Possible deamination site | Increase in deamination at day 30 |
|---|---|---|---|
| IL-2 | 9-32 A | Q11/Q13/Q22/N26/N29/N30 | 7.4% |
| | 9-32 B | Q11/Q13/Q22/N26/N29/N30 | 1.7% |
| | 9-32 C | Q11/Q13/Q22/N26/N29/N30 | 4.4% |
| IL-2-08 (F42A/L72G) | 9-32 A | Q11/Q13/Q22/N26/N29/N30 | 6.2% |
| | 9-32 B | Q11/Q13/Q22/N26/N29/N30 | 1.2% |
| | 9-32 C | Q11/Q13/Q22/N26/N29/N30 | 5.2% |
| IL-2-22 (N26Q/N29S/F42A/N71Q/L72G) | 9-32 | Q11/Q13/Q22/Q26/N30 | / |
| IL-2-24 (N26Q/N29S/N88R) | 9-32 | Q11/Q13/Q22/Q26/N30 | / |

In addition, in IL-2-08 (F42A/L72G), four fragments with significant increase in deamination (i.e. 55-76A, 55-76B, 55-76C, 55-76D) were found in the 55-76 restriction sequence. The effect of mutation of N71 into Q was investigated, namely IL-2-22 (N26Q/N29S/F42A/N71Q/L72G); and the stability results are shown in Table 3. The mutation at N71 position reduces the number of deaminated fragments on the 55-76 restriction sequence, reduces the increase in deamination, significantly improves the deamination, and stabilizes the protein; thereby the design meets expectations.

TABLE 3

Stability results of IL-2 variants (N71 position)

| Name | IL-2 Restriction fragments | Possible deamination position | Increase in deamination at day 30 |
|---|---|---|---|
| IL-2-08 (F42A/L72G) | 55-76 A | N71/Q57/Q74 | 14.2% |
| | 55-76 B | N71/Q57/Q74 | 9.8% |
| | 55-76 C | N71/Q57/Q74 | 1.2% |
| | 55-76 D | N71/Q57/Q74 | 10.2% |
| IL-2-22 (N26Q/N29S/F42A/N71Q/L72G) | 55-76 | Q71/Q57/Q74 | 3.1% |

2. The Thermal Stability of Wild Type IL-2 and the Variant Thereof

The stability of 1 mg/mL IL-2 sample (buffer system was 10 mM acetic acid-sodium acetate buffer, pH 4.5, 10% trehalose) was studied with Uncle (Unchained labs) instrument. The temperature of the sample was increased from 25° C. to 95° C. at a rate of 0.3° C./min. At the same time, tryptophan in the sample was excited at 266 nm, and the emission of the sample at 300-400 nm was observed. The melting temperature (Tm) was calculated according to the following formula, where λ is the wavelength (300-400 nm), I (λ) is the emission intensity at this wavelength, and BCM is the barycentric mean, that a wavelength weighted by the light intensity.

$$BCM = \frac{\sum I(\lambda) \times \lambda}{\sum I(\lambda)}$$

$$T_m = \max \frac{dBCM}{dT}$$

As the temperature increases, the BCM parameters of the sample change, reflecting the change in protein conformation. There are two melting temperatures for wild type IL-2, indicating that IL-2 experiences two stages before being completely unfolded. The energy required for the first unfolding stage is lower than that of the second stage. Although N26Q and N30S mutations basically do not affect the first melting temperature, but increase the second melting temperature significantly; while IL-2-03, IL-2-04, and IL-2-05 do not have the first melting temperature, and the second melting temperature is also significantly higher than that of the wild type.

The thermal stability test results of the IL-2 variant are shown in FIGS. 1A-IF and Table 4. The experimental results show that mutations N26Q, N30S, Q11C/L132C, L70C/P82C and G27C/F78C improve the thermal stability of IL-2.

TABLE 4

Melting temperature of wild type IL-2 and the variant thereof

| Name | $T_{m1}$ (° C.) | $T_{m2}$ (° C.) |
|---|---|---|
| IL-2 | 61.5 | 77.5 |
| IL-2-01 | 60.8 | 90.5 |
| IL-2-02 | 61.8 | 89.1 |
| IL-2-03 | Absent | 92.1 |
| IL-2-04 | Absent | 91.8 |
| IL-2-05 | Absent | 92.5 |

Example 4: Determination of Binding Affinity of IL-2 Variant to Interleukin 2 Receptor Alpha (IL-2Rα)

ELISA was used to detect the binding properties of IL-2 and the variant thereof to IL-2Rα. The IL-2Rα recombinant protein with his tag was coated, and IL-2 was added, then the activity of the antibody binding to the antigen was detected by adding HRP-conjugated anti-IL-2 polyclonal antibody and the HRP substrate TMB.

96-well microtiter plate was coated with 2 μg/mL his-tagged IL-2Rα recombinant protein (SinoBiological, Cat #10165-H08H), and incubated overnight at 4° C. The plate was washed with washing solution for three times, 250 μl per well. For each time of washing, the plate was shaken for 10 seconds to ensure sufficient washing. 200 μl/well blocking solution was added and incubated at room temperature for 2 hours. The plate was washed with washing solution for three times, 250 μl per well. For each time of washing, the plate was shaken for 10 seconds to ensure sufficient washing. 100 μl of IL-2 and the variant thereof diluted with dilution solution was added to each well. The plate was incubated for 1 hour at room temperature. The plate was washed with washing solution for three times, 250 μl per well. 100 μl HRP labeled anti-IL-2 polyclonal antibody (SinoBiological, Cat #11848-T16) diluted to 0.1 μg/mL with dilution solution was added to each well. The plate was incubated for 1 hour at room temperature. The plate was washed with washing solution for three times, 250 μl per well. 100 μl TMB was added to each well, and the reaction was performed for 15 minutes in the dark. 50 μl of 0.16 M sulfuric acid was added to each well. The Thermo Multi-SkanFc microplate reader was used to read OD value at 450 nm, and the EC50 value for the binding of IL-2 and the variant thereof to IL-2Rα was calculated.

Figure 2:
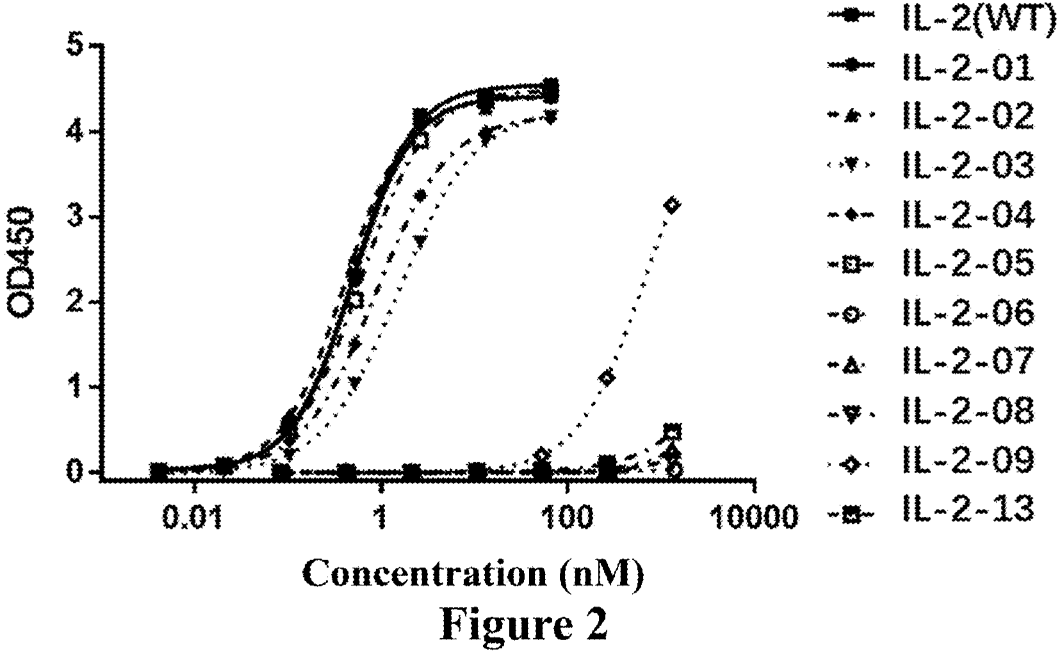
FIG. 2 shows the affinity of wild type IL-2 (WT) and the variants thereof IL-2-01, IL-2-02, IL-2-03, IL-2-04, IL-2-05, IL-2-06, IL-2-07, IL-2-08, IL-2-09 and IL-2-13 to IL-2Rα detected by ELISA experiment.

The ELISA binding data of the variants in Example 4 to IL-2Rα are shown in FIG. 2 and Table 5. The results show that the first type of mutation (namely mutations N26Q, N30S, Q11C/L132C, L70C/P82C, G27C/F78C and N29S) do not affect the binding of IL-2 to IL-2Rα; whereas the second type of mutation (namely F42A/Y45A, F42A/L72G, Y45A/L72G, mutation into QSMHIDATL on positions 29-44) greatly reduce the binding of IL-2 to IL-2Rα; the binding of IL-2 to IL-2Rα can barely be observed under the experimental conditions. The binding of IL-2 to IL-2Rα is also reduced, due to the presence of the second type of mutation, when the two types of mutation are combined.

>IL-2Rα (His Tag)

(SEQ ID NO. 37)

```
ELCDDDPPEIPHATFKAMAYKEGTMLNCECKRGFRRIKSGSLYMLCTGN

SSHSSWDNQCQCTSSATRNTTKQVTPQPEEQKERKTTEMQSPMQPVDQA

SLPGHCREPPPWENEATERIYHFVVGQMVYYQCVQGYRALHRGPAESVC

KMTHGKTRWTQPQLICTGEMETSQFPGEEKPQASPEGRPESETSCHHHH

HH.
```

TABLE 5

The detection of $EC_{50}$ for the binding of IL-2 variant to low-affinity receptor IL-2Rα by ELISA

| Name | The position and type of mutation (Amino acid SEQ ID NO.) | $EC_{50}$ (nM) |
|---|---|---|
| IL-2 | wild type (SEQ ID NO: 2) | 0.50 |
| IL-2-01 | N26Q (SEQ ID NO: 4) | 0.50 |
| IL-2-02 | N30S (SEQ ID NO: 6) | 0.41 |
| IL-2-03 | Q11C/L132C (SEQ ID NO: 8) | 1.53 |
| IL-2-04 | L70C/P82C (SEQ ID NO: 10) | 0.87 |
| IL-2-05 | G27C/F78C (SEQ ID NO: 12) | 0.60 |
| IL-2-06 | mutation into QSMHIDATL at positions 29-44 (SEQ ID NO: 14) | N.A. |
| IL-2-07 | F42A/Y45A (SEQ ID NO: 16) | N.A. |
| IL-2-08 | F42A/L72G (SEQ ID NO: 18) | N.A. |
| IL-2-09 | Y45A/L72G (SEQ ID NO: 20) | N.A. |
| IL-2-13 | N26Q/N30S/G27C/F78C/F42A/L72G (SEQ ID NO. 28) | N.A. |

(Note: N.A., undetectable, due to the low binding capacity of these variants to IL-2Rα, the EC50 cannot be obtained by fitting the data within the concentration range used in the experiment).

Octet RED96e (Fortebio) was used to detect the affinity of IL-2, PEG-IL-2-10, PEG-IL-2-22 and PEG-IL-2-23 to IL-2Rα.

The HIS1K biosensor (Fortebio, 18-5120) was immersed into 200 μL buffer (PBS, pH 7.4, 0.02% tween-20, 0.1% BSA) for 10 minutes, for wetting treatment. Then, human IL-2Rα with His tag (SinoBiological, Cat #10165-H08H) was dissolved in PBS pH 7.4, 0.02% tween-20 and 0.1% BSA, and the sensor was placed in 200 μL of such solution. The sensor was placed in 200 μL buffer (PBS pH 7.4, 0.02% tween-20, 0.1% BSA) to wash off the excess IL-2Rα. Then PEG-IL-2-10, PEG-IL-2-22 and PEG-IL-2-23 were diluted to 133.3 nM with buffer (PBS pH 7.4, 0.02% tween-20, and 0.1% BSA) respectively. The sensor was placed in IL-2 solutions with different concentrations and maintained for 300 seconds for binding. Then the sensor was placed in 200 μL 1×PBS, pH 7.4, 0.02% tween-20, 0.1% BSA, for 600 seconds for dissociation of IL-2. The experimental results in Table 6 show that none of PEG-IL-2-10, PEG-IL-2-22 and PEG-IL-2-23 bind to IL-2Rα.

TABLE 6

Binding affinity of IL-2 variant to low-affinity receptor IL-2Rα (Octet)

| Name | The position and type of mutation (amino acid SEQ ID NO.) | affinity (nM) |
|---|---|---|
| IL-2 | wild type (SEQ ID NO: 2) | 7.83 |
| IL-2-24 | N26Q/N29S/N88R (SEQ ID NO: 38) | 11.8 |
| PEG-IL-2-10 | N26Q/N30S/F42A/L72G (SEQ ID NO: 22) | N.A. |
| PEG-IL-2-22 | N26Q/N29S/F42A/N71G/L72G (SEQ ID NO: 34) | N.A. |
| PEG-IL-2-23 | Q11C/NNYKNPKLTRMLTFKF at positions 29-44 mutated into QSMHIDATL/L132C (SEQ ID NO: 36) | N.A. |

(Note: N.A., undetectable, these variants have a low binding capacity to IL-2Rα, the affinity cannot be obtained by fitting the data within the concentration range used in the experiment.)

Example 5: Determination of Binding Affinity of IL-2 and the Variant Thereof to IL-2 Receptor Beta/Gamma (IL-2Rβ/γ)

The Biacore experiment was used to detect the binding capacity of IL-2 and the variant thereof in Example 1 to IL-2Rβ/γ.

First, the IL-2Rβ and IL-2Rγ subunits were cloned and fused to the Fc hole and Fc knob (SEQ ID NOs. 38 and 39), respectively, to prepare a tool molecule IL-2Rβ/γ-Fc heterodimer. IL-2Rβ-Fc-hole and IL-2Rγ-Fc-knob were co-transfected into HEK293 cells. The heterodimer was purified with Protein A and then Superdex 200 molecular sieve. IL-2Rβ/γ protein was obtained by testing.

>IL-2Rβ (Fc Hole)

(SEQ ID NO. 38)

```
MDMRVPAQLLGLLLLWFPGARCAVNGTSQFTCFYNSRANISCVWSQDGA
LQDTSCQVHAWPDRRRWNQTCELLPVSQASWACNLILGAPDSQKLTTVD
IVTLRVLCREGVRWRVMAIQDFKPFENLRLMAPISLQVVHVETHRCNIS
WEISQASHYFERHLEFEARTLSPGHTWEEAPLLTLKQKQEWICLETLTP
DTQYEFQVRVKPLQGEFTTWSPWSQPLAFRTKPAALGKDTGAQDKTHTC
PPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVS
```

-continued

```
NKALPAPIEKTISKAKGQPREPQVCTLPPSRDELTKNQVSLSCAVKGFY
PSDIAVEWESNGQPENNYKTTPPVLDSDGSFFLVSKLTVDKSRWQQGNV
FSCSVMHEALHNHYTQKSLSLSPGK.
```

>IL-2Rγ (Fc Knob)

(SEQ ID NO. 39)

```
MLKPSLPFTSLLFLQLPLLGVGLNTTILTPNGNEDTTADFFLTTMPTDS
LSVSTLPLPEVQCFVFNVEYMNCTWNSSSEPQPTNLTLHYWYKNSDNDK
VQKCSHYLFSEEITSGCQLQKKEIHLYQTFVVQLQDPREPRRQATQMLK
LQNLVIPWAPENLTLHKLSESQLELNWNNRFLNHCLEHLVQYRTDWDHS
WTEQSVDYRHKFSLPSVDGQKRYTFRVRSRFNPLCGSAQHWSEWSHPIH
WGSNTSKENPFLFALEAGAQDKTHTCPPCPAPELLGGPSVFLFPPKPKD
TLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQ
VYTLPPCRDELTKNQVSLWCLVKGFYPSDIAVEWESNGQPENNYKTTPP
VLDSDGSFFLYSKLTVDKSRWQQGNVFSCSVMHEALHNHYTQKSLSLSP
GK.
```

The Protein A sensor chip (GE, Cat #29127556) of the Biacore instrument (Biacore T200, GE) was used to capture IL-2Rβ/γ-Fc, wherein IL-2Rβ/γ-Fc was diluted with 1×HBS-EP to 1 μg/mL, and flowed at a flow rate of 10 μL/min for 30 seconds. Then, a series of concentration gradient of IL-2 and the variant thereof flowed through the surface of the chip at a flow rate of 30 μL/min, the binding was maintained for 120 seconds and the dissociation was maintained for 360 seconds. The Biacore instrument (Biacore X100, GE) was used to detect the reaction in real time, to obtain association and dissociation curves. After each cycle of dissociation was completed, the chip was washed and regenerated with 10 mM Gly-HCl pH 1.5. The experimental data was fitted to a 1:1 binding model, and the values representing the binding capacity of IL-2 and the variant thereof to medium-affinity receptor IL-2Rβ/γ were obtained, as shown in Table 7.

The results show that all of N26Q, N30S, Q11C/L132C, L70C/P82C, G27C/F78C, F42A/Y45A, F42A/L72G, Y45A/L72G, N26Q/N30S/F42A/L72G, mutation into QSMHIDATL at positions 29-44, and the combination thereof, have little effect on the binding of IL-2 to IL-2Rβ/γ.

TABLE 7

The affinity of IL-2 and the variant thereof to the medium-affinity receptor IL-2Rβ/γ

| Name | $K_{on}$ ($M^{-1}s^{-1}$) | $K_{off}$ ($s^{-1}$) | $K_d$ (nM) |
|---|---|---|---|
| IL-2 (WT) | $9.36 \times 10^5$ | $2.40 \times 10^{-4}$ | 0.257 |
| IL-2-01 | $9.02 \times 10^5$ | $2.20 \times 10^{-4}$ | 0.244 |
| IL-2-02 | $1.03 \times 10^6$ | $2.12 \times 10^{-4}$ | 0.206 |
| IL-2-03 | $5.33 \times 10^5$ | $1.35 \times 10^{-4}$ | 0.253 |
| IL-2-04 | $4.98 \times 10^5$ | $1.50 \times 10^{-4}$ | 0.302 |
| IL-2-05 | $3.36 \times 10^5$ | $9.68 \times 10^{-5}$ | 0.288 |
| IL-2-06 | $8.56 \times 10^5$ | $4.36 \times 10^{-4}$ | 0.509 |
| IL-2-07 | $8.22 \times 10^5$ | $2.15 \times 10^{-4}$ | 0.261 |
| IL-2-08 | $9.20 \times 10^5$ | $2.06 \times 10^{-4}$ | 0.224 |
| IL-2-09 | $6.46 \times 10^5$ | $2.22 \times 10^{-4}$ | 0.344 |
| IL-2-10 | $1.62 \times 10^6$ | $4.30 \times 10^{-4}$ | 0.266 |

A similar method was used to detect the affinity of PEG-IL-2-10, PEG-IL-2-22 and PEG-IL-2-23 to IL-2Rβ/γ by Biacore. The results are shown in Table 8. The results show that the IL-2 variant when coupled to PEG shows a reduced binding to IL-2Rβ/γ to a certain extent, but still maintains a strong affinity. The experimental results show that IL-2-24 rarely binds to IL-2Rβ, when compared to wild type IL-2, indicating that N26Q/N29S/N88R reduces the binding of IL-2 to IL-2Rβ (the results are not shown herein).

TABLE 8

Affinity of PEG-IL-2 variant to medium-affinity receptor IL-2Rβ/γ

| Name | $K_{on}$ ($M^{-1}s^{-1}$) | $K_{off}$ ($s^{-1}$) | $K_d$ (nM) |
|---|---|---|---|
| PEG-IL-2-10 | $1.38 \times 10^6$ | $1.19 \times 10^{-3}$ | 0.86 |
| PEG-IL-2-22 | $1.55 \times 10^5$ | $5.49 \times 10^{-4}$ | 3.54 |
| PEG-IL-2-23 | $3.50 \times 10^5$ | $6.49 \times 10^{-4}$ | 1.86 |

Example 6: Cellular Viability Mediated by High-Affinity Receptor IL-2Rα/β/γ of IL-2 and the Variant Thereof CTLL2 is a mouse-derived cell line that co-expresses IL-2Rα, β, and γ, which can be used to evaluate the cell viability mediated by the high-affinity receptor IL-2Rα/β/γ of each IL-2 variant. Under different concentrations of IL-2 or the variant thereof, the proliferation rate of CTLL-2 was detected to evaluate the biological activity of IL-2 or the variant thereof.

Complete culture medium: RPMI 1640+2 mM L-glutamine+1 mM sodium pyruvate+10% fetal calf serum+10% T-STIM, which was supplemented with concanavalin-A (comprising IL-2); Basic medium: RPMI 1640+2 mM L-glutamine+1 mM sodium pyruvate+10% fetal bovine serum.

CTLL-2 cell proliferation experiment: CTLL-2 cells were cultivated in the complete culture medium at 37° C., 5% $CO_2$ to reach a density of $2.0\times10^5$ cells/mL, the cells were sub-cultured, and CTLL-2 cells were collected by centrifugation after 3-4 days. The cells were washed for 3 times with PBS, and re-suspended in the basic culture medium to prepare a cell suspension having $2.0\times10^5$ cells per mL, and incubated in a 96-well plate, with 90 μL of cells per well. 10 μL of 10×concentrated IL-2 solution prepared with basic culture medium to a corresponding concentration was added. The cells were incubated under a condition of 37° C. and 5% $CO_2$. After incubating for 24 hours, 100 μL of CELLTITER-Glo reagent (Promega) lysis solution was added to each well, and mixed with the solution in the cell plate. The plate was placed into a microplate reader, with 630 nm as the reference wavelength, and the absorbance was measured at a wavelength of 570 nm, and the measured results were recorded.

The data was fitted using a computer program or four-parameter regression algorithm, and the calculation results were calculated as follows:

Relative biological activity of the test sample (%)=$EC_{50}$ of the reference sample/$EC_{50}$ of the test sample (EC50: concentration for 50% of maximal effect).

Figure 3A:
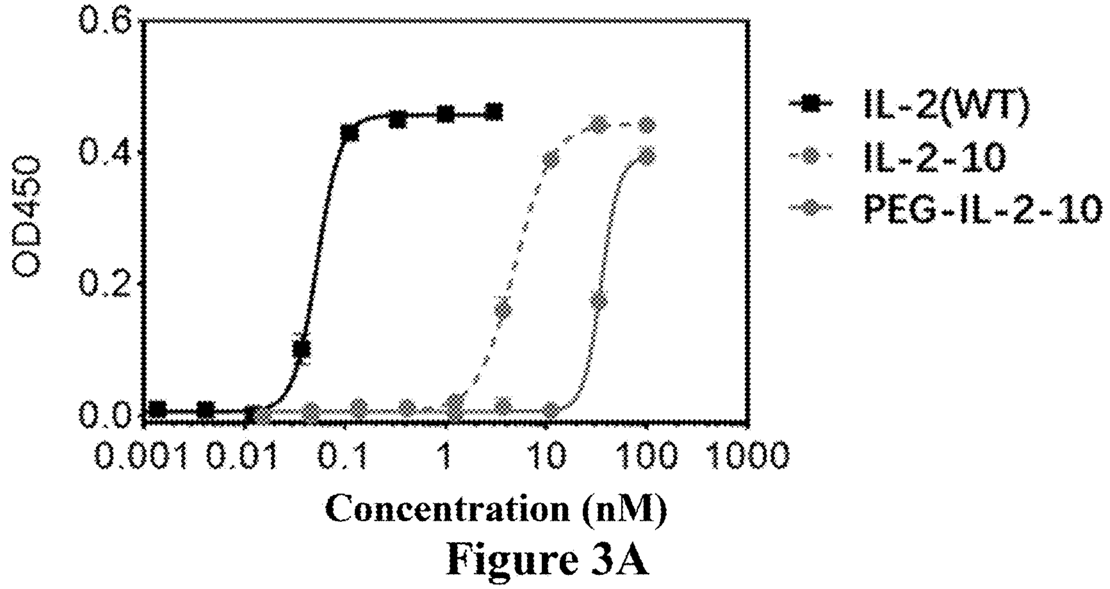
FIG. 3A to 3C are test results showing the CTLL2 cell proliferation facilitated by IL-2-10, IL-2-22, IL-2-23 and PEGylated IL-2-10, PEGylated IL-2-22, and PEGylated IL-2-23, detected by ELISA experiments.
Figure 3B:
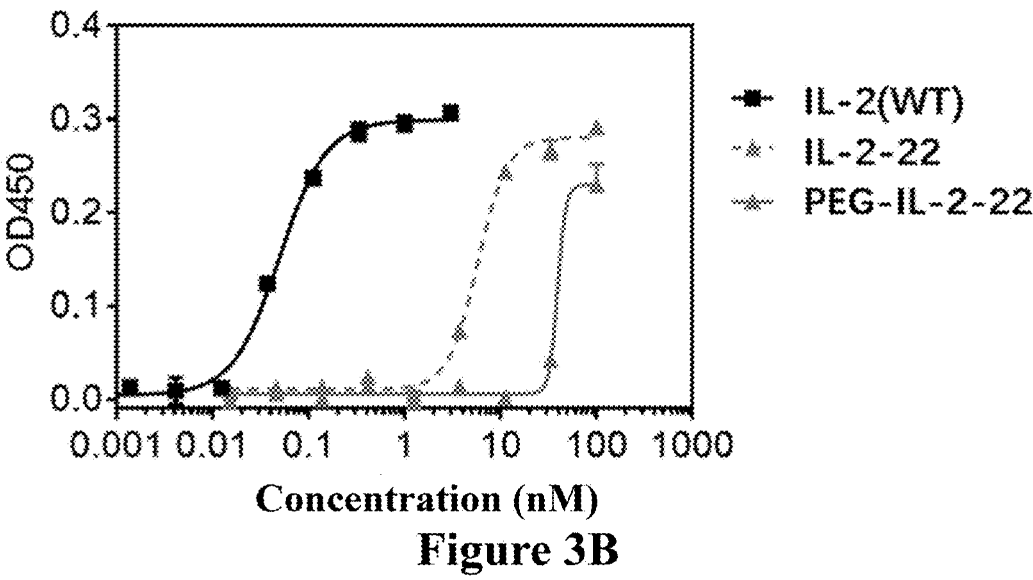
Figure 3C:
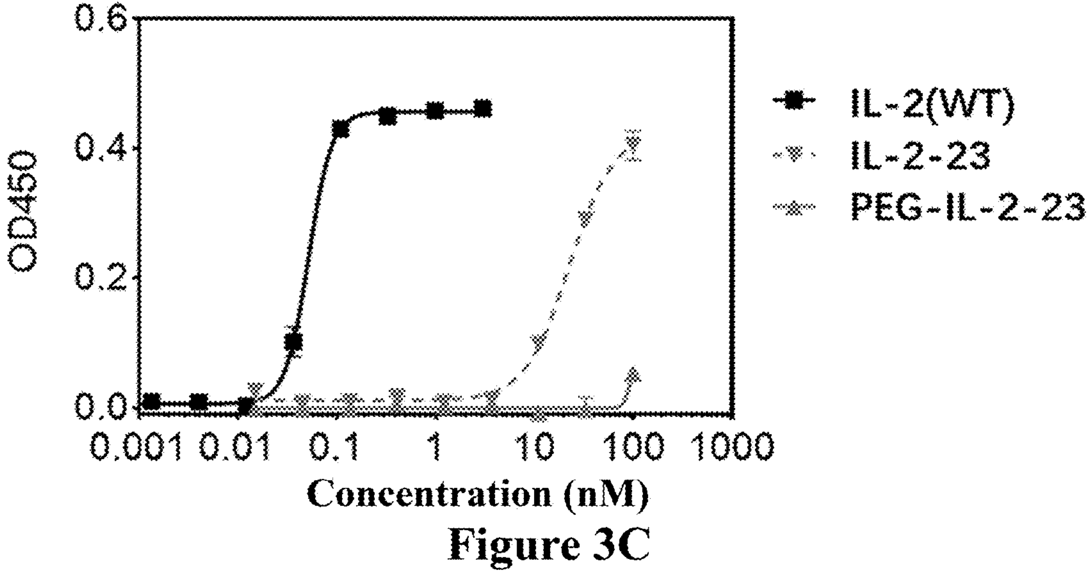

The activity data of IL-2 and the variant thereof are shown in Table 9, Table 10 and FIGS. 3A-3C. The results show that the first type of mutation (namely mutations N26Q, N29S, N30S, Q11C/L132C, L70C/P82C and G27C/F78C) do not affect or even slightly enhance the activity of IL-2 to promote the proliferation of CTLL2 cells; whereas the second type of mutation (i.e., F42A/Y45A, F42A/L72G, Y45A/L72G, and mutation into QSMHIDATL at positions 29-44) reduces the binding of IL-2 to IL-2Rα, as well as reduces the activity of IL-2 to promote the proliferation of CTLL2 cells.

TABLE 9

Activity of IL-2 variants to promote the proliferation of CTLL2-cells

| Name | The position and type of mutation (Amino acid SEQ ID NO.) | relative biological activity |
|---|---|---|
| IL-2 | wild type (SEQ ID NO: 2) | 100% |
| IL-2-01 | N26Q (SEQ ID NO: 4) | 96% |
| IL-2-02 | N30S (SEQ ID NO: 6) | 117% |
| IL-2-03 | Q11C/L132C (SEQ ID NO: 8) | 162% |
| IL-2-04 | L70C/P82C (SEQ ID NO: 10) | 176% |
| IL-2-05 | G27C/F78C (SEQ ID NO: 12) | 229% |
| IL-2-06 | mutation into QSMHIDATL at positions 29-44 (SEQ ID NO: 14) | 4% |
| IL-2-07 | F42A/Y45A (SEQ ID NO: 16) | 4% |
| IL-2-08 | F42A/L72G (SEQ ID NO: 18) | 7% |
| IL-2-09 | Y45A/L72G (SEQ ID NO: 20) | 2% |

TABLE 10

Activity of IL-2 variants to promote the proliferation of CTLL2-cells

| Name | The position and type of mutation (amino acid SEQ ID NO.) | $EC_{50}$ (nM) | relative biological activity |
|---|---|---|---|
| IL-2 | wild type (SEQ ID NO: 2) | 0.053 | 100% |
| IL-2-10 | N26Q/N30S/F42A/L72G (SEQ ID NO: 22) | 4.80 | 1% |
| IL-2-22 | N26Q/N29S/F42A/N71G/L72G (SEQ ID NO: 34) | 5.73 | 0.9% |
| IL-2-23 | Q11C/NNYKNPKLTRMLTFKF at positions 29-44 mutated into QSMHIDATL/L132C (SEQ ID NO: 36) | 22.71 | 0.2% |
| PEG-IL-2-10 | N26Q/N30S/F42A/L72G (SEQ ID NO: 22) | 35.29 | 0.2% |
| PEG-IL-2-22 | N26Q/N29S/F42A/N71G/L72G (SEQ ID NO: 34) | 39.25 | 0.1% |
| PEG-IL-2-23 | Q11C/NNYKNPKLTRMLTFKF at positions 29-44 mutated into QSMHIDATL/L132C (SEQ ID NO: 36) | N.A. | N.A. |

(Note: N.A., undetectable, it means that the effect of the variant on CTLL2 cell proliferation is low, and the EC50 cannot be obtained by fitting data within the concentration range used in the experiment.)

Example 7: Cellular Viability Mediated by the Medium-Affinity Receptor IL-2Rβ/γ of IL-2 and the Variant Thereof Mo7e is a human-derived cell line that only expresses IL-2Rβ and γ, but does not express IL-2Rα. Mo7e can be used to evaluate the cell viability mediated by the medium-affinity receptor IL-2Rβ/γ of each IL-2 variant. Under different concentrations of IL-2 or the variant thereof, the cell line-dependent proliferation rate of Mo7e was detected to evaluate the biological activity of IL-2 or the variant thereof.

Complete culture medium: RPMI 1640+2 mM L-glutamine+1 mM sodium pyruvate+10% fetal calf serum+15 ng/mL GM-CSF; basic medium: RPMI 1640+2 mM L-glutamine+1 mM sodium pyruvate+10% fetal bovine serum.

Mo7e cell proliferation experiment: Mo7e cells were cultivated in the complete culture medium at 37° C., 5% $CO_2$ to reach a density of $2.0\times10^5$ cells/mL, the cells were sub-cultured, and Mo7e cells were collected by centrifugation after 3-4 days. The cells were washed for 3 times with PBS, and re-suspended in the basic culture medium to prepare a cell suspension having $2.0\times10^5$ cells per mL, and incubated in a 96-well plate, with 90 μL of cells per well. 10 μL of 10× concentrated IL-2 solution prepared with basic culture medium to a corresponding concentration was added. The cells were incubated under a condition of 37° C. and 5% $CO_2$. After incubating for 72 hours, 100 μL of CELLTITER-Glo reagent (Promega) lysis solution was added to each well, and mixed with the solution in the cell plate. The plate was placed into a microplate reader, with 630 nm as the reference wavelength, and the absorbance was measured at a wavelength of 570 nm, and the measured results were recorded. The same method in Example 6 was used to calculate the relative biological activity.

Figure 4A:
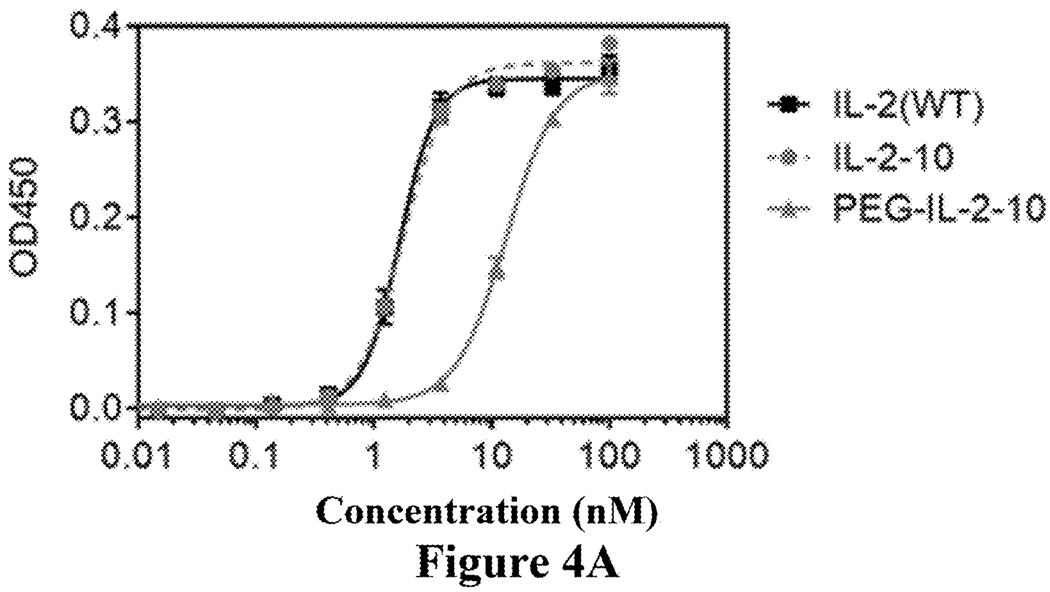
FIGS. 4A to 4C are test results showing the Mo7e cell proliferation facilitated by IL-2-10, IL-2-22, IL-2-23 and PEGylated IL-2-10, PEGylated IL-2-22, and PEGylated IL-2-23, detected by ELISA experiments.
Figure 4B:
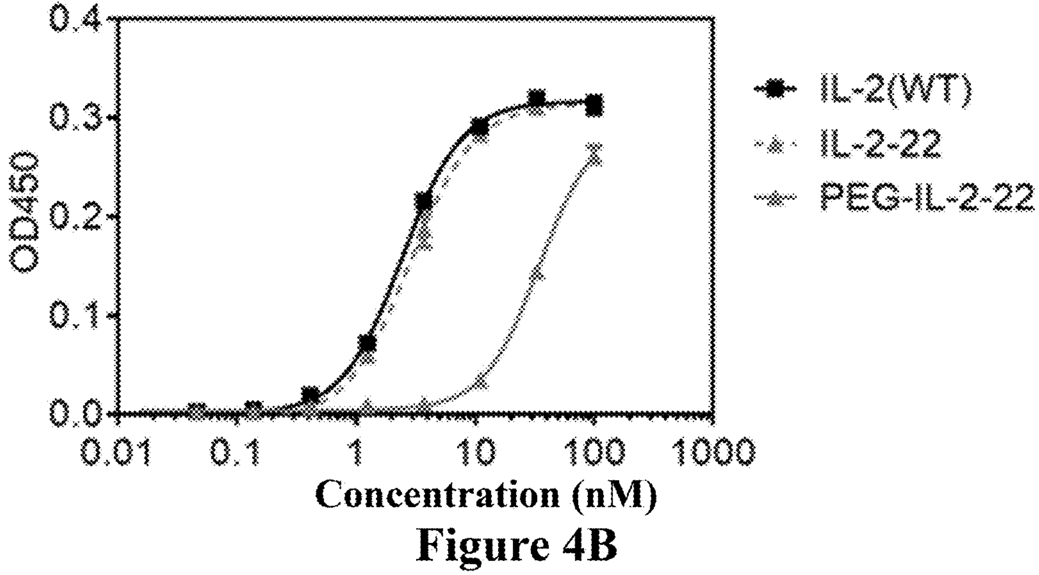
Figure 4C:
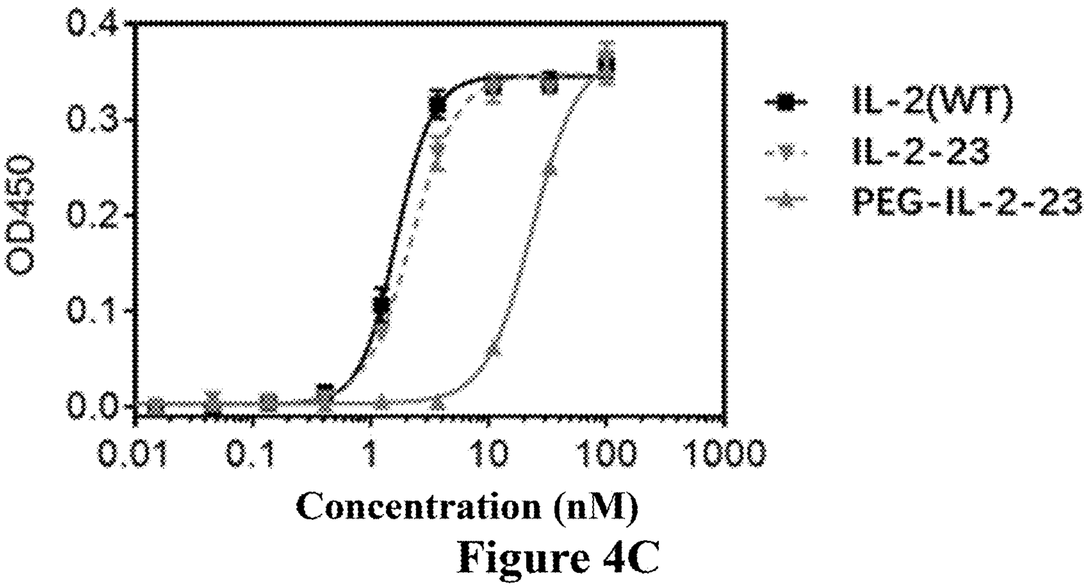

The Mo7e cell proliferation activity data for IL-2 and the variant thereof are shown in Table 11 and FIGS. 4A-4C. The results show that neither the first type of mutation (namely mutations N26Q, N29S, N30S, Q11C/L132C, L70C/P82C and G27C/F78C), nor the second type of mutation (namely F42A/Y45A, F42A/L72G, Y45A/L72G, and mutation into QSMHIDATL at positions 29-44) affect the activity of IL-2 to promote the proliferation of Mo7e cells, indicating that they do not affect the affinity of IL-2 to IL-2Rβ/γ. IL-2 when coupled to PEG will reduce the activity of IL-2 to promote the proliferation of Mo7e cells to a certain extent, but still maintain favorable binding.

TABLE 11

Activity of IL-2 and the variant thereof to promote the proliferation of Mo7e-cells

| Name | The position and type of mutation (amino acid SEQ ID NO.) | $EC_{50}$ (nM) | relative biological activity |
|---|---|---|---|
| IL-2 | wild type (SEQ ID NO: 2) | 2.44 | 100% |
| IL-2-10 | N26Q/N30S/F42A/L72G (SEQ ID NO: 22) | 1.78 | 137% |
| IL-2-22 | N26Q/N29S/F42A/N71G/L72G (SEQ ID NO: 34) | 2.84 | 86% |
| IL-2-23 | Q11C/NNYKNPKLTRMLTFKF at positions 29-44 mutated into QSMHIDATL/L132C (SEQ ID NO: 36) | 2.22 | 110% |
| PEG-IL-2-10 | N26Q/N30S/F42A/L72G (SEQ ID NO: 22) | 13.19 | 19% |
| PEG-IL-2-22 | N26Q/N29S/F42A/N71G/L72G (SEQ ID NO: 34) | 34.81 | 7% |
| PEG-IL-2-23 | Q11C/NNYKNPKLTRMLTFKF at positions 29-44 mutated into QSMHIDATL/L132C (SEQ ID NO: 36) | 23.37 | 10% |

Example 8: Determination of the Activity of IL-2 and the Variant Thereof in STAT5 Phosphorylation in CTLL2 Cells The biological activity of IL-2 or the variant thereof was detected, based on the phosphorylation level of STAT5 in cell-dependent strain CTLL-2 at different concentrations of IL-2 or the variant thereof.

Complete culture medium: RPMI 1640+2 mM L-glutamine+1 mM sodium pyruvate+10% fetal bovine serum+10% T-STIM culture supplement with concanavalin-A (comprising IL-2); Basic medium: RPMI 1640+2 mM L-glutamine+1 mM sodium pyruvate+10% fetal bovine serum.

STAT5 phosphorylation experiment in CTLL-2 cells: CTLL-2 cells were cultivated in complete culture medium at 37° C. and 5% $CO_2$ to reach a density of $2.0\times10^5$ cells per mL, and washed with PBSA (PBS, pH7.2, 1% BSA) once, and the density was adjusted to $1.0\times10^6$ cells per mL, and the cells were aliquoted into tubes with 500 μL per tube. The corresponding concentrations of the concentrated IL-2 solution prepared with basic culture medium were incubated at room temperature for 20 minutes; paraformaldehyde was immediately added to a final concentration of 1.5% and mixed by vortex, and incubated at room temperature for 10 minutes. 1 mL PBS was added, and centrifuged at 4° C., 1400 rpm for 5 minutes to remove paraformaldehyde. The cells were re-suspended, 1 mL of 100% pre-cooled methanol was added at 4° C. and mixed by vortex, the cells were incubated at 4° C. for 20 minutes. 3 mL PBSA buffer was added, and centrifuged at 4° C., 1400 rpm for 5 minutes. The cells were washed twice. Alexa Fluor 647-conjugated anti-STAT5-pY694 antibody (BD, Cat #612599) was incubated for 30 minutes at room temperature in the dark. The cells were washed twice with 3 mL PBSA, and detected by flow cytometer. The method as described in Example 6 was used to calculate the relative biological activity.

Figures 5, 6A:
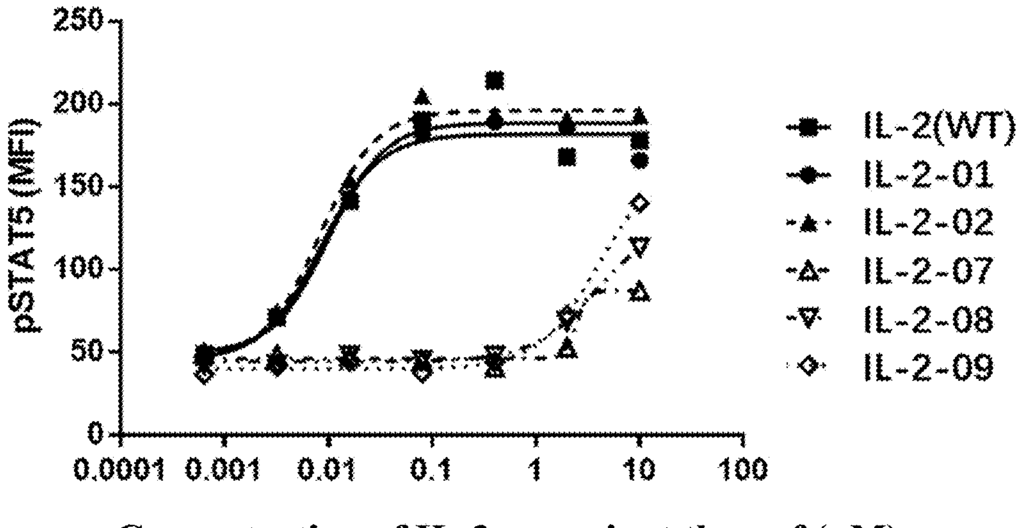
FIG. 5 shows the experimental results of phosphorylation of STAT5 in CTLL2 cells for IL-2-01, IL-2-02, IL-2-07, IL-2-08, and IL-2-09, detected by flow cytometry.
FIG. 6A to 6C show the experimental results of phosphorylation of STAT5 in human periphery blood regulatory T cell Tregs (FIG. 6A), in CD8+ T cells (FIG. 6B) and in NK cells (FIG. 6C) stimulated by IL-2-10, IL-2-22, IL-2-23 and PEGylated IL-2-10, PEGylated IL-2-22, and PEGylated IL-2-23, respectively.

Data of the activity of IL-2 and the variant thereof in the STAT5 phosphorylation in CTLL2 cells are shown in FIG. 5 and Table 12. The results show that mutations N26Q, N29S and N30S do not affect or even slightly enhance the activity of IL-2 in STAT5 phosphorylation in CTLL2 cells, while F42A/Y45A, F42A/L72G and Y45A/L72G reduce the activity of IL-2 in STAT5 phosphorylation in CTLL2 cells. Thereby, it can be proved that N26Q, N29S, and N30S do not affect the binding of IL-2 to the high-affinity receptor IL-2Rα/B/γ, whereas F42A/Y45A, F42A/L72G and Y45A/L72G reduce the binding of IL-2 to high-affinity receptor IL-2Rα/B/γ.

TABLE 12

Activity of IL-2 wild type and the variant thereof in STAT5 phosphorylation in CTLL2-cells

| Name | Mutation (amino acid SEQ ID NO.) | $EC_{50}$ (nM) | relative biological activity |
|---|---|---|---|
| IL-2 | wild type (SEQ ID NO: 2) | 0.010 | 100% |
| IL-2-01 | N26Q (SEQ ID NO: 4) | 0.0084 | 119% |
| IL-2-02 | N30S (SEQ ID NO: 6) | 0.0084 | 119% |
| IL-2-07 | F42A/Y45A (SEQ ID NO: 16) | 2.45 | 0.41% |
| IL-2-08 | F42A/L72G (SEQ ID NO: 18) | 3.93 | 0.25% |
| IL-2-09 | Y45A/L72G (SEQ ID NO: 20) | 4.02 | 0.25% |

Example 9: Determination of the Activity of IL-2 and the Variant Thereof in STAT5 Phosphorylation in Human Peripheral Blood (PBMC)

The biological activity of IL-2 was detected, based on the phosphorylation level of STAT5 in various cell populations in human peripheral blood (including Tregs, NK cells, CD4+ T cells, and CD8+ T cells), under different concentrations of IL-2 or the variant thereof.

Basic medium: RPMI 1640+10% fetal bovine serum.

Antibody mixture: CD3 APC-Cy7 (BD 557832), CD4 BB515 (BD 564419), CD8 BB700 (BD 566452), CD25 BV421 (BD 564033), FOXP3 PE (BD 560852), CD56 BV650 (BD 564057), pSTAT5 AF647 (BD 562076).

Experiment of STAT5 phosphorylation in human PBMC: freshly isolated human PBMC cells were adjusted to a density of $6.0\times10^6$ cells per mL with basic medium, and 90 μL was added into a 96-well plate. IL-2 and the variant thereof and derivative thereof were diluted with basic medium to 1000 nM, 100 nM, 10 nM, 1 nM, 0.1 nM, 0.01 nM; 10 μL of which was added into 90 μL PBMCs and stimulated at 37° C. for 15 minutes. Then, the cells were immediately fixed with pre-warmed BD Cytofix buffer (BD, Cat No. 554655) at 37° C. for 10 minutes. The cells were centrifuged at 350 g for 7 minutes at 4° C. The supernatant was removed, 200 μL of BD Phosflow Perm Buffer III (BD, Cat No. 558050) pre-cooled at −20° C. was added on ice for 30 minutes for digestion of the cell membrane. The cells were centrifuged at 450 g for 7 minutes at 4° C. The supernatant was removed, 200 μL of PBS pH 7.4 was added for washing twice. 100 μL of FcR blocker diluted at 1:200 was added and incubated at 4° C. for 20 minutes. The sample was centrifuged at 450 g for 7 minutes at 4° C. The supernatant was removed, 100 μL of antibody mixture was added, and the cells were stained at room temperature for 40 minutes. The sample was centrifuged at 450 g for 7 minutes at 4° C. The supernatant was removed, 200 μL of PBS pH 7.4 was added for washing once. 200 μL of PBS pH 7.4 was added to re-suspend the PBMCs for detection with flow cytometer. NK cells are defined as CD3-CD56+ cells, CD8+ T cells are defined as CD3+CD4-CD8+ cells, and Tregs are defined as CD3+CD4+CD25+Foxp3+ cells.

For the three cell populations described above, the pSTAT5 fluorescence values (MFI) under different IL-2 concentrations were summarized, fitted by using a computer program or a four-parameter regression algorithm, and the relative biological activity was calculated according to the same method as that in Example 6.

The results show that F42A/L72G and the mutation(s) in IL-2-10 and IL-2-23 only reduce the binding of IL-2 to IL-2Rα, but do not affect the binding of IL-2 to IL-2Rβ/γ; therefore the reduction in Treg activity caused by these mutations is greater than that in CD8+ T cells and that in NK cells. On the contrary, since N88R does not affect the binding of IL-2 to IL-2Rα, but reduces the binding of IL-2 to IL-2Rβ, therefore the reduction in Tregs activity caused by IL-2 is less than that in CD8+ T cells. IL-2 when coupled to PEG will result in a reduction of effect of IL-2 on activation of CD8+ T cells and NK cells, to a certain extent.

Figure 6B:
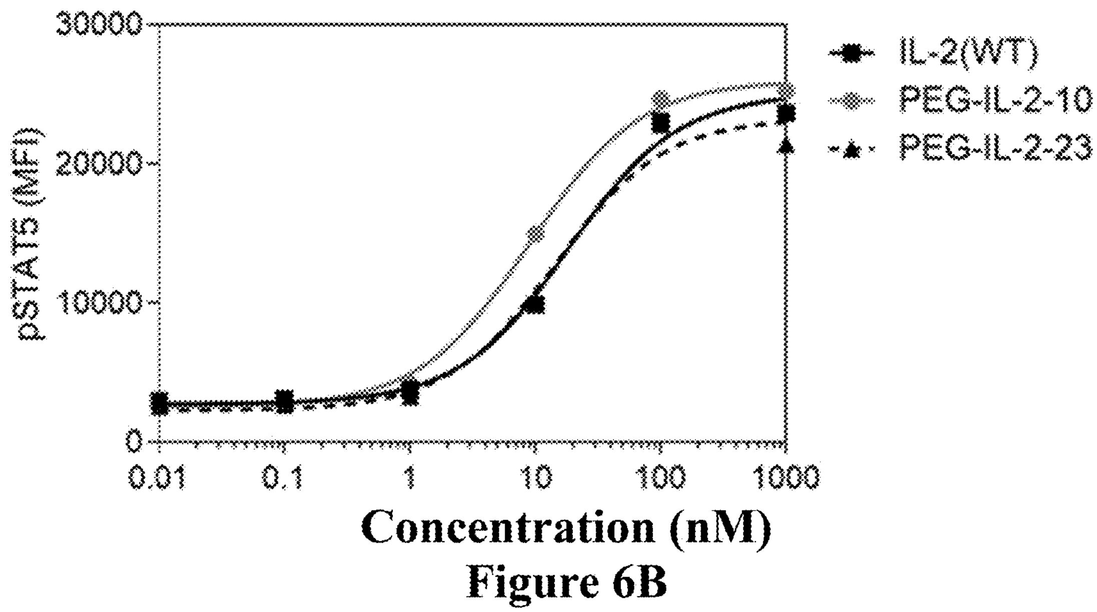
Figure 6C:
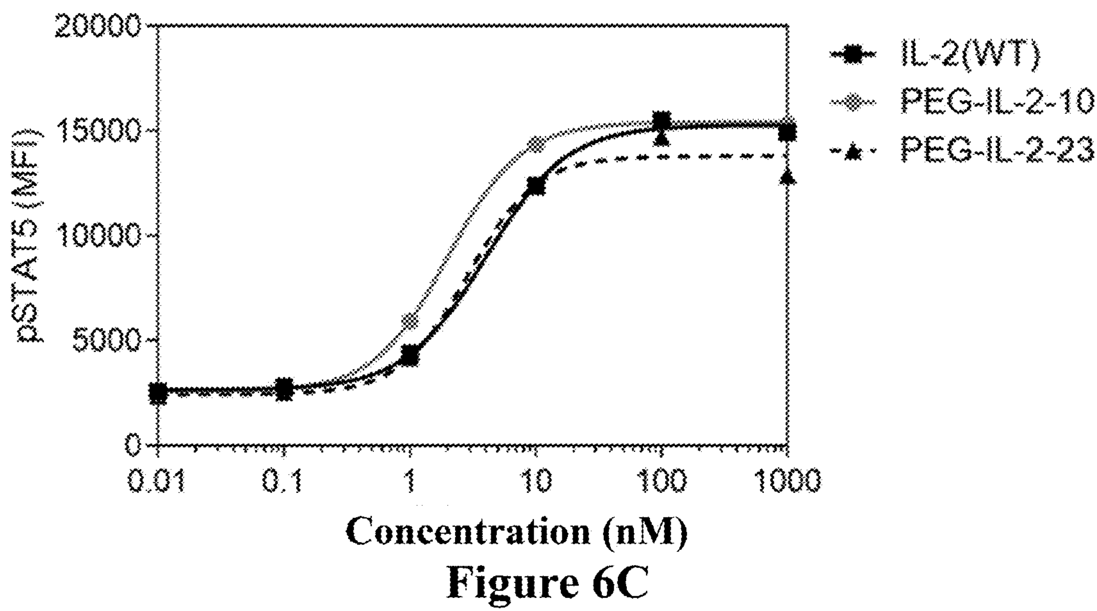
Figure 7A:
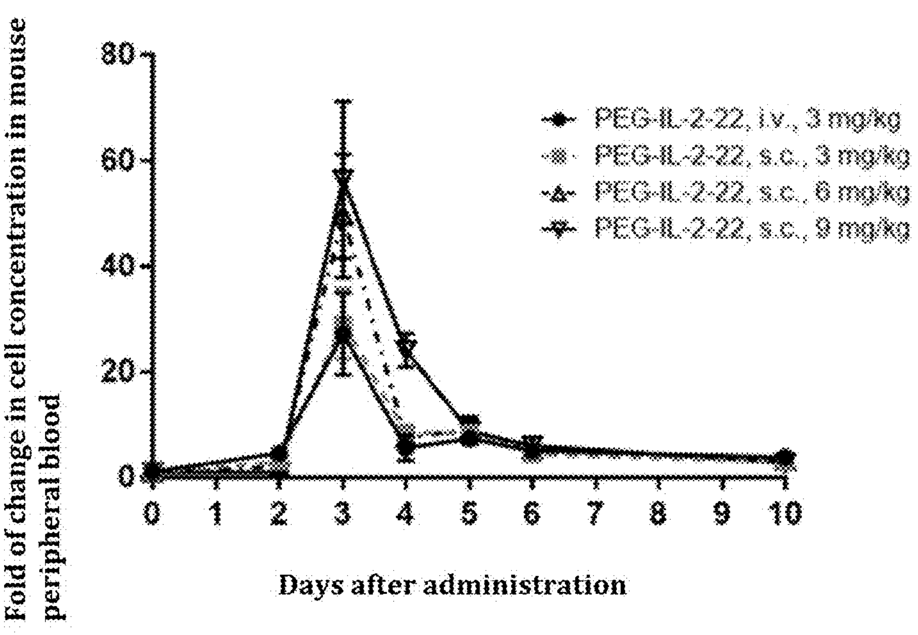
FIGS. 7A to 7D are the experimental results indicating the effects of PEG-IL-2-22 on the numbers of mouse NK cells (FIG. 7A), CD8+ T (FIG. 7B) cells, CD4+ T cells (FIG. 7C) and Treg cells (FIG. 7D), respectively.
Figure 7B:
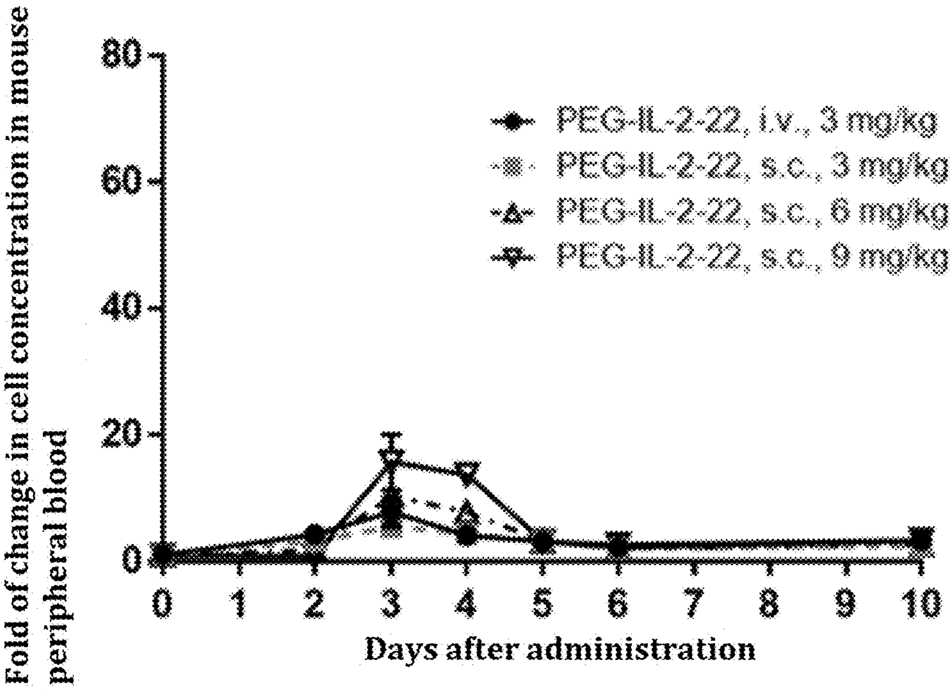
Figure 7C:
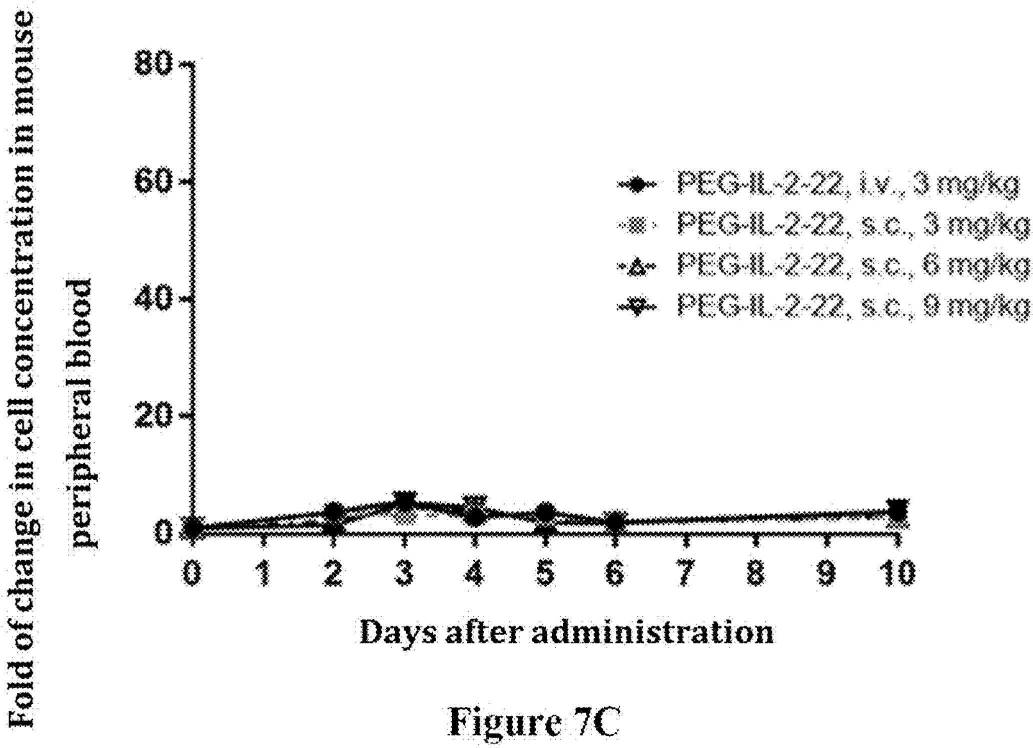
Figure 7D:
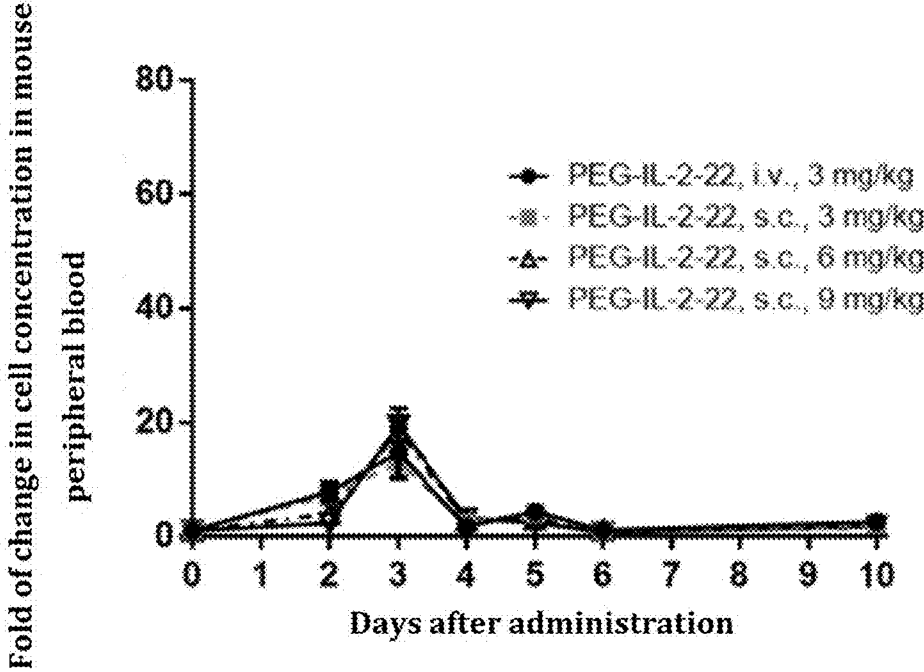
Figure 8A:
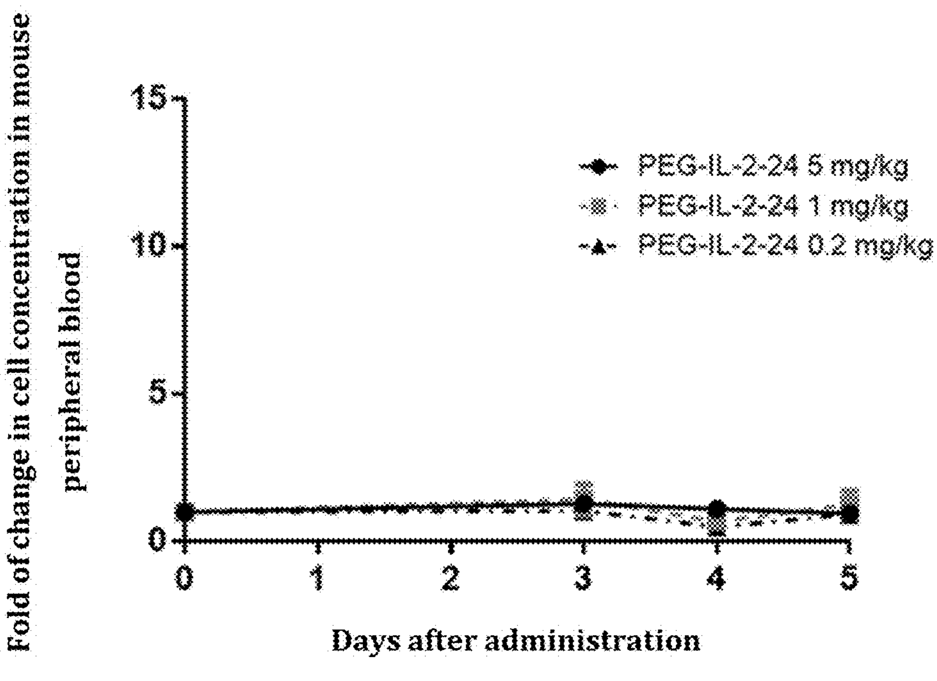
FIGS. 8A to 8C are the experimental results indicating the effects of PEG-IL-2-24 on the numbers of mouse CD8+ T cells (FIG. 8A), CD4+ T cells (FIG. 8B), and Treg cells (FIG. 8C), respectively.
Figure 8B:
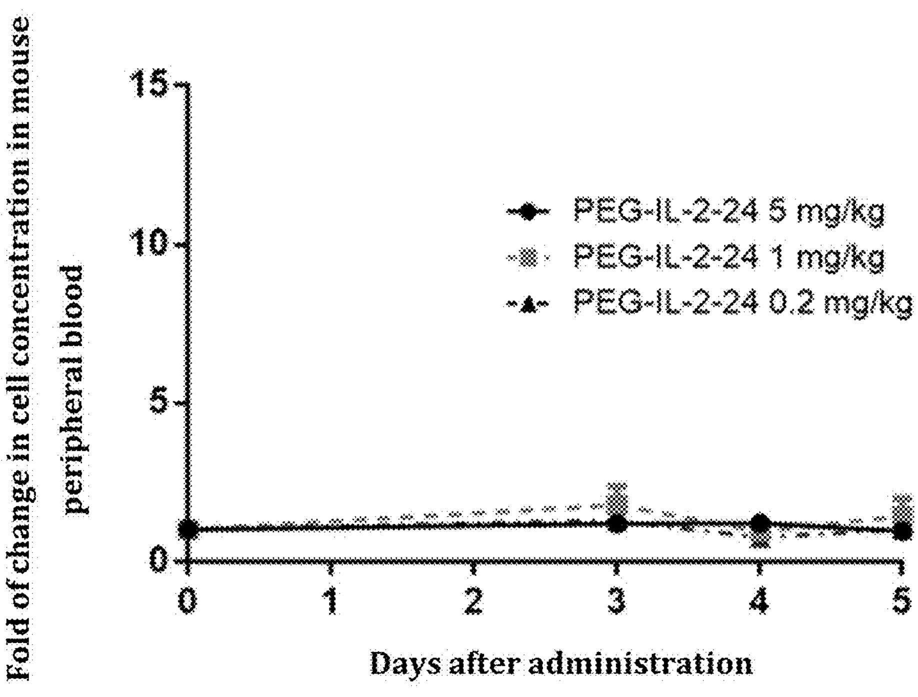
Figure 8C:
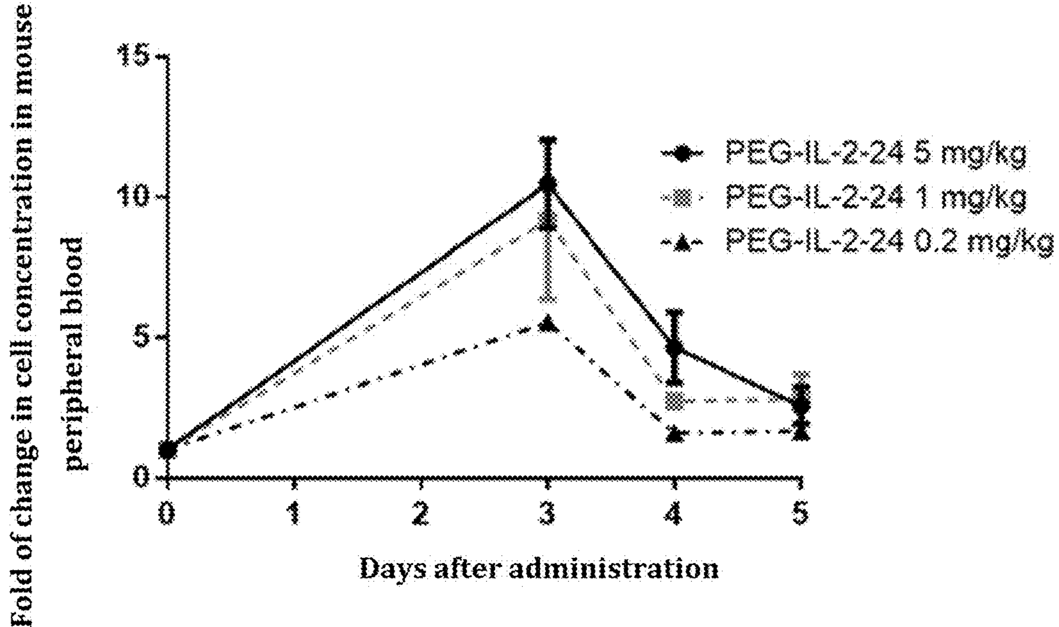
Figure 8D:
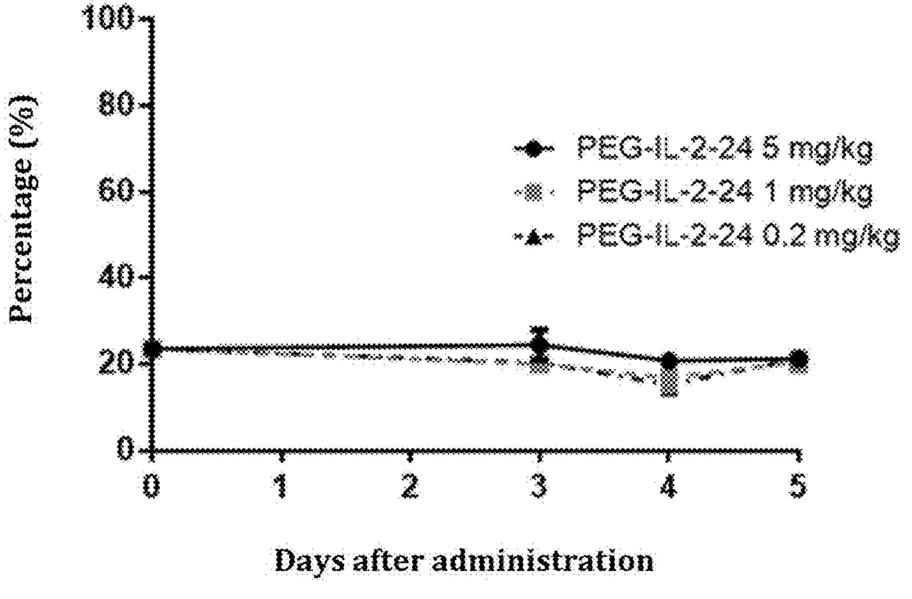
FIGS. 8D to 8F show the corresponding percentage of CD8+ T cells to CD3+ T cells (FIG. 8D), the percentage of CD4+ T cells to CD3+ T cells (FIG. 8E), and the percentage of Treg cells to CD4+ T cells (FIG. 8F), respectively.
Figure 8E:
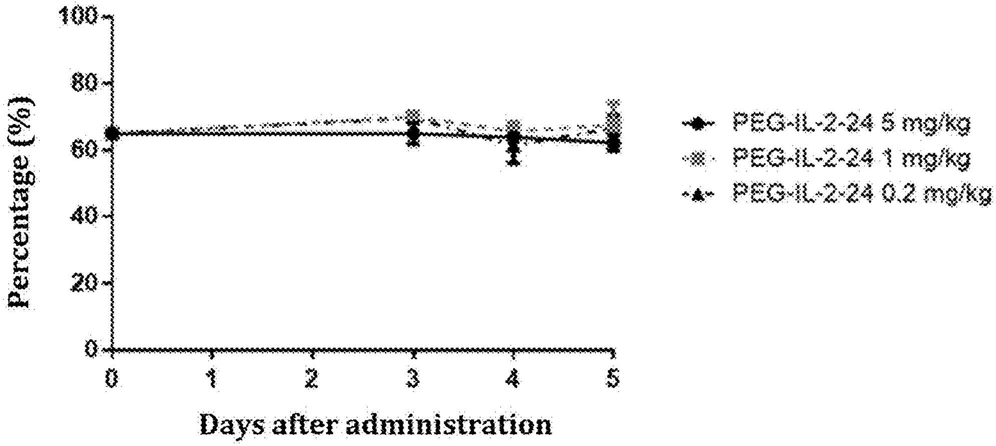
Figure 8F:
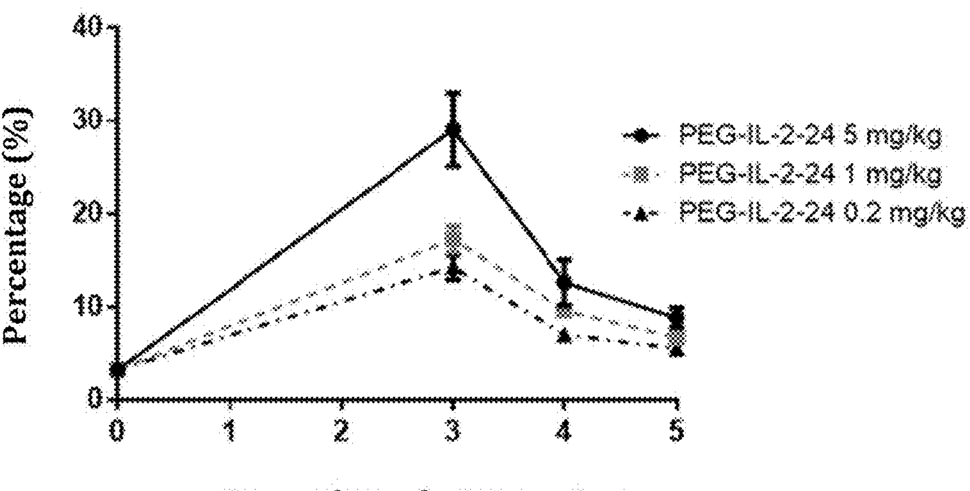

Data of the activity of IL-2 variant in STAT5 phosphorylation in PBMC cells are shown in Table 13, Table 14, Table 15, and FIGS. 6A-6C.

TABLE 13

Activity of IL-2 and the variant thereof in STAT5 phosphorylation in human Treg cells

| Name | Mutation (amino acid SEQ ID NO.) | $EC_{50}$ (nM) | relative biological activity |
|---|---|---|---|
| IL-2 | wild type (SEQ ID NO: 2) | 0.00046 | 100% |
| PEG-IL-2-10 | N26Q/N30S/F42A/L72G (SEQ ID NO: 22) | 2.65 | 0.02% |
| PEG-IL-2-23 | Q11C/NNYKNPKLTRMLTFKF at positions 29-44 mutated into QSMHIDATL/L132C (SEQ ID NO: 36) | 4.24 | 0.01% |
| IL-2-24 | N26Q/N29S/N88R (SEQ ID NO: 38) | 0.209 | 0.2% |
| PEG-IL-2-24 | | 6.02 | 0.007% |

TABLE 14

The activity of IL-2 and the variant thereof in phosphorylation in human CD8+T cells

| Name | $EC_{50}$ (nM) | relative activity |
|---|---|---|
| IL-2 | 2.32 | 100% |
| PEG-IL-2-10 | 8.97 | 26% |
| PEG-IL-2-23 | 14.41 | 16% |
| IL-2-24 | N.A. | N.A. |
| PEG-IL-2-24 | N.A. | N.A. |

(Note: N.A., undetectable, indicating that the activity of the variant in STAT5 phosphorylation is lower in CD8+ T cells, and the EC50 cannot be obtained by fitting the data within the concentration range used in the experiment).

TABLE 15

Activity of IL-2 and the variant thereof in STAT5 phosphorylation in human NK cells

| Name | $EC_{50}$ (nM) | relative activity |
|---|---|---|
| IL-2 | 0.48 | 100% |
| PEG-IL-2-10 | 2.00 | 24% |
| PEG-IL-2-23 | 2.88 | 17% |

Example 10: Determination of the Effect of IL-2 and the Variant Thereof on the Peripheral Blood Immune Cells of Balb/c Mice BALB/c mice (purchased from Shanghai Lingchang Biotechnology Co., Ltd.), female, 4-8 weeks old, weighing 18-20 g, were allowed to acclimate for 5 days before the formal experiment. All BALB/c mice were raised in an SPF-grade animal house IVC with constant temperature and pressure system, where the temperature was 20 to 26° C., the humidity was 40 to 70%, and the light cycle was 12-hour light/12-hour dark. There were no more than 6 BALB/c mice in each cage. The cage size was 325 mm×210 mm×180 mm. The bedding material in the cage was corncob, which was renewed twice a week. During the entire experiment, all laboratory mice were freely accessible to feed and drink, and the feed and water were autoclaved and renewed twice a week. All personnel entering and exiting the animal breeding house or experiment operators wore sterilized laboratory clothes, disposable medical masks and rubber gloves. Each cage had a corresponding clear and detailed label. The label content included: IACUC approval number LDIACUC006, number of animals, gender, strain, date of inclusion, item number, grouping, current experimental stage and experimental person in charge, etc. Throughout the experiment, the operation and observation of experimental animals were carried out in accordance with the regulations of AAALAC animal operation and management. In accordance with the routine experiment process, the behavior, feed and water intake, change in weight, hair gloss and other abnormal conditions of all laboratory animals were monitored and recorded.

The mice were grouped according to body weight, and the administration started after grouping. The type of administration, dose and route of administration are shown in Table 16 and FIGS. 7A-7D. The day on which mice were grouped is set as day 0.

Blood was collected at each time point and the blood volume was measured, the freshly collected anticoagulant blood was lysed with red blood cell lysate to lyse the red blood cells, and washed once with PBS. The mixed staining solution was prepared with PBS comprising 1% FBS. The mixed staining solution comprised CD3 APC-Cy7 (Biolegend 100329), CD8 PE (Biolegend 100708), CD4 PE-Cy7 (eBioscience 25-0042-82), CD25 PerCP-Cy5.5 (BD 561112) and CD49b-APC (Biolegend 108909). 100 μL of mixed staining solution was added to each sample and incubated at 4° C. for 30 minutes. The sample was washed twice with PBS comprising 1% FBS. True-Nuclear™ Transcription Factor Buffer Set (Biolegend 424401) was used to fix samples for 60 minutes, for digestion of cell membrane. 100 μL of anti-mouse Foxp3 antibody (Biolegend 126405) was incubated for 60 minutes at room temperature. The samples were washed twice with PBS pH 7.4 washing solution, and were finally re-suspended with 500 μL PBS pH 7.4 washing solution, for analysis on the machine. NK cells are defined as CD3-CD49b+ cells, CD8+ T cells are defined as CD3+CD4-CD8+ cells, and Tregs are defined as CD3+CD4+CD25+Foxp3+ cells. According to the blood sampling volume, the cell density of each cell group in the peripheral blood was calculated.

TABLE 16

Dosing regimen for treatment by PEG-IL-2-22

| Group | Number of animals | Administration | Dose (mg/kg) | Route of administration | Time of administration | Time point for blood sampling (d) |
|---|---|---|---|---|---|---|
| 1 | 3 | PEG- | 3 | i.v. | single | 0, 3, 5, 10 |
| 2 | 3 | IL-2-22 | | i.v. | admin- | 2, 4, 6 |
| 3 | 3 | | 3 | s.c. | istration | 0, 3, 5, 10 |
| 4 | 3 | | | s.c. | since the | 2, 4, 6 |
| 5 | 3 | | 6 | s.c. | beginning | 3, 5, 10 |
| 6 | 3 | | | s.c. | of the | 2, 4, 6 |
| 7 | 3 | | 9 | s.c. | test | 3, 5, 10 |
| 8 | 3 | | | s.c. | | 2, 4, 6 |

During the experiment, PEG-IL-2-22 was administered via tail vein injection on day 0, mouse blood was collected and analyzed with flow cytometry on day 0, 2, 3, 4, 5, 6, and 10, respectively. The results of the density of each cell population in blood show that the density of $CD3^{-}CD49b^{+}$ NK cells in mouse whole blood cells is increased significantly on day 3 in a dose-dependent manner, when compared with that on day 0, and on day 10 the density basically reverts to the level of pre-dosing. The density of CD8+ T cells is increased significantly on day 3 in a dose-dependent manner, and basically reverts to the level of pre-dosing on day 5. The density of regulatory T cells (Tregs) is increased significantly on day 3, the density basically reverts to the level of pre-dosing on day 4.

During the experiment, all groups of mice administered with different doses of PEG-IL-2-22 to be tested do not show weight loss or abnormal behavior, indicating that the mice have a favorable tolerance to the medicament at the doses to be tested.

TABLE 17

Administration and treatment by PEG-IL-2-24

| Group | Number of animals | Treatment | Dose (mg/kg) | Route of administration | Time of administration | Time point for blood sampling (d) |
|---|---|---|---|---|---|---|
| 1 | 3 | PEG- | 0.2 | i.p. | single | 0, 3, 4, 5 |
| 2 | 3 | IL-2-24 | 1 | i.p. | admin- | 0, 3, 4, 5 |
| 3 | 3 | | 5 | i.p. | istration since the beginning of the test | 0, 3, 4, 5 |

(Note: i.v., tail vein injection; s.c., subcutaneous injection; i.p., intraperitoneal injection).

The results show that PEG-IL-2-24 can stimulate the proliferation of Tregs at high (5 mg/kg), medium (1 mg/kg), and low (0.2 mg/kg) doses after three days of administration in a dose-dependent manner; the percentages of CD4+ T cells and CD8+ T cells in CD3+ T cells do not change at the three doses, showing a preferential activation on Tregs by PEG-IL-2-24. The results are shown in FIGS. 8A-8F.

Example 11: Evaluation of the Efficacy of IL-2 and the Variant Thereof in Mouse Models of Murine-Derived Colon Cancer Tumor Murine-derived colon adenocarcinoma CT26. WT cells (from the Cell Bank, in Chinese Academy of Sciences (SIBC), Shanghai) were expanded after thawing P4+1 generation of cells, and cultivated in DMEM medium containing 10% fetal bovine serum (FBS). CT26.WT cells in exponential growth phase were collected, re-suspended in HBSS to reach $1\times10^{6}$/mL, transplanted subcutaneously into BALB/c mice under aseptic conditions, and each mouse was inoculated with $1\times10^{5}$ cells. When the tumor volume reached about 80-100 $mm^3$, the animals were divided into groups. The first administration started after grouping. The detailed administration method, dose and route of administration are shown in Table 18. The day on which the mice were grouped is set as day 0.

TABLE 18

The dosing regimen of PEG-IL-2-22

| Group | Number of animals | Treatment | Dose (mg/kg) | Route of administration | Frequency of administration |
|---|---|---|---|---|---|
| 1 | 6 | PBS | — | s.c. | Q5D |
| 2 | 6 | PEG-IL-2- | 3 | s.c. | Q5D |
| 3 | 6 | 22 | 6 | s.c. | Q5D |
| 4 | 6 | | 9 | s.c. | Q5D |
| 5 | 6 | | 3 | i.v. | Q5D |
| 6 | 6 | | 6 | i.v. | Q5D |

(Note: i.v., tail vein injection; s.c., subcutaneous injection. Q5D, administrated once every five days. Dosing volume: the dosing volume was adjusted according to the body weight of the mouse (0.1 mL/10 g)).

Figure 9:
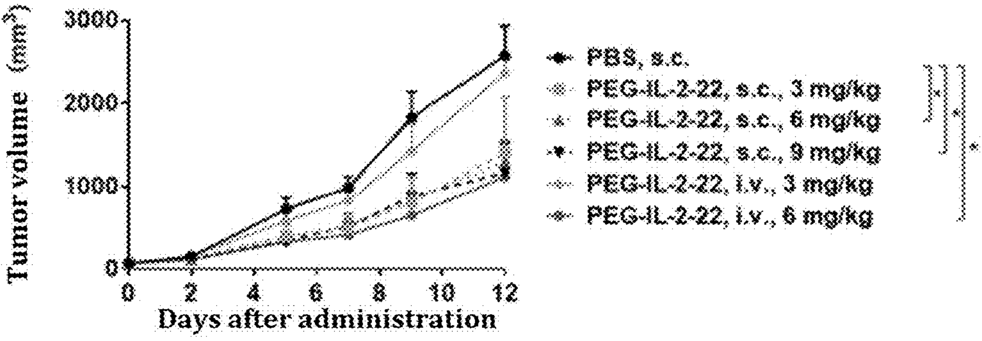
FIG. 9 is a graph showing the results of anti-tumor effect of PEG-IL-2-22 in the mouse CT26 colon cancer model.

After the administration was started, the weight and tumor volume of mice were measured 3 times a week, and tumor volume was calculated as: tumor volume ($mm^3$)=0.5×(tumor long diameter×tumor short diameter$^2$). Relative tumor inhibition rate TGI (%) was calculated as: TGI %=(1−T/C)×100%. T/C % is the relative rate of tumor growth (i.e. the relative percentage value of the tumor volume or tumor weight between the treatment group and the control group, at a certain time point). T and C represent tumor volume (TV) or tumor weight (TW) of the treatment group and the control group, at a specific time point, respectively. The experimental results are shown in Table 19 and FIG. 9.

TABLE 19

Anti-tumor effect of PEG-IL-2-22 in CT26 tumor model

| Group | tumor volume at day 0 ($mm^3$) | tumor volume at day 12 ($mm^3$) | TGI (%) | T/C (%) | p value |
|---|---|---|---|---|---|
| 1 | 72.3 ± 5.31 | 2577.6 ± 360.91 | | | |
| 2 | 72.2 ± 6.03 | 1410.5 ± 673.38 | 47 | 53 | 0.1576 |
| 3 | 70.9 ± 5.37 | 1297.5 ± 263.52 | 51 | 49 | 0.0168 |
| 4 | 71.8 ± 5.33 | 1168.6 ± 352.3 | 56 | 44 | 0.0190 |
| 5 | 70.1 ± 5.53 | 2369.4 ± 547.49 | 8 | 92 | 0.7574 |
| 6 | 69.8 ± 5.85 | 1122.2 ± 418.6 | 58 | 42 | 0.0265 |

The efficacy of PEG-IL-2-22 with different doses and different administration modes was tested in CT26 allograft model of mice colon cancer cells, in this experiment. The results show that: in medium-dose group of the subcutaneous administration (G3), PEG-IL-2-22 6 mg/kg s.c. Q5D*5 shows an average tumor volume of 1297.5±263.52 $mm^3$ on day 12 after administration, which is significantly lower than that in the control group on the same day (with a tumor volume of 2577.6±360.91 $mm^3$, TGI=51%, p=0.0168). In high-dose group of the subcutaneous administration (G4), PEG-IL-2-22 9 mg/kg s.c. Q5D*5 shows an average tumor volume of 1168.6±352.3 $mm^3$ on day 12 after administration, which is significantly lower than that in the control group on the same day (with a tumor volume of 2577.6±360.91 $mm^3$, TGI=56%, p=0.0190). In medium-dose group of the intravenous administration (G6), PEG-IL-2-22 6 mg/kg i.v. Q5D*5 shows an average tumor volume of 1122.2±418.6 $mm^3$ on day 12 after administration, which is significantly lower than that in the control group on the same day (with a tumor volume of 2577.6+360.91 $mm^3$, TGI=58%, p=0.0265).

Example 12: Evaluation of the Efficacy of IL-2 and the Variant Thereof in a Mouse Model of Human Melanoma Tumor NCG mice, female, 4-8 weeks old, weighing about 18-22 g, were purchased from Jiangsu GemPharmatech Biotechnology Co., Ltd. All NCG mice were raised in an SPF-grade animal house IVC with constant temperature and pressure system.

A375 cells were cultivated in DMEM medium comprising 10% fetal bovine serum (FBS). A375 cells in the exponential growth phase were collected, and HBSS was re-suspended to a suitable concentration for subcutaneous inoculation of tumor in NCG mice. The A375 cells used for co-cultivation should be treated with Mitomycin C for 2 h, and then washed three times with PBS. The normal human peripheral blood was collected to separate human PBMCs by density gradient centrifugation, and cells were counted. Then, PBMCs was re-suspended to a concentration of $3\times10^6$ cells/mL with RPMI1640 medium (comprising IL-2 and 10% FBS), and co-cultivated with A375 cells treated with Mitomycin C. After 8 days of co-cultivation, PBMCs were collected, and freshly digested A375 cells were also collected. Each mouse was inoculated with: PBMCs of $8\times10^5$, A375 cells of $4\times10^6$; Inoculation volume: 0.2 ml/mouse (comprising 50% Matrigel); subcutaneously inoculated on the right flank of female NCG mice, a total of 30 mice were inoculated. The mice were randomly divided into groups according to body weight. The detailed administration mode, dose and route of administration are shown in Table 20. The day on which the mice were grouped for administration is set as day 0.

TABLE 20 dosing regimen of PEG-IL-2-22

| Group | Administration group | N | Dose (mg/kg) | Dosing regimen | Route of administration |
|---|---|---|---|---|---|
| 1 | PBS | 6 | — | Q3D | i.v. |
| 2 | PEG-IL-2-22 | 6 | 0.03 | Q3D | i.v. |
| 3 | | 6 | 0.1 | Q3D | i.v. |
| 4 | | 6 | 0.03 | Q3D | s.c. |
| 5 | | 6 | 0.1 | Q3D | s.c. |

(Note: N: number of animals used. i.v.: tail vein injection; s.c.: subcutaneous injection. Q3D: administrated once every three days. Dosing volume: the dosing volume was adjusted according to the weight of the tumor-bearing mice (0.1 mL/10 g)).

Figure 10:
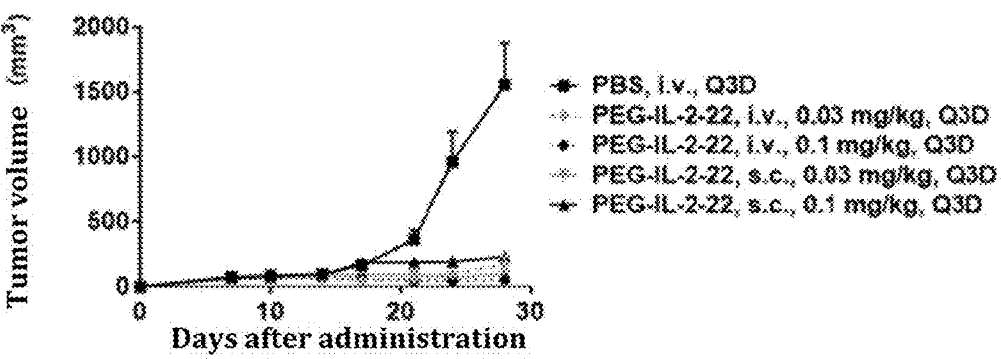
FIG. 10 is a graph showing the results of anti-tumor effect of PEG-IL-2-22 in the NCG mouse model subcutaneously transplanted with human melanoma A375 mixed with human PBMC.

Once the administration started, the weight and tumor volume of mice were measured twice a week. The experimental results are shown in Table 21 and FIG. 10, respectively.

TABLE 21

Anti-tumor effect of PEG-IL-2-22 in mouse model of human A375 tumor

| Group | Tumor volume on day 0 ($mm^3$) | Tumor volume on day 27 ($mm^3$) | TGI (%) | T/C (%) | P value |
|---|---|---|---|---|---|
| 1 | 0 ± 0 | 1558.55 ± 320.54 | | | |
| 2 | 0 ± 0 | 175.75 ± 64.16 | 88.72 | 11.28 | <0.001 |
| 3 | 0 ± 0 | 55.62 ± 15.18 | 96.43 | 3.57 | <0.001 |
| 4 | 0 ± 0 | 95.08 ± 37.27 | 93.90 | 6.10 | <0.001 |
| 5 | 0 ± 0 | 232.23 ± 35.68 | 85.10 | 14.90 | <0.001 |

At the end of the experiment (day 27 after administration), tumor volume and tumor weight in administration group of PEG-IL-2-22 (0.03 mg/kg, tail vein injection), administration group of PEG-IL-2-22 (0.1 mg/kg, tail vein injection), administration group of PEG-IL-2-22 (0.03 mg/kg, subcutaneous injection), administration group of PEG-IL-2-22 (0.1 mg/kg, subcutaneous injection) are significantly different from those in PBS group (P value is less than 0.001), indicating a significant inhibitory effect on tumor growth.

Example 13: Immunogenicity Analysis of IL-2 and the Variant Thereof

By computer-simulation analysis, the number of simulated T cell epitope (TCE) calculated by using IL-2 variant is roughly equivalent to or less than that of wild type IL-2 (see Table 22). The results show that the amino acid mutation(s) in each IL-2 variant will not cause adverse effects on the immunogenicity of IL-2, for therapeutic-related purposes.

TABLE 22

T cell epitopes of IL-2 variants

| Number | Number of TCE | TCE | | | | | |
|---|---|---|---|---|---|---|---|
| IL-2 | 5 | LISNINVIV | FKFYMPKKA | MILNGINNY | LTRMLTFKF | MLTFKFYMP | |
| IL-2-01 | 4 | FKFYMPKKA | LISNINVIV | LTRMLTFKF | MLTFKFYMP | | |
| IL-2-02 | 6 | MILNGINSY | FKFYMPKKA | LTRMLTFKF | LISNINVIV | INSYKNPKL | MLTFKFYMP |
| IL-2-03 | 5 | LISNINVIV | FKFYMPKKA | MILNGINNY | LTRMLTFKF | MLTFKFYMP | |
| IL-2-04 | 5 | LISNINVIV | FKFYMPKKA | MILNGINNY | LTRMLTFKF | MLTFKFYMP | |
| IL-2-05 | 5 | MILNCINNY | FKFYMPKKA | LISNINVIV | LTRMLTFKF | MLTFKFYMP | |
| IL-2-06 | 5 | LISNINVIV | MHIDATLYM | IQSMHIDAT | MILNGIQSM | LNGIQSMHI | |
| IL-2-07 | 4 | TRMLTAKFA | LISNINVIV | MILNGINNY | LTRMLTAKF | | |
| IL-2-08 | 3 | LISNINVIV | MILNGINNY | LTRMLTAKF | | | |
| IL-2-09 | 6 | FKFAMPKKA | MILNGINNY | LTRMLTFKF | RMLTFKFAM | LISNINVIV | MLTFKFAMP |
| IL-2-10 | 3 | LISNINVIV | LTRMLTAKF | INSYKNPKL | | | |
| IL-2-11 | 3 | LISNINVIV | LTRMLTAKF | INSYKNPKL | | | |
| IL-2-12 | 3 | LISNINVIV | LTRMLTAKF | INSYKNPKL | | | |
| IL-2-13 | 3 | LISNINVIV | LTRMLTAKF | INSYKNPKL | | | |
| IL-2-14 | 3 | LISNINVIV | MILNGISNY | LTRMLTAKF | | | |
| IL-2-21 | 2 | LISNINVIV | LTRMLTAKF | | | | |
| IL-2-22 | 2 | LISNINVIV | LTRMLTAKF | | | | |
| IL-2-23 | 5 | LISNINVIV | MHIDATLYM | IQSMHIDAT | MILNGIQSM | LNGIQSMHI | |

What is claimed is:

1. An IL-2 variant consisting of mutations selected from:
(i) N26Q, N29S, F42A, N71Q and L72G; or
(ii) N26Q, N29S, F42A, N71Q, L72G and C125A;
wherein the mutations thereof are relative to a wild type IL-2, the amino acid sequence of which is as shown in SEQ ID NO: 2, and the numbering of the mutation position is counted from the amino acid A at the second position according to the amino acid sequence shown in SEQ ID NO: 2.

2. The IL-2 variant according to claim 1, wherein the stability of the IL-2 variant is increased when compared to the stability of wild type IL-2.

3. The IL-2 variant according to claim 1, represented by SEQ ID NO: 34.

4. A pharmaceutical composition, comprising the IL-2 variant of claim 1 and a pharmaceutically acceptable diluent (s), carrier(s) or adjuvant(s).

* * * * *